US012760289B2

(12) United States Patent
Sontheimer et al.

(10) Patent No.: US 12,760,289 B2
(45) Date of Patent: Oct. 13, 2026

(54) ANTI-CRISPR COMPOUNDS AND METHODS OF USE

(71) Applicants: UNIVERSITY OF MASSACHUSETTS, Boston, MA (US); THE GOVERNING COUNCIL OF THE UNIVERSITY OF TORONTO, Toronto (CA)

(72) Inventors: Erik Sontheimer, Auburndale, MA (US); Alan Davidson, Toronto (CA); Karen Maxwell, Toronto (CA); April Pawluk, Cambridge, MA (US); Yan Zhang, Ann Arbor, MI (US); Jooyoung Lee, Worcester, MA (US); Nadia Amrani, Shrewsbury, MA (US)

(73) Assignees: The Governing Council Of The University Of Toronto, Ontario (CA); University of Massachusetts, Massachusetts (MA)

( * ) Notice: Subject to any disclaimer, the term of this patent is extended or adjusted under 35 U.S.C. 154(b) by 249 days.

(21) Appl. No.: 17/959,019

(22) Filed: Oct. 3, 2022

(65) Prior Publication Data

US 2023/0167426 A1 Jun. 1, 2023

Related U.S. Application Data

(63) Continuation of application No. 16/084,397, filed as application No. PCT/US2017/022040 on Mar. 13, 2017, now Pat. No. 11,530,394.

(60) Provisional application No. 62/497,097, filed on Nov. 7, 2016, provisional application No. 62/308,417, filed on Mar. 15, 2016.

(51) Int. Cl.

| | |
|---|---|
| ***C12N 15/00*** | (2006.01) |
| ***C12N 9/22*** | (2006.01) |
| ***C12N 15/90*** | (2006.01) |

(52) U.S. Cl.

CPC ............. *C12N 9/22* (2013.01); *C12N 15/907* (2013.01)

(58) Field of Classification Search

CPC ................................ C12N 9/22; C12N 15/907

See application file for complete search history.

(56) References Cited

U.S. PATENT DOCUMENTS

| | | | | |
|---|---|---|---|---|
| 5,364,634 | A | 11/1994 | Lew | 424/451 |
| 5,705,188 | A | 1/1998 | Junichi et al. | 424/450 |
| 6,113,948 | A | 9/2000 | Heath et al. | 424/499 |
| 2014/0357523 | A1 | 12/2014 | Zeiner et al. | 435/6.1 |

FOREIGN PATENT DOCUMENTS

| | | |
|---|---|---|
| WO | WO/2014/093479 | 6/1914 |
| WO | WO/2015/048577 | 4/1915 |
| WO | WO/1997/030731 | 8/1997 |

OTHER PUBLICATIONS

Pawluck_et_al_Cell_Vol_167_No_7_pp_1829-1838_Mar._15_2016 (Year: 2016).*

Anders, C. et al. (2014) "Structural basis of PAM-dependent target DNA recognition by the Cas9 endonuclease," *Nature* 513(7519), 569-573.

Barrangou, R. et al. (2007) "CRISPR Provides Acquired Resistance Against Viruses in Prokaryotes," *Science* 315(5819), 1709-1712.

Bikard, D. et al. (2014) "Development of sequence-specific antimicrobials based on programmable CRISPR-Cas nucleases," *Nature Biotechnology* 32(11), 1146-1150.

Bolukbasi, M. F. et al. (2015) "Creating and evaluating accurate CRISPR-Cas9 scalpels for genomic surgery," *Nature Methods* 13, 41-50.

Bondy-Denomy, J. et al. (2015) "Multiple mechanisms for CRISPR-Cas inhibition by anti-CRISPR proteins," *Nature* 526(7571), 136-139.

Bondy-Denomy, J et al. (2012) "Bacteriophage genes that inactivate the CRISPR/Cas bacterial immune system," *Nature* 493, 429-432.

Bondy-Denomy, J. W. (2014) The Diverse Impact of Bacteriophages on the Bacterial Host, in *Molecular Genetics*, University of Toronto, University of Toronto.

Cho, S. W. et al. (2013) "Targeted genome engineering in human cells with the Cas9 RNA-guided endonuclease," *Nature Biotechnology* 31(3), 230-232.

Cong, L. et al. (2013) "Multiplex Genome Engineering Using CRISPR/Cas Systems," *Science* (New York, N.Y.) 339(6121), 819-823.

Davis, K. M. et al. (2015) "Small Molecule-Triggered Cas9 Protein with Improved Genome-Editing Specificity," *Nature Chemical Biology* 11(5), 316-318.

(Continued)

*Primary Examiner* — Catherine S Hibbert

(74) *Attorney, Agent, or Firm* — Medlen & Carroll, LLP

(57) ABSTRACT

The present invention is related to the field of CRISPR-Cas9 gene editing platforms. In particular, the present invention has identified Type II-C Cas9 anti-CRISPR (Acr) inhibitors that control Cas9 gene editing activity. Co-administration of such Acr inhibitors may provide an advantageous adjunct in permitting safe and practical biological therapeutics through spatial or temporal control of Cas9 activity; controlling Cas9-based gene drives in wild populations to reduce the ecological consequences of such forced inheritance schemes; and contributing to general research into various biotechnological, agricultural, and medical applications of gene editing technologies.

10 Claims, 44 Drawing Sheets

(17 of 44 Drawing Sheet(s) Filed in Color)

Specification includes a Sequence Listing.

(56) References Cited

OTHER PUBLICATIONS

Deltcheva, E. et al. (2011) "CRISPR RNA maturation by trans-encoded small RNA and host factor RNase III," *Nature* 471(7340), 602-607.
Dominguez, A. A. et al. (2016) "Beyond editing: repurposing CRISPR-Cas9 for precision genome regulation and interrogation," *Nature Reviews. Molecular Cell Biology* 17(1), 5-15.
Doudna, J. A. et al. (2014) "Genome editing. The new frontier of genome engineering with CRISPR-Cas9," *Science* 346(6213), Article No. 1258096.
Duffin, P. M. et al. (2012) "Genetic transformation of Neisseria gonorrhoeae shows a strand preference," *FEMS Microbiology Letters* 334(1), 44-48.
Ebina, H. et al. (2013) "Harnessing the CRISPR/Cas9 system to disrupt latent HIV-1 provirus," *Scientific Reports* 3, Article No. 2510.
Edgar, R. C. (2004) "MUSCLE: multiple sequence alignment with high accuracy and high throughput," *Nucleic Acids Research* 32(5), 1792-1797.
Esvelt, K. M. et al. (2013) "Orthogonal Cas9 Proteins for RNA-Guided Gene Regulation and Editing," *Nature Methods* 10(11), 1116-1121.
Fineran, P. C. et al. (2014) "Degenerate target sites mediate rapid primed CRISPR adaptation," *Proceedings of the National Academy of Sciences* 111(16), E1629-E1638.
Fonfara, I. et al. (2014) "Phylogeny of Cas9 determines functional exchangeability of dual-RNA and Cas9 among orthologous type II CRISPR-Cas systems," *Nucleic Acids Research* 42(4), 2577-2590.
Fu, Y. et al. (2014) "Improving CRISPR-Cas nuclease specificity using truncated guide RNAs," *Nature Biotechnology* 32(3), 279-284.
Gantz, V. M. et al. (2015) "Highly efficient Cas9-mediated gene drive for population modification of the malaria vector mosquito Anopheles stephensi," *Proceedings of the National Academy of Sciences* 112(49), E6736-6743.
Gasiunas, G. et al. (2012) "Cas9-crRNA ribonucleoprotein complex mediates specific DNA cleavage for adaptive immunity in bacteria," *Proceedings of the National Academy of Sciences of the United States of America* 109(39), E2579-E2586.
Gomaa, A. A. et al. (2014) "Programmable Removal of Bacterial Strains by Use of Genome-Targeting CRISPR-Cas Systems," *mBio* 5(1).
Gophna, U. et al. (2015) "No evidence of inhibition of horizontal gene transfer by CRISPR-Cas on evolutionary timescales," *ISME Journal* 9, 2021-2027.
Górski, A. et al. (2012) "Chapter 2—Phage as a Modulator of Immune Responses: Practical Implications for Phage Therapy," in *Advances in Virus Research* (Łobocka, M., et al., Eds.), pp. 41-71, Academic Press.
Guschin, D. Y. et al. (2010) "A rapid and general assay for monitoring endogenous gene modification," *Methods in Molecular Biology* 649, 247-256.
Hammond, A. et al. (2015) "A CRISPR-Cas9 gene drive system targeting female reproduction in the malaria mosquito vector Anopheles gambiae," *Nature Biotechnology* 34(1), 78-83.
Heler, R. et al. (2015) "Cas9 specifies functional viral targets during CRISPR-Cas adaptation," *Nature* 519(7542), 199-202.
Hilton, I. B. et al. (2015) "Epigenome editing by a CRISPR/Cas9-based acetyltransferase activates genes from promoters and enhancers," *Nature Biotechnology* 33(5), 510-517.
Hirano, H. et al. (2016) "Structure and Engineering of Francisella novicida Cas9," *Cell* 164(5), 950-961.
Ho, S. N. et al. (1996) "Dimeric ligands define a role for transcriptional activation domains in reinitiation," *Nature* 382(6594), 822-826.
Hou, Z. et al. (2013) "Efficient genome engineering in human pluripotent stem cells using Cas9 from Neisseria meningitidis," *Proceedings of the National Academy of Sciences* 110(39), 15644-15649.
Hsu, P. D. et al. (2014) "Development and applications of CRISPR-Cas9 for genome engineering," *Cell* 157(6), 1262-1278.
Hsu, P. D. et al. (2013) "DNA targeting specificity of RNA-guided Cas9 nucleases," *Nature Biotechnology* 31(9), 827-832.
Hwang, W. Y. et al. (2013) "Heritable and Precise Zebrafish Genome Editing Using a CRISPR-Cas System," *PLoS One* 8(7), Article No. e68708.
Jiang, F. et al. (2015) "Structural Biology. A Cas9-guide RNA complex preorganized for target DNA recognition," *Science* 348(6242), 1477-1481.
Jiang, W. et al. (2013) "CRISPR-assisted editing of bacterial genomes," *Nature Biotechnology* 31(3), 233-239.
Jinek, M. et al. (2012) "A programmable dual-RNA-guided DNA endonuclease in adaptive bacterial immunity," *Science* 337(6096), 816-821.
Jinek, M. et al. (2013) "RNA-programmed genome editing in human cells," *eLife* 2, e00471.
Jinek, M. et al. (2014) "Structures of Cas9 Endonucleases Reveal RNA-Mediated Conformational Activation," *Science* 343(6176), Article No. 1247997.
Kaminski, R. et al. (2016) "Elimination of HIV-1 Genomes from Human T-lymphoid Cells by CRISPR/Cas9 Gene Editing," *Scientific Reports* 6, Article No. 22555.
Kazmierczak, Z. et al. (2014) "Molecular imaging of T4 phage in mammalian tissues and cells," *Bacteriophage* 4, e28364.
Kearns, N. A. et al. (2014) "Cas9 effector-mediated regulation of transcription and differentiation in human pluripotent stem cells," *Development* 141(1), 219-223.
Kearns, N. A. et al. (2015) "Functional annotation of native enhancers with a Cas9-histone demethylase fusion," *Nature Methods* 12(5), 401-403.
Kurzepa, A. et al. (2009) "Molecular modification of T4 bacteriophage proteins and its potential application—review," *Folia Microbiologica* 54(1), 5-15.
Lee, C. M. et al. (2016) "The Neisseria meningitidis CRISPR-Cas9 System Enables Specific Genome Editing in Mammalian Cells," *Molecular Therapy* 24(3), 645-654.
Ma, E. et al. (2015) "Single-Stranded DNA Cleavage by Divergent CRISPR-Cas9 Enzymes," *Molecular Cell* 60(3), 398-407.
Ma, H. et al. (2015) "Multicolor CRISPR labeling of chromosomal loci in human cells," *Proceedings of the National Academy of Sciences* 112(10), 3002-3007.
Makarova, K. S. et al. (2015) "An updated evolutionary classification of CRISPR-Cas systems," *Nature Reviews. Microbiology* 13(11), 722-736.
Mali, P. et al. (2013) "RNA-guided human genome engineering via Cas9," *Science* 339(6121), 823-826.
Miller, R. A. et al. (1977) "Degradation rates of oral resorbable implants (polylactates and polyglycolates): Rate modification with changes in PLA/PGA copolymer ratios," *Journal of Biomedical Materials Research* 11(5), 711-719.
Müller, M. et al. (2016) "*Streptococcus thermophilus* CRISPR-Cas9 Systems Enable Specific Editing of the Human Genome," *Molecular Therapy* 24(3), 636-644.
NCBI. (2014) "hypothetical protein [Pseudomonas aeruginosa)", Database accession No. WP 033945020.1, in *NCBI Database REFSEQ* [*Online*] Dec. 9, 2014 ed.
NCBI. (2014) "hypothetical protein [Brackiella oedipodfs]", Database accession No. WP 028357638.1, in *NCBI Database REFSEQ* [*Online*] Jun. 13, 2014 ed.
NCBI. (2015) "hypothetical protein [Neisseria meningitidis]", Database accession No. WP 049360089.1, in *NCBI Database REFSEQ* [*Online*] Jul. 20, 2015 ed.
NCBI. (2015) "hypothetical protein [Neisseria meningitidis)", Database accession No. WP 049344751.1, in *NCBI Database REFSEQ* [*Online*] Jul. 20, 2015 ed.
NCBI. (2015) "hypothetical protein [Neisseria meningitidis]", Database accession No. WP 049344838.1, in *NCBI Database REFSEQ* [*Online*] Jul. 20, 2015 ed.
NCBI. (2015) "hypothetical protein [Neisseria meningitidis]", Database accession No. WP 042743676.1, in *NCBI Database REFSEQ* [*Online*] Feb. 17, 2015 ed.

(56) References Cited

OTHER PUBLICATIONS

NCBI. (2015) "hypothetical protein [Neisseria meningitidis]", Database accession No. WP 042743678.1, in *NCBI Database REFSEQ* [*Online*] Feb. 17, 2015 ed.
Nihongaki, Y. et al. (2015) "Photoactivatable CRISPR-Cas9 for optogenetic genome editing," *Nature Biotechnology* 33(7), 755-760.
Nuñez, J. K. et al. (2016) "Chemical and Biophysical Modulation of Cas9 for Tunable Genome Engineering," *ACS Chemical Biology* 11(3), 681-688.
Orthwein, A. et al. (2015) "A mechanism for the suppression of homologous recombination in G1 cells," *Nature* 528(7582), 422-426.
Ousterout, D. G. et al. (2015) "Multiplex CRISPR/Cas9-based genome editing for correction of dystrophin mutations that cause Duchenne muscular dystrophy," *Nature Communications* 6, Article No. 6244.
Pattanayak, V. et al. (2013) "High-throughput profiling of off-target DNA cleavage reveals RNA-programmed Cas9 nuclease specificity," *Nature Biotechnology* 31(9), 839-843.
Pawluk, A. et al. (2016) "Naturally Occurring Off-Switches for CRISPR-Cas9," *Cell* 167(7), 1829-1838.
Pawluk, A. et al. (2014) "A New Group of Phage Anti-CRISPR Genes Inhibits the Type I-E CRISPR-Cas System of Pseudomonas aeruginosa," *mBio* 5(2).
Pawluk, A. et al. (2016) "Inactivation of CRISPR-Cas systems by anti-CRISPR proteins in diverse bacterial species," *Nature Microbiology* 1(8), Article No. 16085.
Pawluk, A. I. E. (2016) Prevalence, Diversity, Impact, and Applications of CRISPR-Cas Inhibitors, in *Biochemistry*, University of Toronto, University of Toronto.
Peränen, J. et al. (1996) "T7 Vectors with a Modified T7lacPromoter for Expression of Proteins in *Escherichia coli," Analytical Biochemistry* 236(2), 371-373.
Price, M. N. et al. (2009) "FastTree: Computing Large Minimum Evolution Trees with Profiles instead of a Distance Matrix," *Molecular Biology and Evolution* 26(7), 1641-1650.
Price, M. N. et al. (2010) "FastTree 2—Approximately Maximum-Likelihood Trees for Large Alignments," *PLoS One* 5(3), Article No. e9490.
Putney, S. D. et al. (1998) "Improving protein therapeutics with sustained-release formulations," *Nature Biotechnology* 16(2), 153-157.
Ran, F. A. et al. (2015) "In vivo genome editing using Staphylococcus aureus Cas9," *Nature* 520(7546), 186-191.
Ran, F. A. et al. (2013) "Double Nicking by RNA-Guided CRISPR Cas9 for Enhanced Genome Editing Specificity," *Cell* 154(6), 1380-1389.
Richter, C. et al. (2014) "Priming in the Type I-F CRISPR-Cas system triggers strand-independent spacer acquisition, bi-directionally from the primed protospacer," *Nucleic Acids Research* 42(13), 8516-8526.
Sander, J. D. et al. (2014) "CRISPR-Cas systems for editing, regulating and targeting genomes," *Nature Biotechnology* 32(4), 347-355.
Sander, J. D. et al. (2014) "CRISPR-Cas systems for genome editing, regulation and targeting," *Nature Biotechnology* 32(4), 347-355.
Sohrab, S. S. et al. (2014) "Bacteriophage—a common divergent therapeutic approach for Alzheimer's disease and type II diabetes mellitus," *CNS & Neurological Disorders: Drug Targets* 13(3), 491-500.
Sternberg, S. H. et al. (2014) "DNA interrogation by the CRISPR RNA-guided endonuclease Cas9," *Nature* 507(7490), 62-67.
Szczelkun, M. D. et al. (2014) "Direct observation of R-loop formation by single RNA-guided Cas9 and Cascade effector complexes," *Proceedings of the National Academy of Sciences of the United States of America* 111(27), 9798-9803.
Takeuchi, N. et al. (2012) "Nature and Intensity of Selection Pressure on CRISPR-Associated Genes," *Journal of Bacteriology* 194(5), 1216-1225.
Touchon, M. et al. (2016) "Genetic and life-history traits associated with the distribution of prophages in bacteria," *ISME Journal* 10, 2744-2754.
Tsai, S. Q. et al. (2014) "Dimeric CRISPR RNA-guided FokI nucleases for highly specific genome editing," *Nature Biotechnology* 32(6), 569-576.
UNIPROT. (2010) "SubName: Full=Uncharacterized protein {EC0:0000313J EMBL:CBJ38318.1};" Database accession No. D8NCYO, in UniProt Database [Online] Oct. 5, 2010 ed.
Van Houte, S. et al. (2016) "The diversity-generating benefits of a prokaryotic adaptive immune system," *Nature* 532(7599), 385-388.
Villefranc, J. A. et al. (2007) "Gateway Compatible Vectors for Analysis of Gene Function in the Zebrafish," *Developmental Dynamics* 236(11), 3077-3087.
Wang, H. et al. (2016) "CRISPR/Cas9 in Genome Editing and Beyond," *Annual Review of Biochemistry* 85(1), 227-264.
Wang, H. et al. (2013) "One-step generation of mice carrying mutations in multiple genes by CRISPR/Cas-mediated genome engineering," *Cell* 153(4), 910-918.
Wei, Y. et al. (2015) "Cas9 function and host genome sampling in Type II-A CRISPR-Cas adaptation," *Genes & Development* 29(4), 356-361.
Wright, A. V. et al. (2015) "Rational design of a split-Cas9 enzyme complex," *Proceedings of the National Academy of Sciences of the United States of America* 112(10), 2984-2989.
Wu, Y. et al. (2013) "Correction of a Genetic Disease in Mouse via Use of CRISPR-Cas9," *Cell Stem Cell* 13(6), 659-662.
Yata, T. et al. (2014) "Hybrid Nanomaterial Complexes for Advanced Phage-guided Gene Delivery," *Molecular Therapy—Nucleic Acids* 3(8), Article No. e185.
Yen, S.-T. et al. (2014) "Somatic mosaicism and allele complexity induced by CRISPR/Cas9 RNA injections in mouse zygotes," *Developmental Biology* 393(1), 3-9.
Yin, H. et al. (2014) "Genome editing with Cas9 in adult mice corrects a disease mutation and phenotype," *Nature Biotechnology* 32(6), 551-553.
Zetsche, B. et al. (2015) "A split-Cas9 architecture for inducible genome editing and transcription modulation," *Nature Biotechnology* 33, 139.
Zhang, Y. et al. (2014) "Comparison of non-canonical PAMs for CRISPR/Cas9-mediated DNA cleavage in human cells," *Scientific Reports* 4, Article No. 5405.
Zhang, Y. et al. (2013) "Processing-Independent CRISPR RNAs Limit Natural Transformation in Neisseria meningitidis," *Molecular Cell* 50(4), 488-503.
Zhang, Y. et al. (2015) "DNase H Activity of Neisseria meningitidis Cas9," *Molecular Cell* 60(2), 242-255.
PCT International Search Report of International Application No. PCT/US2017/022040 dated Aug. 1, 2017.
European Search Report for Application No. 17767247.4 dated Oct. 30, 2019.

* cited by examiner

Pull-down assay NmeCas9-sgRNA/Ni beads + purified ACR proteins

The purified ACR proteins indicated were mixed with Cas9 protein pre-bound to Ni-beads.
in: input
b: bound to Ni beads Pull-down assay NmeCas9-sgRNA/Ni beads + with purified ACR proteins The purified ACR proteins indicated were mixed with Cas9 protein pre-bound to Ni-beads. Cas9 pre-bound to Ni-beads was incubated with ACR1Nme, ACR2Nme or both as indicated.
in: input
b: bound to Ni beads

| Site | Gene or locus | Spacer sequence | Target site | SEQ ID NOS: |
|---|---|---|---|---|
| N-TS1C | SLC9A9 | GUGGUCUGGGGUACAGCCUUGGCA | TACTTGGTCTGGGGTACAGCCTTGGCATCATGATTTTG | 107, 108 |
| N-TS4B | FLJ00328 | GGACAGGAGUCGCCAGAGGCCGGU | GCAGGACAGGAGTCGCCAGAGGCCGGTGGTGGATTTCC | 109, 110 |
| N-TS4C | FLJ00328 | GGGGCUGGCUCCACGUCGCGCCGC | TGGGGGGCTGGCTCCACGTCGCGCCGCGGCCGTTTGGG | 111, 112 |
| N-TS7 | LOC100505797 | GAGGCAGAGAGGUGAGCGGAUGAA | GCAAAGGCAGAGAGGTGAGCGGATGAAGGGAGATTGGT | 113, 114 |
| N-TS8 | ESPN | GGACGCAAUUCCAGAGGUGAUGGG | CGGCGACGCAATTCCAGAGGTGATGGGGAGTGATTGTC | 115, 116 |
| N-TS11 | SMARCB1 | GUUCCAGUUGGGAAGGGCCAGUGC | TAGATTCCAGTTGGGAAGGGCCAGTGCCTCTGATTCCA | 117, 118 |
| N-TS25 | AC193513 | GGUUUCUCAUCCUGUCUUCUGCCU | CCGCGTTTCTCATCCTGTCTTCTGCCTAGTGGATATGT | 119, 120 |
| Nme-DTS3 | ARHGEF9 | GACUGAAGGCGAGGUCCGGGGCGG | GACTGAAGGCGAGGTCCGGGGCGGAGGGGATTGGG | 121, 122 |
| Spy-DTS3 | ARHGEF9 | GAAGGCGAGGUCCGGGGCGG | GACTGAAGGCGAGGTCCGGGGCGGAGGGGATTGGG | 123, 124 |
| Nme-DTS7 | LSP1 | GGCUGGCACCCUCCAUGUACCCAG | GGCTGGCACCCTCCATGTACCCAGGGGAGATTCCA | 125, 126 |
| Spy-DTS7 | LSP1 | GGCACCCUCCAUGUACCCAG | GGCTGGCACCCTCCATGTACCCAGGGGAGATTCCA | 127, 128 |

FIG. 25B

DIC + mTagBFP2 Overlay
dNmeCas9-(sfGFP)3
dSpyCas9-(mCherry)3
Merge

No Nme sgRNA

No Acr

AcrE2

AcrIIC4Hpa

AcrIIC5Smu

SEQUENCE LISTING

```
Sequence total quantity: 128
SEQ ID NO: 1            moltype = DNA  length = 276
FEATURE                 Location/Qualifiers
source                  1..276
                        mol_type = genomic DNA
                        organism = Brackiella oedipodis
SEQUENCE: 1
atgaaagagg tatttaaatt aaaaccagag ctagtgactt ataaaggttg cggctgggca  60
ctggcgtgca tcaaagacgg agagatcatc gatctcacct acgttcgtga ccttggtatt  120
gaagaatatg atgaaaactt cgatggcctt gaacctgaaa tcatctatta cgatgttgtg  180
gcttctcaag cgtgcaaaga agtcgcctat cgttatgaag aaatgggcga atttaccttc  240
ggcttatgct cgtgttggga attcaatgta atgtag                            276

SEQ ID NO: 2            moltype = AA  length = 91
FEATURE                 Location/Qualifiers
source                  1..91
                        mol_type = protein
                        organism = Brackiella oedipodis
SEQUENCE: 2
MKEVFKLKPE LVTYKGCGWA LACIKDGEII DLTYVRDLGI EEYDENFDGL EPEIIYYDVV  60
ASQACKEVAY RYEEMGEFTF GLCSCWEFNV M                                 91

SEQ ID NO: 3            moltype = DNA  length = 258
FEATURE                 Location/Qualifiers
source                  1..258
                        mol_type = genomic DNA
                        organism = Neisseria meningitidis
SEQUENCE: 3
atgaataaaa cttataaaat tggaaaaaat gccgggtatg atggctgcgg tctttgtctt  60
gcggccattt ctgaaaatga agctatcaaa gttaagtatt tgcgcgacat ttgtcctgat  120
tacgatggcg atgataaagc tgaggattgg ctgagatggg gaacggacag ccgcgtcaaa  180
gcagccgctc ttgaaatgga gcagtacgca tatacgtcgg ttggtatggc ctcatgttgg  240
gagtttgttg aactatga                                                258

SEQ ID NO: 4            moltype = AA  length = 85
FEATURE                 Location/Qualifiers
source                  1..85
                        mol_type = protein
                        organism = Neisseria meningitidis
SEQUENCE: 4
MNKTYKIGKN AGYDGCGLCL AAISENEAIK VKYLRDICPD YDGDDKAEDW LRWGTDSRVK  60
AAALEMEQYA YTSVGMASCW EFVEL                                        85

SEQ ID NO: 5            moltype = DNA  length = 372
FEATURE                 Location/Qualifiers
source                  1..372
                        mol_type = genomic DNA
                        organism = Neisseria meningitidis
SEQUENCE: 5
atgagcaaaa acaatatttt caacaagtat ccaacaatta ttcacggcga agcgcggggg  60
gagaatgacg aatttgtggt gcatacgcgc tacccgcgat tcttggcgcg gaaatctttt  120
```

-continued

```
gacgacaatt tcacgggcga aatgcctgca aaacctgtta acggggaatt gggacaaatc  180
ggcgaaccgc gccgccttgc ttatgattca cggcttggtt tgtggctttc tgacttcatc  240
atgttggaca acaacaagcc gaaaaacatg gaggattggc ttgggcaatt aaaagccgcc  300
tgcgatcgaa tcgcggcgga tgatttgatg ctgaatgaag atgcggcgga tttggagggc  360
tgggatgatt ga                                                       372

SEQ ID NO: 6           moltype = AA  length = 123
FEATURE                Location/Qualifiers
source                 1..123
                       mol_type = protein
                       organism = Neisseria meningitidis
SEQUENCE: 6
MSKNNIFNKY PTIIHGEARG ENDEFVVHTR YPRFLARKSF DDNFTGEMPA KPVNGELGQI  60
GEPRRLAYDS RLGLWLSDFI MLDNNKPKNM EDWLGQLKAA CDRIAADDLM LNEDAADLEG  120
WDD                                                                 123

SEQ ID NO: 7           moltype = DNA  length = 351
FEATURE                Location/Qualifiers
source                 1..351
                       mol_type = genomic DNA
                       organism = Neisseria meningitidis
SEQUENCE: 7
atgttcaaac gcgctattat cttcacttct ttcaacggct ttgaaaaagt ttctcgaact  60
gaaaaacgcc gccttgccaa aatcatcaat gctcgagttt ccatcatcga cgaatacttg  120
agagccaaag acaccaacgc atcgcttgac ggtcagtacc gcgctttctt gttcaacgac  180
gaatcgcccg caatgaccga atttctggca aaacttaaag cctttgccga aagttgcacc  240
ggaatcagca tcgacgcatg ggaaattgaa gaaagcgaat acgtccgcct gccggtggaa  300
cgcagggatt tcttagcggc agccaacggc aaagagattt ttaaaattta a           351

SEQ ID NO: 8           moltype = AA  length = 116
FEATURE                Location/Qualifiers
source                 1..116
                       mol_type = protein
                       organism = Neisseria meningitidis
SEQUENCE: 8
MFKRAIIFTS FNGFEKVSRT EKRRLAKIIN ARVSIIDEYL RAKDTNASLD GQYRAFLFND  60
ESPAMTEFLA KLKAFAESCT GISIDAWEIE ESEYVRLPVE RRDFLAAANG KEIFKI       116

SEQ ID NO: 9           moltype = DNA  length = 267
FEATURE                Location/Qualifiers
source                 1..267
                       mol_type = genomic DNA
                       organism = Neisseria meningitidis
SEQUENCE: 9
atggcaaaag gtagaacaag cattacagag cggctcaaaa agagccaaaa acgagaggcg  60
cgccgtgata tggcgcacga atgggcggaa aaatgggagc aggattattt gagcctgctc  120
tctcaaatca aacaggcaat cagcaaagga cacgatgacg agcttatcga cttatttgct  180
gatttacgcg cgctgcaaca gccaaaattt gaggcattgc atcgagtgat tgatgagctt  240
atcacgccga cacgggagct tatatga                                      267

SEQ ID NO: 10          moltype = AA  length = 88
FEATURE                Location/Qualifiers
source                 1..88
                       mol_type = protein
                       organism = Neisseria meningitidis
SEQUENCE: 10
MAKGRTSITE RLKKSQKREA RRDMAHEWAE KWEQDYLSLL SQIKQAISKG HDDELIDLFA  60
DLRALQQPKF EALHRVIDEL ITPTRELI                                     88

SEQ ID NO: 11          moltype = DNA  length = 192
FEATURE                Location/Qualifiers
source                 1..192
                       mol_type = genomic DNA
                       organism = Neisseria meningitidis
SEQUENCE: 11
atgaaatacg ccaaatcaaa atctatcagc aaaatcggtc aatatcatca aacttttaaa  60
atcctttggg ataaactacc aaaagaattg attgagaaat caacagccaa aaatctcgcc  120
attattattg atttgatgta tgagcaaaaa gaatatggcc atacagaggc atggcgcgaa  180
ttaacatcat aa                                                       192

SEQ ID NO: 12          moltype = AA  length = 63
FEATURE                Location/Qualifiers
source                 1..63
                       mol_type = protein
                       organism = Neisseria meningitidis
SEQUENCE: 12
MKYAKSKSIS KIGQYHQTFK ILWDKLPKEL IEKSTAKNLA IIIDLMYEQK EYGHTEAWRE  60
LTS                                                                 63
```

```
SEQ ID NO: 13          moltype = DNA  length = 312
FEATURE                Location/Qualifiers
source                 1..312
                       mol_type = genomic DNA
                       organism = Ralstonia solanacearum
SEQUENCE: 13
atgtacgcaa tctacacgga cgcaggaatc ctggcagtag cccccactgt ggaggcagcg  60
atcgaacggg ccaggtgcga gcatgggcta aaagccgctc ttgtggctca gaacacgagc  120
tgcatctacc acggcgggat cgttgatttg accactgcat ggcgaatctc tgccgattca  180
gagcgagccg gagattcgga gacgaaattg cgccgctgct cggcgcgctt ggcggcagca  240
gtagaggctg ggcgacttcc cgtgttcgct gtgatggcgc atggcgagtt agatctaatc  300
gaggatgcct ga                                                      312

SEQ ID NO: 14          moltype = AA  length = 103
FEATURE                Location/Qualifiers
source                 1..103
                       mol_type = protein
                       organism = Ralstonia solanacearum
SEQUENCE: 14
MYAIYTDAGI LAVAPTVEAA IERARCEHGL KAALVAQNTS CIYHGGIVDL TTAWRISADS  60
ERAGDSETKL RRCSARLAAA VEAGRLPVFA VMAHGELDLI EDA                    103

SEQ ID NO: 15          moltype = DNA  length = 261
FEATURE                Location/Qualifiers
source                 1..261
                       mol_type = genomic DNA
                       organism = Pseudomonas aeruginosa
SEQUENCE: 15
atgctggagc gatgcctcca gattgtcacc acgccgggcg ctgtgccccg agatcaggcg  60
gaggccaacg tttgccgttt ggccgggatg atcgtggacg gcaggtatcc agtggcaggc  120
aaacgactgt ctgatgcggc tgcgacctac tttgccgacc atccagagca gcaagtgccg  180
tccgccgagg tcgcccggcg cggctggatc ataaacgccc cacgcctccg gacgcgactg  240
gagcgcctgc tgggcgggta a                                            261

SEQ ID NO: 16          moltype = AA  length = 86
FEATURE                Location/Qualifiers
source                 1..86
                       mol_type = protein
                       organism = Pseudomonas aeruginosa
SEQUENCE: 16
MLERCLQIVT TPGAVPRDQA EANVCRLAGM IVDGRYPVAG KRLSDAAATY FADHPEQQVP  60
SAEVARRGWI INAPRLRTRL ERLLGG                                       86

SEQ ID NO: 17          moltype = DNA  length = 400
FEATURE                Location/Qualifiers
misc_feature           1..400
                       note = Synthetic
source                 1..400
                       mol_type = other DNA
                       organism = synthetic construct
SEQUENCE: 17
catttcttta tatgtcttaa tgctgacctt ctgcacaaat gcaccactat accattacca  60
gttattacca gctaataggg tgggagctaa tgaacactta caactctgtc ctcaggaaag  120
tgcagagaaa ttcatgcatc ccaggagggg atgctcagaa agaggaagct ggtttatgat  180
tggactgcgt gggcgtttgc aaagcaaggt ttcattgaaa agagatgttt tcttgtgggg  240
catttgagtc aattaccaaa gtctattttt aaaacttctc catatgagcc tgatctatct  300
ctgaagttgt tttgaagacc acaggactgc ttgtaacatg tgccattgcc attctgcttt  360
ttattctttt gattggaagg actaaaatga ttttcactta                        400

SEQ ID NO: 18          moltype = DNA  length = 402
FEATURE                Location/Qualifiers
misc_feature           1..402
                       note = Synthetic
source                 1..402
                       mol_type = other DNA
                       organism = synthetic construct
SEQUENCE: 18
ggacagaaga gagtagggag acgagaaggc ggaggacaga agaaatgggg gagagggaag  60
aggacagaga ggctgcgcgc ctctgaatac gccaagtcca gcagagctgg aggcctgtga  120
gaggagctgc aagcttgagc aaagggagag aggtgagcgg atgaagggag attggtgagt  180
atccgcccac gcacctactt gtaaaaagat caaggggaaa cacgcagaag gtcccgcggg  240
agtcctgtga cccacgtgag gtgctcgtgc cagcgcgggg tgggaggtgg tgggcaatgt  300
tcgtcgtgga gttgaggaag aaattctcca gccttaagga agcaaaagag ttcaaagatc  360
agtgaggctg ctcaacagag ggatatgcag atgacagaat gc                     402

SEQ ID NO: 19          moltype = DNA  length = 428
FEATURE                Location/Qualifiers
misc_feature           1..428
                       note = Synthetic
```

```
source                1..428
                      mol_type = other DNA
                      organism = synthetic construct
SEQUENCE: 19
gcaatccacc caatgctaac tggggatgttt gattttgcag cctctttcag agcagttgct  60
aaaagtggct ccacatcata agagggcttc cctccctcaa tccatgagag caactaggtt  120
ttgcatcagt gaaaggaaga aaaagcagga gtttggcaag aggctgcaaa gagacggcac  180
tgggctccac tagagttcct tcccaccgcg tttctcatcc tgtcttctgc ctagtggata  240
tgtctgcgtg ggcgtgcaca cacattggct gatgaaaccc ccttcctgtt gcacagggtc  300
agaactaagc gaggtgggtg tagctttgga gggttctgaa atctaagaac cagcttcctt  360
tcccaccgct ttccgctgag tcagttcact gcagagtgct ctgcaggatc tggaggcctt  420
tgtgttca                                                          428

SEQ ID NO: 20         moltype = DNA  length = 476
FEATURE               Location/Qualifiers
misc_feature          1..476
                      note = Synthetic
source                1..476
                      mol_type = other DNA
                      organism = synthetic construct
SEQUENCE: 20
ggacaaaagc agcccattag gacccccccca cactcgcacc tctccctgcc aagacctcta  60
ggagcagcag ggcggagaga cagagcctgc cggttggcat ggaacaaact gactgaaggc  120
gaggtccggg gcggaggga ttgggttgta gggctgtgga ggaggggcgg cggaggggggc  180
gctggggctc tcgcttgctt cagcccagcc cttctagtca gcccgcgaca actcgcgcca  240
gctacggggc ctcagagaag ccggacttcg caagcaccat gcagtggata aggggcggat  300
cgggaatggt gagtgcatgt aaccttggct tcccttgctt gagcctctca gtcccccagc  360
cccacctcca gttcctccaa cgagccacaa ggcagtgagc accctggcct ctgcccaccg  420
ccctagccgc cgtccttgag acaccagtga gcttgctgtg gccattttag gagtcc      476

SEQ ID NO: 21         moltype = DNA  length = 540
FEATURE               Location/Qualifiers
misc_feature          1..540
                      note = Synthetic
source                1..540
                      mol_type = other DNA
                      organism = synthetic construct
SEQUENCE: 21
aggactgctc tcagctaccg gcctcctctg gatgacggga ctgcaggaac cacgagaacc  60
ccagttctag ctcccggggt gggcaggctg cttggcaggc aggccgcctt ccctccacca  120
ggagtcaggt ctccagccag aggtcctgac ccagggcaca agtgctcgca ctgggaagca  180
ggcctctgag gcaggacgtc ttctcctgtg gtggagtggg ggtgtgggca gggcagggag  240
gccagcagag agaggctcgg ggagcaggct ctgtgggctt gcaggaggca ggtctgtggc  300
ccctccctgg accctagcct aatgccccct gcaccccatg cctatgttcc agcttcctgg  360
gtctgcaggt ccagccggct ggcaccctcc atgtacccag gggagattcc agccagacac  420
ccgccccccg gccctggcta agaagttgct tcctgttgcc agcatgacct accctcgcct  480
ctttgatgcc atccgctgcc acctcctttt gctcctggac cctttagcct ctctgccctt  540

SEQ ID NO: 22         moltype = DNA  length = 267
FEATURE               Location/Qualifiers
source                1..267
                      mol_type = genomic DNA
                      organism = Haemophilus parainfluenzae
SEQUENCE: 22
atgaagatca ccagcagcaa cttcgcgacc attgcgacca gcgagaactt tgcgaagctg  60
agcgtgctgc cgaaaaacca ccgtgagccg atcaagggtc tgttcaaaag cgcggttgaa  120
cagtttagca gcgcgcgtga cttctttaag aacgagaact acagcaaaga gctggcggaa  180
aagttcaaca aagaagcggt gaacgaggcg gttgaaaagc tgcaaaaagc gatcgatctg  240
gcggaaaaac agggcattca attttga                                     267

SEQ ID NO: 23         moltype = AA  length = 88
FEATURE               Location/Qualifiers
source                1..88
                      mol_type = protein
                      organism = Haemophilus parainfluenzae
SEQUENCE: 23
MKITSSNFAT IATSENFAKL SVLPKNHREP IKGLFKSAVE QFSSARDFFK NENYSKELAE  60
KFNKEAVNEA VEKLQKAIDL AEKQGIQF                                    88

SEQ ID NO: 24         moltype = DNA  length = 393
FEATURE               Location/Qualifiers
source                1..393
                      mol_type = genomic DNA
                      organism = Simonsiella muelleri
SEQUENCE: 24
atgaacaaca gcatcaagtt ccacgtgagc tacgacggta ccgcgcgtgc gctgtttaac  60
accaaggagc aggcggaaaa atactgcctg gttgaggaaa ttaacgatga gatgaacggc  120
tataagcgta aaagctggga ggaaaagctg cgtgaggaaa actgcgcgag cgtgcaggac  180
tgggttgaga agaactacac cagcagctat agcgacctgt tcaacatctg cgagattgaa  240
```

```
gtgagcagcg cgggtcaact ggttaagatc gacaacaccg aggtggacga tttcgttgaa  300
aactgctatg gctttaccct ggaggacgat ctggaggaat tcaacaaggc gaaacagtac  360
ctgcaaaaat tttatgcgga gtgcgaaaac tga                                393

SEQ ID NO: 25          moltype = AA  length = 130
FEATURE                Location/Qualifiers
source                 1..130
                       mol_type = protein
                       organism = Simonsiella muelleri
SEQUENCE: 25
MNNSIKFHVS YDGTARALFN TKEQAEKYCL VEEINDEMNG YKRKSWEEKL REENCASVQD  60
WVEKNYTSSY SDLFNICEIE VSSAGQLVKI DNTEVDDFVE NCYGFTLEDD LEEFNKAKQY  120
LQKFYAECEN                                                          130

SEQ ID NO: 26          moltype = DNA  length = 279
FEATURE                Location/Qualifiers
misc_feature           1..279
                       note = Synthetic
source                 1..279
                       mol_type = other DNA
                       organism = synthetic construct
SEQUENCE: 26
atggccaagg aggtcttcaa gctgaagccg gagctggtga cgtacaaggg ctgcgggtgg  60
gccctggcct gcatcaagga tggcgagatc atcgacctga cctacgtgcg tgacctgggc  120
atcgaggagt acgatgaaaa cttcgacggc ctggagccgg agatcatcta ttacgacgtc  180
gtcgcctcgc aggcgtgcaa ggaagtggcc taccgctatg aagagatggg cgaattcacc  240
ttcggcctct gcagctgctg ggaattcaac gtcatgtaa                          279

SEQ ID NO: 27          moltype = AA  length = 92
FEATURE                Location/Qualifiers
REGION                 1..92
                       note = Synthetic
source                 1..92
                       mol_type = protein
                       organism = synthetic construct
SEQUENCE: 27
MAKEVFKLKP ELVTYKGCGW ALACIKDGEI IDLTYVRDLG IEEYDENFDG LEPEIIYYDV  60
VASQACKEVA YRYEEMGEFT FGLCSCWEFN VM                                 92

SEQ ID NO: 28          moltype = DNA  length = 261
FEATURE                Location/Qualifiers
misc_feature           1..261
                       note = Synthetic
source                 1..261
                       mol_type = other DNA
                       organism = synthetic construct
SEQUENCE: 28
atggccaata aaacttataa aattggaaaa aatgccgggt atgatggctg cggtctttgt  60
cttgcggcca tttctgaaaa tgaagctatc aaagttaagt atttgcgcga catttgtcct  120
gattacgatg gcgatgataa agctgaggat tggctgagat ggggaacgga cagccgcgtc  180
aaagcagccg ctcttgaaat ggagcagtac gcatatacgt cggttggtat ggcctcatgt  240
tgggagtttg ttgaactatg a                                             261

SEQ ID NO: 29          moltype = AA  length = 86
FEATURE                Location/Qualifiers
REGION                 1..86
                       note = Synthetic
source                 1..86
                       mol_type = protein
                       organism = synthetic construct
SEQUENCE: 29
MANKTYKIGK NAGYDGCGLC LAAISENEAI KVKYLRDICP DYDGDDKAED WLRWGTDSRV  60
KAAALEMEQY AYTSVGMASC WEFVEL                                        86

SEQ ID NO: 30          moltype = DNA  length = 375
FEATURE                Location/Qualifiers
misc_feature           1..375
                       note = Synthetic
source                 1..375
                       mol_type = other DNA
                       organism = synthetic construct
SEQUENCE: 30
atggccagca aaaacaatat tttcaacaag tatccaacaa ttattcacgg cgaagcgcgg  60
ggggagaatg acgaatttgt ggtgcatacg cgctacccgc gattcttggc gcggaaatct  120
tttgacgaca atttcacggg cgaaatgcct gcaaaacctg ttaacgggga attgggacaa  180
atcggcgaac cgcgccgcct tgcttatgat tcacggcttg gtttgtggct ttctgacttc  240
atcatgttgg acaacaacaa gccgaaaaac atggaggatt ggcttgggca attaaaagcc  300
gcctgcgatc gaatcgcggc ggatgatttg atgctgaatg aagatgcggc ggatttggag  360
ggctgggatg attga                                                    375
```

```
SEQ ID NO: 31          moltype = AA  length = 124
FEATURE                Location/Qualifiers
REGION                 1..124
                       note = Synthetic
source                 1..124
                       mol_type = protein
                       organism = synthetic construct
SEQUENCE: 31
MASKNNIFNK YPTIIHGEAR GENDEFVVHT RYPRFLARKS FDDNFTGEMP AKPVNGELGQ  60
IGEPRRLAYD SRLGLWLSDF IMLDNNKPKN MEDWLGQLKA ACDRIAADDL MLNEDAADLE  120
GWDD                                                               124

SEQ ID NO: 32          moltype = DNA  length = 354
FEATURE                Location/Qualifiers
misc_feature           1..354
                       note = Synthetic
source                 1..354
                       mol_type = other DNA
                       organism = synthetic construct
SEQUENCE: 32
atggccttca aacgcgctat tatcttcact tctttcaacg gctttgaaaa agtttctcga  60
actgaaaaac gccgccttgc caaaatcatc aatgctcgag tttccatcat cgacgaatac  120
ttgagagcca aagacaccaa cgcatcgctt gacggtcagt accgcgcttt cttgttcaac  180
gacgaatcgc ccgcaatgac cgaatttctg gcaaaactta aagcctttgc cgaaagttgc  240
accggaatca gcatcgacgc atgggaaatt gaagaaagcg aatacgtccg cctgccggtg  300
gaacgcaggg atttcttagc ggcagccaac ggcaaagaga tttttaaaat ttaa        354

SEQ ID NO: 33          moltype = AA  length = 117
FEATURE                Location/Qualifiers
REGION                 1..117
                       note = Synthetic
source                 1..117
                       mol_type = protein
                       organism = synthetic construct
SEQUENCE: 33
MAFKRAIIFT SFNGFEKVSR TEKRRLAKII NARVSIIDEY LRAKDTNASL DGQYRAFLFN  60
DESPAMTEFL AKLKAFAESC TGISIDAWEI EESEYVRLPV ERRDFLAAAN GKEIFKI     117

SEQ ID NO: 34          moltype = DNA  length = 258
FEATURE                Location/Qualifiers
misc_feature           1..258
                       note = Synthetic
source                 1..258
                       mol_type = other DNA
                       organism = synthetic construct
SEQUENCE: 34
atggccaata cctatctcat cgacccccgc aaaaacaacg acaactccgg cgagcgcttc  60
acggttgacg ctgtcgacat tacagccgcc gcgaagagcg cagcccaaca gattcttggc  120
gaggaattcg agggcctcgt ataccgtgaa accggggaga gtaacggaag tggcatgttc  180
caggcctacc accacctgca cggcactaac cgcacggaga cgaccgttgg ctatccgttt  240
catgtaatgg aactctga                                                258

SEQ ID NO: 35          moltype = AA  length = 85
FEATURE                Location/Qualifiers
REGION                 1..85
                       note = Synthetic
source                 1..85
                       mol_type = protein
                       organism = synthetic construct
SEQUENCE: 35
MANTYLIDPR KNNDNSGERF TVDAVDITAA AKSAAQQILG EEFEGLVYRE TGESNGSGMF  60
QAYHHLHGTN RTETTVGYPF HVMEL                                        85

SEQ ID NO: 36          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 36
gcacttattc tggcccctga ctgc                                         24

SEQ ID NO: 37          moltype = DNA  length = 27
FEATURE                Location/Qualifiers
misc_feature           1..27
                       note = Synthetic
source                 1..27
```

```
                        mol_type = other DNA
                        organism = synthetic construct
SEQUENCE: 37
gagaaccatg gtctggggaa gaagacc                                         27

SEQ ID NO: 38           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 38
caccgtggtc tggggtacag ccttggca                                        28

SEQ ID NO: 39           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 39
caactgccaa ggctgtaccc cagaccac                                        28

SEQ ID NO: 40           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 40
gtggtctggg gtacagcctt ggca                                            24

SEQ ID NO: 41           moltype = DNA  length = 25
FEATURE                 Location/Qualifiers
misc_feature            1..25
                        note = Synthetic
source                  1..25
                        mol_type = other DNA
                        organism = synthetic construct
SEQUENCE: 41
agaggagcct tctgactgct gcaga                                           25

SEQ ID NO: 42           moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 42
aggtcctggc cttgccttcg a                                               21

SEQ ID NO: 43           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 43
caccggacag gagtcgccag aggccggt                                        28

SEQ ID NO: 44           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 44
caacaccggc ctctggcgac tcctgtcc                                        28

SEQ ID NO: 45           moltype = DNA  length = 24
FEATURE                 Location/Qualifiers
misc_feature            1..24
                        note = Synthetic
```

```
source                  1..24
                        mol_type = other DNA
                        organism = synthetic construct
SEQUENCE: 45
ggacaggagt cgccagaggc cggt                                              24

SEQ ID NO: 46           moltype = DNA  length = 25
FEATURE                 Location/Qualifiers
misc_feature            1..25
                        note = Synthetic
source                  1..25
                        mol_type = other DNA
                        organism = synthetic construct
SEQUENCE: 46
agaggagcct tctgactgct gcaga                                             25

SEQ ID NO: 47           moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 47
aggtcctggc cttgccttcg a                                                 21

SEQ ID NO: 48           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 48
caccggggct ggctccacgt cgcgccgc                                          28

SEQ ID NO: 49           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 49
caacgcggcg cgacgtggag ccagcccc                                          28

SEQ ID NO: 50           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 50
ggggctggct ccacgtcgcg ccgc                                              24

SEQ ID NO: 51           moltype = DNA  length = 25
FEATURE                 Location/Qualifiers
misc_feature            1..25
                        note = Synthetic
source                  1..25
                        mol_type = other DNA
                        organism = synthetic construct
SEQUENCE: 51
ggacagaaga gagtagggag acgag                                             25

SEQ ID NO: 52           moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 52
gcattctgtc atctgcatat ccctctg                                           27

SEQ ID NO: 53           moltype = DNA  length = 28
FEATURE                 Location/Qualifiers
misc_feature            1..28
```

```
                        note = Synthetic
source                  1..28
                        mol_type = other DNA
                        organism = synthetic construct
SEQUENCE: 53
caccgaggga gagaggtgag cggatgaa                                        28

SEQ ID NO: 54           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 54
caacttcatc cgctcacctc tctccctc                                        28

SEQ ID NO: 55           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 55
gagggagaga ggtgagcgga tgaa                                            24

SEQ ID NO: 56           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 56
tgcctcacgt aacagttgag accc                                            24

SEQ ID NO: 57           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 57
tgccctcccc gctggaacct                                                 20

SEQ ID NO: 58           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 58
caccggacgc aattccagag gtgatggg                                        28

SEQ ID NO: 59           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 59
caaccccatc acctctggaa ttgcgtcc                                        28

SEQ ID NO: 60           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 60
ggacgcaatt ccagaggtga tggg                                            24

SEQ ID NO: 61           moltype = DNA  length = 23
FEATURE                 Location/Qualifiers
```

```
misc_feature          1..23
                      note = Synthetic
source                1..23
                      mol_type = other DNA
                      organism = synthetic construct
SEQUENCE: 61
acaggcaact ccatccatga gcc                                             23

SEQ ID NO: 62         moltype = DNA  length = 24
FEATURE               Location/Qualifiers
misc_feature          1..24
                      note = Synthetic
source                1..24
                      mol_type = other DNA
                      organism = synthetic construct
SEQUENCE: 62
cttcacagca cttaggactg tctg                                            24

SEQ ID NO: 63         moltype = DNA  length = 28
FEATURE               Location/Qualifiers
misc_feature          1..28
                      note = Synthetic
source                1..28
                      mol_type = other DNA
                      organism = synthetic construct
SEQUENCE: 63
caccgttcca gttgggaagg gccagtgc                                        28

SEQ ID NO: 64         moltype = DNA  length = 28
FEATURE               Location/Qualifiers
misc_feature          1..28
                      note = Synthetic
source                1..28
                      mol_type = other DNA
                      organism = synthetic construct
SEQUENCE: 64
caacgcactg gcccttccca actggaac                                        28

SEQ ID NO: 65         moltype = DNA  length = 24
FEATURE               Location/Qualifiers
misc_feature          1..24
                      note = Synthetic
source                1..24
                      mol_type = other DNA
                      organism = synthetic construct
SEQUENCE: 65
gttccagttg ggaagggcca gtgc                                            24

SEQ ID NO: 66         moltype = DNA  length = 23
FEATURE               Location/Qualifiers
misc_feature          1..23
                      note = Synthetic
source                1..23
                      mol_type = other DNA
                      organism = synthetic construct
SEQUENCE: 66
gcaatccacc caatgctaac tgg                                             23

SEQ ID NO: 67         moltype = DNA  length = 23
FEATURE               Location/Qualifiers
misc_feature          1..23
                      note = Synthetic
source                1..23
                      mol_type = other DNA
                      organism = synthetic construct
SEQUENCE: 67
tgaacacaaa ggcctccaga tcc                                             23

SEQ ID NO: 68         moltype = DNA  length = 28
FEATURE               Location/Qualifiers
misc_feature          1..28
                      note = Synthetic
source                1..28
                      mol_type = other DNA
                      organism = synthetic construct
SEQUENCE: 68
caccggtttc tcatcctgtc ttctgcct                                        28

SEQ ID NO: 69         moltype = DNA  length = 28
```

```
FEATURE                 Location/Qualifiers
misc_feature            1..28
                        note = Synthetic
source                  1..28
                        mol_type = other DNA
                        organism = synthetic construct
SEQUENCE: 69
caacaggcag aagacaggat gagaaacc                                      28

SEQ ID NO: 70           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 70
ggtttctcat cctgtcttct gcct                                          24

SEQ ID NO: 71           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 71
ggacaaaagc agcccattag                                               20

SEQ ID NO: 72           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 72
ggactcctaa aatggccaca                                               20

SEQ ID NO: 73           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 73
caccgactga aggcgaggtc cggggcgg                                      28

SEQ ID NO: 74           moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 74
caacccgccc cggacctcgc cttcagtc                                      28

SEQ ID NO: 75           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 75
gactgaaggc gaggtccggg gcgg                                          24

SEQ ID NO: 76           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 76
ggacaaaagc agcccattag                                               20
```

```
SEQ ID NO: 77          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 77
ggactcctaa aatggccaca                                              20

SEQ ID NO: 78          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 78
accggaaggc gaggtccggg gcgg                                         24

SEQ ID NO: 79          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 79
aaacccgccc cggacctcgc cttc                                         24

SEQ ID NO: 80          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 80
gaaggcgagg tccggggcgg                                              20

SEQ ID NO: 81          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 81
aggactgctc tcagctaccg                                              20

SEQ ID NO: 82          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 82
aagggcagag aggctaaagg                                              20

SEQ ID NO: 83          moltype = DNA  length = 28
FEATURE                Location/Qualifiers
misc_feature           1..28
                       note = Synthetic
source                 1..28
                       mol_type = other DNA
                       organism = synthetic construct
SEQUENCE: 83
caccggctgg caccctccat gtacccag                                     28

SEQ ID NO: 84          moltype = DNA  length = 28
FEATURE                Location/Qualifiers
misc_feature           1..28
                       note = Synthetic
source                 1..28
                       mol_type = other DNA
                       organism = synthetic construct
SEQUENCE: 84
caacctgggt acatggaggg tgccagcc                                     28
```

```
SEQ ID NO: 85          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 85
ggctggcacc ctccatgtac ccag                                        24

SEQ ID NO: 86          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 86
aggactgctc tcagctaccg                                             20

SEQ ID NO: 87          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 87
aagggcagag aggctaaagg                                             20

SEQ ID NO: 88          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 88
accgggcacc ctccatgtac ccag                                        24

SEQ ID NO: 89          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 89
aaacctgggt acatggaggg tgcc                                        24

SEQ ID NO: 90          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 90
ggcaccctcc atgtacccag                                             20

SEQ ID NO: 91          moltype = DNA  length = 28
FEATURE                Location/Qualifiers
misc_feature           1..28
                       note = Synthetic
source                 1..28
                       mol_type = other DNA
                       organism = synthetic construct
SEQUENCE: 91
accgttaggg ttagggttag ggttaggg                                    28

SEQ ID NO: 92          moltype = DNA  length = 28
FEATURE                Location/Qualifiers
misc_feature           1..28
                       note = Synthetic
source                 1..28
                       mol_type = other DNA
                       organism = synthetic construct
SEQUENCE: 92
```

```
caacccctaa ccctaaccct aaccctaa                                  28

SEQ ID NO: 93           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 93
ttagggttag ggttagggtt aggg                                      24

SEQ ID NO: 94           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 94
accgttaggg ttagggttag ggtt                                      24

SEQ ID NO: 95           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 95
aaacaaccct aaccctaacc ctaa                                      24

SEQ ID NO: 96           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 96
ttagggttag ggttagggtt                                           20

SEQ ID NO: 97           moltype = DNA  length = 171
FEATURE                 Location/Qualifiers
misc_feature            1..171
                        note = Synthetic
source                  1..171
                        mol_type = other DNA
                        organism = synthetic construct
SEQUENCE: 97
tgagaccagt ctcggaagct caaaggtctc gttgtagctc cctttctcat ttcggaaacg  60
aaatgagaac cgttgctaca ataaggccgt ctgaaaagat gtgccgcaac gctctgcccc  120
ttaaagcttc tgctttaagg ggcatcgttt atttcggtta aaaaatgccg t           171

SEQ ID NO: 98           moltype = AA  length = 8
FEATURE                 Location/Qualifiers
REGION                  1..8
                        note = Synthetic
source                  1..8
                        mol_type = protein
                        organism = synthetic construct
SEQUENCE: 98
DYKDDDDK                                                        8

SEQ ID NO: 99           moltype = DNA  length = 38
FEATURE                 Location/Qualifiers
misc_feature            1..38
                        note = Synthetic
source                  1..38
                        mol_type = other DNA
                        organism = synthetic construct
SEQUENCE: 99
aactgactga aggcgaggtc cggggcggag gggattgg                       38

SEQ ID NO: 100          moltype = DNA  length = 39
FEATURE                 Location/Qualifiers
misc_feature            1..39
                        note = Synthetic
source                  1..39
```

```
                        mol_type = other DNA
                        organism = synthetic construct
SEQUENCE: 100
ccaatcccct ccgccccgga cctcgccttc agtcagttt                          39

SEQ ID NO: 101          moltype = DNA  length = 29
FEATURE                 Location/Qualifiers
misc_feature            1..29
                        note = Synthetic
source                  1..29
                        mol_type = other DNA
                        organism = synthetic construct
modified_base           4
                        mod_base = OTHER
                        note = Uracil
modified_base           15
                        mod_base = OTHER
                        note = Uracil
modified_base           26
                        mod_base = OTHER
                        note = Uracil
modified_base           27
                        mod_base = OTHER
                        note = Uracil
modified_base           29
                        mod_base = OTHER
                        note = Uracil
SEQUENCE: 101
gactgaaggc gaggtccggg gcgggttgt                                     29

SEQ ID NO: 102          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 102
aaactgactg aaggcgaggt ccggggcgga ggggattgg                          39

SEQ ID NO: 103          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 103
ccaatcccct ccgccccgga cctcgccttc agtcagttt                          39

SEQ ID NO: 104          moltype = DNA  length = 25
FEATURE                 Location/Qualifiers
misc_feature            1..25
                        note = Synthetic
source                  1..25
                        mol_type = other DNA
                        organism = synthetic construct
modified_base           11
                        mod_base = OTHER
                        note = Uracil
modified_base           22
                        mod_base = OTHER
                        note = Uracil
modified_base           23
                        mod_base = OTHER
                        note = Uracil
modified_base           24
                        mod_base = OTHER
                        note = Uracil
SEQUENCE: 104
gaaggcgagg tccggggcgg gttta                                         25

SEQ ID NO: 105          moltype =   length =
SEQUENCE: 105
000

SEQ ID NO: 106          moltype =   length =
SEQUENCE: 106
000
```

```
SEQ ID NO: 107         moltype = DNA  length = 24
FEATURE                Location/Qualifiers
misc_feature           1..24
                       note = Synthetic
source                 1..24
                       mol_type = other DNA
                       organism = synthetic construct
modified_base          2
                       mod_base = OTHER
                       note = Uracil
modified_base          5
                       mod_base = OTHER
                       note = Uracil
modified_base          7
                       mod_base = OTHER
                       note = Uracil
modified_base          12
                       mod_base = OTHER
                       note = Uracil
modified_base          19
                       mod_base = OTHER
                       note = Uracil
modified_base          20
                       mod_base = OTHER
                       note = Uracil
SEQUENCE: 107
gtggtctggg gtacagcctt ggca                                        24

SEQ ID NO: 108         moltype = DNA  length = 38
FEATURE                Location/Qualifiers
misc_feature           1..38
                       note = Synthetic
source                 1..38
                       mol_type = other DNA
                       organism = synthetic construct
SEQUENCE: 108
tacttggtct ggggtacagc cttggcatca tgattttg                         38

SEQ ID NO: 109         moltype = DNA  length = 24
FEATURE                Location/Qualifiers
misc_feature           1..24
                       note = Synthetic
source                 1..24
                       mol_type = other DNA
                       organism = synthetic construct
modified_base          10
                       mod_base = OTHER
                       note = Uracil
modified_base          24
                       mod_base = OTHER
                       note = Uracil
SEQUENCE: 109
ggacaggagt cgccagaggc cggt                                        24

SEQ ID NO: 110         moltype = DNA  length = 38
FEATURE                Location/Qualifiers
misc_feature           1..38
                       note = Synthetic
source                 1..38
                       mol_type = other DNA
                       organism = synthetic construct
SEQUENCE: 110
gcaggacagg agtcgccaga ggccggtggt ggatttcc                         38

SEQ ID NO: 111         moltype = DNA  length = 24
FEATURE                Location/Qualifiers
misc_feature           1..24
                       note = Synthetic
source                 1..24
                       mol_type = other DNA
                       organism = synthetic construct
modified_base          6
                       mod_base = OTHER
                       note = Uracil
modified_base          10
                       mod_base = OTHER
                       note = Uracil
modified_base          16
```

```
                        mod_base = OTHER
                        note = Uracil
SEQUENCE: 111
ggggctggct ccacgtcgcg ccgc                                            24

SEQ ID NO: 112          moltype = DNA  length = 38
FEATURE                 Location/Qualifiers
misc_feature            1..38
                        note = Synthetic
source                  1..38
                        mol_type = other DNA
                        organism = synthetic construct
SEQUENCE: 112
tgcggggctg gctccacgtc gcgccgcggc ggtttggg                             38

SEQ ID NO: 113          moltype = DNA  length = 24
FEATURE                 Location/Qualifiers
misc_feature            1..24
                        note = Synthetic
source                  1..24
                        mol_type = other DNA
                        organism = synthetic construct
modified_base           13
                        mod_base = OTHER
                        note = Uracil
modified_base           21
                        mod_base = OTHER
                        note = Uracil
SEQUENCE: 113
gagggagaga ggtgagcgga tgaa                                            24

SEQ ID NO: 114          moltype = DNA  length = 38
FEATURE                 Location/Qualifiers
misc_feature            1..38
                        note = Synthetic
source                  1..38
                        mol_type = other DNA
                        organism = synthetic construct
SEQUENCE: 114
gcaaagggag agaggtgagc ggatgaaggg agattggt                             38

SEQ ID NO: 115          moltype = DNA  length = 24
FEATURE                 Location/Qualifiers
misc_feature            1..24
                        note = Synthetic
source                  1..24
                        mol_type = other DNA
                        organism = synthetic construct
modified_base           9
                        mod_base = OTHER
                        note = Uracil
modified_base           10
                        mod_base = OTHER
                        note = Uracil
modified_base           18
                        mod_base = OTHER
                        note = Uracil
modified_base           21
                        mod_base = OTHER
                        note = Uracil
SEQUENCE: 115
ggacgcaatt ccagaggtga tggg                                            24

SEQ ID NO: 116          moltype = DNA  length = 38
FEATURE                 Location/Qualifiers
misc_feature            1..38
                        note = Synthetic
source                  1..38
                        mol_type = other DNA
                        organism = synthetic construct
SEQUENCE: 116
cggcgacgca attccagagg tgatggggag tgattgtc                             38

SEQ ID NO: 117          moltype = DNA  length = 24
FEATURE                 Location/Qualifiers
misc_feature            1..24
                        note = Synthetic
source                  1..24
                        mol_type = other DNA
```

```
                        organism = synthetic construct
modified_base           2
                        mod_base = OTHER
                        note = Uracil
modified_base           3
                        mod_base = OTHER
                        note = Uracil
modified_base           8
                        mod_base = OTHER
                        note = Uracil
modified_base           9
                        mod_base = OTHER
                        note = Uracil
modified_base           22
                        mod_base = OTHER
                        note = Uracil
SEQUENCE: 117
gttccagttg ggaagggcca gtgc                                                24

SEQ ID NO: 118          moltype = DNA  length = 38
FEATURE                 Location/Qualifiers
misc_feature            1..38
                        note = Synthetic
source                  1..38
                        mol_type = other DNA
                        organism = synthetic construct
SEQUENCE: 118
tagattccag ttgggaaggg ccagtgcctc cgattcca                                 38

SEQ ID NO: 119          moltype = DNA  length = 24
FEATURE                 Location/Qualifiers
misc_feature            1..24
                        note = Synthetic
source                  1..24
                        mol_type = other DNA
                        organism = synthetic construct
modified_base           3
                        mod_base = OTHER
                        note = Uracil
modified_base           4
                        mod_base = OTHER
                        note = Uracil
modified_base           5
                        mod_base = OTHER
                        note = Uracil
modified_base           7
                        mod_base = OTHER
                        note = Uracil
modified_base           10
                        mod_base = OTHER
                        note = Uracil
modified_base           13
                        mod_base = OTHER
                        note = Uracil
modified_base           15
                        mod_base = OTHER
                        note = Uracil
modified_base           17
                        mod_base = OTHER
                        note = Uracil
modified_base           18
                        mod_base = OTHER
                        note = Uracil
modified_base           20
                        mod_base = OTHER
                        note = Uracil
modified_base           24
                        mod_base = OTHER
                        note = Uracil
SEQUENCE: 119
ggtttctcat cctgtcttct gcct                                                24

SEQ ID NO: 120          moltype = DNA  length = 38
FEATURE                 Location/Qualifiers
misc_feature            1..38
                        note = Synthetic
source                  1..38
                        mol_type = other DNA
                        organism = synthetic construct
```

```
SEQUENCE: 120
ccgcgtttct catcctgtct tctgcctagt ggatatgt                          38

SEQ ID NO: 121          moltype = DNA  length = 24
FEATURE                 Location/Qualifiers
misc_feature            1..24
                        note = Synthetic
source                  1..24
                        mol_type = other DNA
                        organism = synthetic construct
modified_base           4
                        mod_base = OTHER
                        note = Uracil
modified_base           15
                        mod_base = OTHER
                        note = Uracil
SEQUENCE: 121
gactgaaggc gaggtccggg gcgg                                         24

SEQ ID NO: 122          moltype = DNA  length = 35
FEATURE                 Location/Qualifiers
misc_feature            1..35
                        note = Synthetic
source                  1..35
                        mol_type = other DNA
                        organism = synthetic construct
SEQUENCE: 122
gactgaaggc gaggtccggg gcggagggga ttggg                             35

SEQ ID NO: 123          moltype = DNA  length = 20
FEATURE                 Location/Qualifiers
misc_feature            1..20
                        note = Synthetic
source                  1..20
                        mol_type = other DNA
                        organism = synthetic construct
modified_base           11
                        mod_base = OTHER
                        note = Uracil
SEQUENCE: 123
gaaggcgagg tccggggcgg                                              20

SEQ ID NO: 124          moltype = DNA  length = 35
FEATURE                 Location/Qualifiers
misc_feature            1..35
                        note = Synthetic
source                  1..35
                        mol_type = other DNA
                        organism = synthetic construct
SEQUENCE: 124
gactgaaggc gaggtccggg gcggagggga ttggg                             35

SEQ ID NO: 125          moltype = DNA  length = 24
FEATURE                 Location/Qualifiers
misc_feature            1..24
                        note = Synthetic
source                  1..24
                        mol_type = other DNA
                        organism = synthetic construct
modified_base           4
                        mod_base = OTHER
                        note = Uracil
modified_base           12
                        mod_base = OTHER
                        note = Uracil
modified_base           16
                        mod_base = OTHER
                        note = Uracil
modified_base           18
                        mod_base = OTHER
                        note = Uracil
SEQUENCE: 125
ggctggcacc ctccatgtac ccag                                         24

SEQ ID NO: 126          moltype = DNA  length = 36
FEATURE                 Location/Qualifiers
misc_feature            1..36
                        note = Synthetic
source                  1..36
```

-continued

```
                      mol_type = other DNA
                      organism = synthetic construct
SEQUENCE: 126
ggctggcacc ctccatgtac ccaaggggag attcca                            36

SEQ ID NO: 127        moltype = DNA  length = 20
FEATURE               Location/Qualifiers
misc_feature          1..20
                      note = Synthetic
source                1..20
                      mol_type = other DNA
                      organism = synthetic construct
modified_base         8
                      mod_base = OTHER
                      note = Uracil
modified_base         12
                      mod_base = OTHER
                      note = Uracil
modified_base         14
                      mod_base = OTHER
                      note = Uracil
SEQUENCE: 127
ggcaccctcc atgtacccag                                              20

SEQ ID NO: 128        moltype = DNA  length = 35
FEATURE               Location/Qualifiers
misc_feature          1..35
                      note = Synthetic
source                1..35
                      mol_type = other DNA
                      organism = synthetic construct
SEQUENCE: 128
ggctggcacc ctccatgtac ccaggggaga ttcca                             35
```

ANTI-CRISPR COMPOUNDS AND METHODS OF USE

CROSS REFERENCED APPLICATION

This application is a Continuation of, and claims priority to, co-pending U.S. patent application Ser. No. 16/084,397, filed Sep. 12, 2018, now Patent Registration Ser. No. 11,530,394, issued Dec. 20, 2022, which claims priority to PCT/US17/22040, filed Mar. 13, 2017, now expired; which claims priority to Provisional Application Serial Nos. 62/308,417, filed on Mar. 15, 2016, and 62/497,097, filed on Nov. 7, 2016, the contents of which are incorporated herein in their entirety.

STATEMENT OF GOVERNMENTAL SUPPORT

This invention was made with government support under grant no. GM115911 awarded by the National Institutes of Health. The government has certain rights in the invention.

REFERENCE TO AN ELECTRONIC SEQUENCE LISTING

The contents of the electronic listing: (20147revised.xml; 184 kilobytes; Date of Creation: Oct. 22, 2022) is herein incorporated by reference in its entirety.

FIELD OF THE INVENTION

The present invention is related to the field of CRISPR-Cas9 gene editing platforms. In particular, the present invention has identified Type II-C Cas9 anti-CRISPR (Acr) inhibitors that control Cas9 gene editing activity. Co-administration of such Acr inhibitors may provide an advantageous adjunct in permitting safe and practical biological therapeutics through spatial or temporal control of Cas9 activity; controlling Cas9-based gene drives in wild populations to reduce the ecological consequences of such forced inheritance schemes; and contributing to general research into various biotechnological, agricultural, and medical applications of gene editing technologies.

BACKGROUND

CRISPR-Cas9 (clustered regularly interspaced short palindromic repeats; CRISPR-associated system) comprises a bacterial immune system that recognizes and destroys foreign nucleic acids. The development of Type II CRISPR-Cas9 systems as programmable nucleases for genome engineering has been beneficial in the biomedical sciences. For example, a Cas9 platform has enabled gene editing in a large variety of biological systems, where both gene knockouts and tailor-made alterations are possible within complex genomes with unprecedented accuracy and efficiency. The CRISPR-Cas9 system has the potential for application to gene therapy approaches for disease treatment, whether for the creation of custom, genome-edited cell-based therapies or for direct correction or ablation of aberrant genomic loci within patients. Mutant versions of Cas9 in which the DNA cleavage activity has been inactivated ["dead" Cas9 (dCas9)] have also been developed for RNA-guided genome binding, enabling further applications in gene expression control and genome structure visualization.

The safe application of CRISPR-Cas9 in gene therapy requires an ability to control the gene editing activity of a Cas9/sgRNA complex once the intended use has been realized. While several engineered systems allow for controlled activation of CRISPR-Cas9 to increase precision, all of these systems still lack the ability to provide predictable control and robust inhibition.

What is needed in the art is the ability to predictably control gene editing (Cas9) or genome binding (dCas9) activity to prevent unintended Cas9 cleavage or DNA binding activity once a specific goal has been attained. Additionally, the ability to restrict Cas9 cleavage activity to a particular site, tissue, or cell cycle stage would greatly improve the efficacy and safety of Cas9-based clinical treatments and research applications.

SUMMARY OF THE INVENTION

The present invention is related to the field of CRISPR-Cas9 gene editing platforms. In particular, the present invention has identified Type II-C Cas9 anti-CRISPR (Acr) inhibitors that control Cas9 gene editing activity. Co-administration of such Acr inhibitors may provide an advantageous adjunct in permitting safe and practical biological therapeutics through spatial or temporal control of Cas9 activity; controlling Cas9-based gene drives in wild populations to reduce the ecological consequences of such forced inheritance schemes; and contributing to general research into various biotechnological, agricultural, and medical applications of gene editing technologies.

In one embodiment, the present invention contemplates a Type II-C anti-CRISPR (Acr) protein. In one embodiment, the Acr protein is a truncated protein. In one embodiment, the truncated protein is derived from an amino acid sequence including, but not limited to, SEQ ID NO: 2, SEQ ID NO: 4, SEQ ID NO: 6, SEQ ID NO: 8, SEQ ID NO: 10, SEQ ID NO: 12, SEQ ID NO: 14, and/or SEQ ID NO: 16. In one embodiment, the Acr protein is a fusion protein. In one embodiment, the Acr fusion protein comprises a C-terminal adduct. In one embodiment, the Acr fusion protein comprises an N-terminal adduct. In one embodiment, the adduct is a nuclear localization sequence. In one embodiment, the adduct is an affinity tag. In one embodiment, the affinity tag is FLAG. In one embodiment, the Acr protein is a dimer protein. In one embodiment, the Acr dimer protein is an Acr homodimer protein. In one embodiment, the Acr dimer protein is an Acr heterodimer protein. In one embodiment, the Acr protein is a mutated protein. In one embodiment, said Acr protein comprises at least a portion of an amino acid sequence selected from the group consisting of AcrIIC1Boe, AcrIIC1Nme, AcrIIC2Nme, AcrIIC3Nme, AcrIIC4Hpa, and AcrIIC5Smu. In one embodiment, said protein is less than approximately 14 kDa.

In one embodiment, the present invention contemplates a composition comprising a Type II-C Cas9 protein comprising a binding site and a Type II-C anti-CRISPR (Acr) protein, wherein said Acr protein binds with specific affinity to said binding site. In one embodiment, the Type II-C Cas9 protein is a *Brackiella oedipodis* Cas9 protein. In one embodiment, the Type II-C Cas9 protein is a *Neisseria meningitidis* Cas9 protein. In one embodiment, the Type II-C Cas9 protein is a *Haemophilus parainfluenzau* Cas9 protein. In one embodiment, the Type II-C Cas9 protein is a *Simonsiella muelleri* Cas9 protein. In one embodiment, the Type II-C Cas9 protein is a *Ralstonia solanacearum* Cas9 protein. In one embodiment, the Acr protein is a truncated protein. In one embodiment, the truncated protein is derived from an amino acid sequence including, but not limited to, SEQ ID NO: 2, SEQ ID NO: 4, SEQ ID NO: 6, SEQ ID NO: 8, SEQ ID NO: 10, SEQ ID NO: 12, SEQ ID NO: 14, and/or SEQ ID NO: 16. In one embodiment, the Acr protein is a fusion protein. In one embodiment, the Acr fusion protein comprises a C-terminal adduct. In one embodiment, the Acr fusion protein comprises an N-terminal adduct. In one embodiment, the adduct is a nuclear localization sequence. In one embodiment, the adduct is an affinity tag. In one embodiment, the affinity tag is FLAG. In one embodiment, the Acr protein is a dimer protein. In one embodiment, the Acr dimer protein is an Acr homodimer protein. In one embodiment, the Acr dimer protein is an Acr heterodimer protein. In one embodiment, the Acr protein is a mutated protein. In one embodiment, said type II-C Cas9 protein is a type II-C dCas9 protein. In one embodiment, said type II-C dCas9 protein is dNmeCas9.

In one embodiment, the present invention contemplates a method, comprising: a) providing; i) a biological cell comprising at least one suspect gene; ii) a Type II-C Cas9/sgRNA complex wherein said sgRNA is capable of hybridizing to a target site of said at least one suspect gene and said Type II-C Cas9 protein comprises a binding site; and iii) a Type II-C anti-CRISPR (Acr) protein that binds with specific affinity to said binding site; b) contacting said Type II-C Cas9/sgRNA complex with said biological cell such that said Type II-C Cas9/sgRNA complex hybridizes to said target site; c) editing said suspect gene with said Type II-C Cas9/sgRNA complex; and d) contacting said binding site with said Acr protein such that said editing is reduced. In one embodiment, the biological cell is a bacterial cell. In one embodiment, the biological cell is a fungal cell. In one embodiment, the biological cell is a mammalian cell. In one embodiment, the biological cell is an insect cell. In one embodiment, the biological cell is a plant cell. In one embodiment, the reduced editing resulting from Acr protein action slows said gene drive propagation. In one embodiment, the suspect gene is a mutated gene. In one embodiment, the suspect gene is a dysregulated gene. In one embodiment, the suspect gene is a damaged gene. In one embodiment, the suspect gene is a dysfunctional gene. In one embodiment, the Type II-C Cas9 protein is a *Brackiella oedipodis* Cas9 protein. In one embodiment, the Type II-C Cas9 protein is a *Neisseria meningitidis* Cas9 protein. In one embodiment, the Type II-C Cas9 protein is a *Haemophilus parainfluenzau* Cas9 protein. In one embodiment, the Type II-C Cas9 protein is a *Simonsiella muelleri* Cas9 protein. In one embodiment, the Type II-C Cas9 protein is a *Ralstonia solanacearum* Cas9 protein. In one embodiment, the target site is N-TS3. In one embodiment, the target site is N-TS7. In one embodiment, the target site is N-TS25. In one embodiment, the target site is D-TS3. In one embodiment, the target site is D-TS7. In one embodiment, the Acr protein is a truncated protein. In one embodiment, the truncated protein is derived from an amino acid sequence including, but not limited to, SEQ ID NO: 2, SEQ ID NO: 4, SEQ ID NO: 6, SEQ ID NO: 8, SEQ ID NO: 10, SEQ ID NO: 12, SEQ ID NO: 14, and/or SEQ ID NO: 16. In one embodiment, the Acr protein is a fusion protein. In one embodiment, the Acr fusion protein comprises a C-terminal adduct. In one embodiment, the Acr fusion protein comprises an N-terminal adduct. In one embodiment, the adduct is a nuclear localization sequence. In one embodiment, the adduct is an affinity tag. In one embodiment, the affinity tag is FLAG. In one embodiment, the Acr protein is a dimer protein. In one embodiment, the Acr dimer protein is an Acr homodimer protein. In one embodiment, the Acr dimer protein is an Acr heterodimer protein. In one embodiment, the Acr protein is a mutated protein. In one embodiment, said Acr protein comprises at least a portion of an amino acid sequence selected from the group consisting of AcrIIC1Boe, AcrIIC1Nme, AcrIIC2Nme, AcrIIC3Nme, AcrIIC4Hpa, and AcrIIC5Smu. In one embodiment, said Type II-C Cas9 is selected from the group consisting of a *Brackiella oedipodis* Cas9 protein, a *Neisseria meningitidis* Cas9 protein, a *Haemophilus influenzae* Cas9 protein, a *Simonsiella muelleri* Cas9 protein, and a *Ralstonia solanacearum* Cas9 protein. In one embodiment, said type II-C Cas9 protein is a type II-C dCas9 protein. In one embodiment, said type II-C dCas9 protein is dNmeCas9. In one embodiment, said reduced editing prevents at least one off-target event of Cas9 binding. In one embodiment, said at least one off-target event is selected from the group consisting of DNA cleavage and DNA mutation. In one embodiment, said reduced editing occurs during the G1 phase of the cell cycle. In one embodiment, said reduced editing prevents mosaic genotypes. In one embodiment, said reduced editing inhibits a gene drive. In one embodiment, said reduced editing is selected from the group consisting of at least 70%, 75%, 90% or greater and 100%. In one embodiment, said reduced editing is precisely controlled. In one embodiment, the suspect gene is a mutated gene. In one embodiment, the suspect gene is a dysregulated gene. In one embodiment, the suspect gene is a damaged gene. In one embodiment, the suspect gene is a dysfunctional gene.

In one embodiment, the present invention contemplates a method, comprising: a) providing; i) a virus comprising at least one suspect gene; ii) a Type II-C Cas9/sgRNA complex wherein said sgRNA is capable of hybridizing to a target site of said at least one suspect gene and said Type II-C Cas9 protein comprises a binding site; and iii) a Type II-C anti-CRISPR (Acr) protein that binds with specific affinity to said binding site; b) contacting said Type II-C Cas9/sgRNA complex with said virus such that said Type II-C Cas9/sgRNA complex hybridizes to said suspect gene; c) editing said suspect gene with said Type II-C Cas9/sgRNA complex; and d) contacting said binding site with said Acr protein such that said editing is reduced. In one embodiment, the suspect gene is a mutated gene. In one embodiment, the suspect gene is a dysregulated gene. In one embodiment, the suspect gene is a damaged gene. In one embodiment, the suspect gene is a dysfunctional gene. In one embodiment, the Type II-C Cas9 protein is a *Brackiella oedipodis* Cas9 protein. In one embodiment, the Type II-C Cas9 protein is a *Neisseria meningitidis* Cas9 protein. In one embodiment, the Type II-C Cas9 protein is a *Haemophilus parainfluenzau* Cas9 protein. In one embodiment, the Type II-C Cas9 protein is a *Simonsiella muelleri* Cas9 protein. In one embodiment, the Type II-C Cas9 protein is a *Ralstonia solanacearum* Cas9 protein. In one embodiment, the target site is N-TS3. In one embodiment, the target site is N-TS7. In one embodiment, the target site is N-TS25. In one embodiment, the target site is D-TS3. In one embodiment, the target site is D-TS7. In one embodiment, the Acr protein is a truncated protein. In one embodiment, the truncated protein is derived from an amino acid sequence including, but not limited to, SEQ ID NO: 2, SEQ ID NO: 4, SEQ ID NO: 6, SEQ ID NO: 8, SEQ ID NO: 10, SEQ ID NO: 12, SEQ ID NO: 14, and/or SEQ ID NO: 16. In one embodiment, the Acr protein is a fusion protein. In one embodiment, the Acr fusion protein comprises a C-terminal adduct. In one embodiment, the Acr fusion protein comprises an N-terminal adduct. In one embodiment, the adduct is a nuclear localization sequence. In one embodiment, the adduct is an affinity tag. In one embodiment, the affinity tag is FLAG. In one embodiment, the Acr protein is a dimer protein. In one embodiment, the Acr dimer protein is an Acr homodimer protein. In one embodiment, the Acr dimer protein is an Acr heterodimer protein. In one embodiment, the Acr protein is a mutated protein. In one embodiment, said Acr protein comprises at least a portion of an amino acid sequence selected from the group consisting of AcrIIC1Boe, AcrIIC1Nme, AcrIIC2Nme, AcrIIC3Nme, AcrIIC4Hpa, and AcrIIC5Smu. In one embodiment, said Type II-C Cas9 is selected from the group consisting of a *Brackiella oedipodis* Cas9 protein, a *Neisseria meningitidis* Cas9 protein, a *Haemophilus influenzae* Cas9 protein, a *Simonsiella muelleri* Cas9 protein, and a *Ralstonia solanacearum* Cas9 protein. In one embodiment, said type II-C Cas9 protein is a type II-C dCas9 protein. In one embodiment, said type II-C dCas9 protein is dNmeCas9. In one embodiment, said reduced editing prevents at least one off-target event of Cas9 binding. In one embodiment, said at least one off-target event is selected from the group consisting of DNA cleavage and DNA mutation. In one embodiment, said reduced editing occurs during the G1 phase of the cell cycle. In one embodiment, said reduced editing prevents mosaic genotypes. In one embodiment, said reduced editing inhibits a gene drive. In one embodiment, said reduced editing is selected from the group consisting of at least 70%, 75%, 90% or greater and 100%. In one embodiment, said reduced editing is precisely controlled. In one embodiment, the suspect gene is a mutated gene. In one embodiment, the suspect gene is a dysregulated gene. In one embodiment, the suspect gene is a damaged gene. In one embodiment, the suspect gene is a dysfunctional gene.

In one embodiment, the present invention contemplates a method, comprising: a) providing; i) a mammal comprising at least one suspect gene; ii) a Type II-C Cas9/sgRNA complex wherein said sgRNA is capable of hybridizing to a target site of at least one suspect gene and said Type II-C Cas9 protein comprises a binding site; and iii) a Type II-C anti-CRISPR (Acr) protein that is capable of binding with specific affinity to said binding site; b) administering said Type II-C Cas9/sgRNA complex to said mammal such that said Type II-C Cas9/sgRNA complex binds to said target site; c) editing said suspect gene with said Type II-C Cas9/sgRNA complex; and d) administering said Acr protein to said mammal such that said Acr protein binds with specific affinity to said binding site such that said editing is reduced. In one embodiment, the mammal is a human. In one embodiment, the mammal is a livestock species. In one embodiment, the mammal exhibits at least one symptom of a medical disorder or disease resulting from the presence of said suspect gene. In one embodiment, the editing of said suspect gene reduces said at least one symptom. In one embodiment, the suspect gene is a mutated gene. In one embodiment, the suspect gene is a dysregulated gene. In one embodiment, the suspect gene is a damaged gene. In one embodiment, the suspect gene is a dysfunctional gene. In one embodiment, the Type II-C Cas9 protein is a *Brackiella oedipodis* Cas9 protein In one embodiment, the Type II-C Cas9 protein is a *Neisseria meningitidis* Cas9 protein. In one embodiment, the Type II-C Cas9 protein is a *Haemophilus parainfluenzau* Cas9 protein. In one embodiment, the Type II-C Cas9 protein is a *Simonsiella muelleri* Cas9 protein. In one embodiment, the Type II-C Cas9 protein is a *Ralstonia solanacearum* Cas9 protein. In one embodiment, the target site is N-TS3. In one embodiment, the target site is N-TS7. In one embodiment, the target site is N-TS25. In one embodiment, the target site is D-TS3. In one embodiment, the target site is D-TS7. In one embodiment, the Acr protein is a truncated protein. In one embodiment, the truncated protein is derived from an amino acid sequence including, but not limited to, SEQ ID NO: 2, SEQ ID NO: 4, SEQ ID NO: 6, SEQ ID NO: 8, SEQ ID NO: 10, SEQ ID NO: 12, SEQ ID NO: 14, and/or SEQ ID NO: 16. In one embodiment, the Acr protein is a fusion protein. In one embodiment, the Acr fusion protein comprises a C-terminal adduct. In one embodiment, the Acr fusion protein comprises an N-terminal adduct. In one embodiment, the adduct is a nuclear localization sequence. In one embodiment, the adduct is an affinity tag. In one embodiment, the affinity tag is FLAG. In one embodiment, the Acr protein is a dimer protein. In one embodiment, the Acr dimer protein is an Acr homodimer protein. In one embodiment, the Acr dimer protein is an Acr heterodimer protein. In one embodiment, the Acr protein is a mutated protein. In one embodiment, said Acr protein comprises at least a portion of an amino acid sequence selected from the group consisting of AcrIIC1Boe, AcrIIC1Nme, AcrIIC2Nme, AcrIIC3Nme, AcrIIC4Hpa, and AcrIIC5Smu. In one embodiment, said Type II-C Cas9 is selected from the group consisting of a *Brackiella oedipodis* Cas9 protein, a *Neisseria meningitidis* Cas9 protein, a *Haemophilus influenzae* Cas9 protein, a *Simonsiella muelleri* Cas9 protein, and a *Ralstonia solanacearum* Cas9 protein. In one embodiment, said type II-C Cas9 protein is a type II-C dCas9 protein. In one embodiment, said type II-C dCas9 protein is dNmeCas9. In one embodiment, said reduced editing prevents at least one off-target event of Cas9 binding. In one embodiment, said at least one off-target event is selected from the group consisting of DNA cleavage and DNA mutation. In one embodiment, said at least one off-target event occurs during a G1 phase cell cycle. In one embodiment, said reduced editing prevents mosaic genotypes. In one embodiment, said reduced editing inhibits a gene drive. In one embodiment, said reduced editing is selected from the group consisting of at least 70%, 75%, 90% greater and 100%. In one embodiment, said reduced editing is precisely controlled. In one embodiment, the suspect gene is a mutated gene. In one embodiment, the suspect gene is a dysregulated gene. In one embodiment, the suspect gene is a damaged gene. In one embodiment, the suspect gene is a dysfunctional gene. In one embodiment, the present invention contemplates a kit, comprising: a) a first container comprising at least one Type II-C anti-CRISPR (Acr) protein; b) a second container comprising a Type II-C Cas9 protein; and c) a third container comprising an sgRNA. In one embodiment, said Acr protein comprises at least a portion of an amino acid sequence selected from the group consisting of AcrIIC1Boe, AcrIIC1Nme, AcrIIC2Nme, AcrIIC3Nme, AcrIIC4Hpa, and AcrIIC5Smu. In one embodiment, said Type II-C Cas9 is selected from the group consisting of a *Brackiella oedipodis* Cas9 protein, a *Neisseria meningitidis* Cas9 protein, a *Haemophilus influenzae* Cas9 protein, a *Simonsiella muelleri* Cas9 protein, and a *Ralstonia solanacearum* Cas9 protein. In one embodiment, said type II-C Cas9 protein is a type II-C dCas9 protein. In one embodiment, said type II-C dCas9 protein is dNmeCas9.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

One of skill in the art will understand the interchangability of terms designating the various anti-CRISPR proteins due to a lack of consistency in the literature and an ongoing effort in the art to unify such terminology. For example, as used herein the designation of Acr1-Bo is interchangeable with AcrIIC1Boe and the designation of Acr2-Nm is interchangeable with AcrIIC2Nme. Also, as used herein, the designation of Acr88a-32 is interchangeable with AcrE2. This type of equivalency may also be seen in the various other designations as used throughout the present application.

The term "about" as used herein, in the context of any of any assay measurements refers to +/−5% of a given measurement.

As used herein, the term "intein" refers to a segment of a protein that is able to excise itself and join the remaining portions of the protein (e.g., the exteins) with a peptide bond in a process termed protein splicing. Inteins have also been called "protein introns". This process involves intein-mediated protein splicing that occurs after an intein-containing mRNA has been translated into a protein. Consequently, a precursor protein contains three segments—an N-extein followed by the intein followed by a C-extein. After splicing has taken place, the resulting protein contains the N-extein linked to the C-extein; this splicing product is also termed an extein.

The term "suspect gene" as used herein, refers to a gene of interest wherein editing of the gene may have beneficial consequences to the health of the cell in which the gene resides, or the health of the organism in which the cell resides. A suspect gene refers also to a gene of interest in a cell or organism wherein editing of the gene may provide biological insight in laboratory experiments. In general, a suspect gene may include but is not limited to a mutated gene, a dysregulated gene, a damaged gene, and/or a dysfunctional gene.

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by the same series in reverse and then by approximately 30 base pairs known as "spacer DNA". The spacers are short segments of DNA that are often derived from a bacterial virus or other foreign genetic element and may serve as a 'memory' of past exposures to facilitate an adaptive defense against future invasions. Doudna et al., "Genome editing. The new frontier of genome engineering with CRISPR-Cas9" Science. 2014 346(6213): 1258096.

As used herein, the term "Cas" or "CRISPR-associated (cas)" refers to genes or derived proteins often associated with CRISPR repeat-spacer arrays. Doudna et al., "Genome editing. The new frontier of genome engineering with CRISPR-Cas9" Science. 2014 346(6213):1258096.

As used herein, the term "Cas9" refers to a nuclease from Type II CRISPR systems, an enzyme specialized for generating double-strand breaks in DNA, with two active cutting sites (the HNH and RuvC domains), one for each strand of the double helix. Jinek et al combined tracrRNA and spacer RNA into a "single-guide RNA" (sgRNA) molecule that, mixed with Cas9, could find and cleave DNA targets through Watson-Crick pairing between the guide sequence within the sgRNA and the target DNA sequence. Jinek et al., "A programmable dual-RNA-guided DNA endonuclease in adaptive bacterial immunity" Science. 2012 337(6096):816-821 Epub 2012 Jun. 28.

As used herein, the term "catalytically active Cas9" refers to an unmodified Cas9 nuclease comprising full nuclease activity.

The term "binding site" as used herein refers to a Cas9 amino acid sequence having specific affinity for an Acr1 protein.

The term "target site" as used herein refers to a nucleic acid sequence flanking a suspect gene that hybridizes to an sgRNA sequence.

The term "nickase" as used herein, refers to a nuclease that cleaves only a single DNA strand, either due to its natural function or because it has been engineered to cleave only a single DNA strand. Cas9 nickase variants that have either the RuvC or the HNH domain mutated provide control over which DNA strand is cleaved and which remains intact. Cong et al., "Multiplex genome engineering using CRISPR/Cas systems" Science. 2013 339(6121):819-823. Epub 2013 Jan. 3.

The term "protospacer adjacent motif" (or PAM) as used herein, refers to a DNA sequence present on the target DNA molecule adjacent to the sequence matching the guide RNA spacer. The PAM is required for a Cas9/sgRNA to form an R-loop to interrogate a specific DNA sequence through Watson-Crick pairing of its guide RNA with the genome. The PAM specificity may be a function of the DNA-binding specificity of the Cas9 protein (e.g., a "protospacer adjacent motif recognition domain" at the C-terminus of Cas9).

As used herein, the term "sgRNA" refers to single guide RNA used in conjunction with CRISPR associated systems (Cas). sgRNAs are a fusion of crRNA and tracrRNA and contain nucleotides of sequence complementary to the desired target site. Watson-Crick pairing of the sgRNA with the target site permits R-loop formation, which in conjunction with a functional PAM permits DNA cleavage or in the case of nuclease-deficient Cas9 allows tight binding to the DNA at that locus.

The term "dimerization domain" as used herein, refers to a domain, either protein, polynucleotide that allows the associate of two different molecules. A dimerization domain can allow homotypic and/or heterotypic interactions. Dimerization domains can also be drug-dependent (i.e. depending on the presence of a small molecule in order to function). Ho et al., "Dimeric ligands define a role for transcriptional activation domains in reinitiation" Nature. 1996 382(6594):822-826.

As used herein, the term "edit" "editing" or "edited" refers to a method of altering a nucleic acid sequence of a polynucleotide (e.g., for example, a wild type naturally occurring nucleic acid sequence or a mutated naturally occurring sequence) by selective deletion of a specific genomic target or the specific inclusion of new sequence through the use of an exogenously supplied DNA template. Such a specific genomic target includes, but may be not limited to, a chromosomal region, mitochondrial DNA, a gene, a promoter, an open reading frame or any nucleic acid sequence.

The term "delete", "deleted", "deleting" or "deletion" as used herein, may be defined as a change in either nucleotide or amino acid sequence in which one or more nucleotides or amino acid residues, respectively, are, or become, absent.

The term "suspected of having", as used herein, refers a medical condition or set of medical conditions (e.g., preliminary symptoms) exhibited by a patient that is insufficient to provide a differential diagnosis. Nonetheless, the exhibited condition(s) would justify further testing (e.g., autoantibody testing) to obtain further information on which to base a diagnosis.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc) to a binding partner under conditions such that the binding partner becomes unresponsive to its natural ligands. Inhibitory compounds may include, but are not limited to, small organic molecules, antibodies, and proteins/peptides.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The terms "specific affinity" or "specifically bound" when used in reference to the interaction of a protein or peptide means that the interaction is dependent upon the presence of particular structures (i.e., for example, an target site, or binding site) on a protein determined by the tertiary and/or quaternary folding of a primary amino acid sequence. In other words, a protein or peptide is recognizing and binding to a particular conformational protein structure rather than to proteins in general.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The term "derived from" as used herein, refers to the source of a compound or sequence. In one respect, a compound or sequence may be derived from an organism or particular species. In another respect, a compound or sequence may be derived from a larger complex or sequence.

The term "test compound" as used herein, refers to any compound or molecule (including proteins) considered a candidate as an inhibitory compound.

The term "protein" as used herein, refers to any of numerous naturally occurring extremely complex substances (as an enzyme or antibody) that consist of amino acid residues joined by peptide bonds and contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

A "variant" of a protein is defined as an amino acid sequence which differs by one or more amino acids from a polypeptide sequence or any homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A "variant" of a nucleotide sequence is defined as a novel nucleotide sequence which differs from a reference oligonucleotide by having deletions, insertions and substitutions. These may be detected using a variety of methods (e.g., sequencing, hybridization assays etc.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues. A "substitution" results from the replacement of one or more nucleotides or amino acids by different nucleotides or amino acids, respectively.

The term "derivative" as used herein, refers to any chemical modification of a nucleic acid or an amino acid. Illustrative of such modifications would be replacement of hydrogen by an alkyl, acyl, or amino group. For example, a nucleic acid derivative would encode a polypeptide which retains essential biological characteristics.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frame-shift mutation). Complementation is achieved by transfecting cells which lack protein activity with an expression vector which expresses the protein, a derivative thereof, or a portion thereof.

The terms "binding component", "molecule of interest", "agent of interest", "ligand" or "receptor" as used herein may be any of a large number of different molecules, biological cells or aggregates, and the terms are used interchangeably. Proteins, polypeptides, peptides, nucleic acids (nucleotides, oligonucleotides and polynucleotides), antibodies, ligands, saccharides, polysaccharides, microorganisms such as bacteria, fungi and viruses, receptors, antibiotics, test compounds (particularly those produced by combinatorial chemistry), plant and animal cells, organs or fractions of each and other biological entities may each be a binding component. The term "macromolecule" as used herein, refers to any molecule of interest having a high molecular weight. For example, some biopolymers having a high molecular weight would be comprised of greater than 100 amino acids, nucleotides or sugar molecules.

The term "bind", "binding" or "bound" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That is typical when the binding component is an enzyme and the analyte is a substrate for the enzyme. Reactions resulting from contact between the binding agent and the analyte are also within the definition of binding for the purposes of the present invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 11A: Acr1Bo with a C-terminal FLAG tag.

FIG. 11B: Acr1Bo with a N-terminal FLAG tag.

FIG. 12A: Acr1Nm with a C-terminal FLAG tag.

FIG. 12B: Acr1Nm with a N-terminal FLAG tag.

FIG. 13A: Acr2 Nm with a C-terminal FLAG tag.

FIG. 13B: Acr2 Nm with a N-terminal FLAG tag.

FIG. 14A: Acr3 Nm with a C-terminal FLAG tag.

FIG. 14B: Acr3 Nm with a N-terminal FLAG tag.

FIG. 15A: Acr1Bo

FIG. 15B: Acr1Nm

FIG. 15C: Acr2 Nm

FIG. 15D: Acr3 Nm

FIG. 19A: Schematic representation of candidate type II-C acr and aca genes within putative MGEs in the genomes of strains of *Brackiella oedipodis* and *Neisseria meningitidis*. Orthologous genes are color-matched, with percent amino acid identities indicated. Gene arrows are not drawn to scale. Any known, relevant gene product functions are annotated as follows: Rep, plasmid replication protein; Reg, transcriptional regulator; Tra, conjugal transfer protein; Rec, recombinase; Tail, phage tail structural protein; Lysis, phage lysis cassette. Genes colored in grey have MGE-related functions or show clear evidence of horizontal transfer.

FIG. 19B: Schematic representation of genotypes in *N. meningitidis* strains used to test candidate anti-CRISPR function. Diamonds, CRISPR repeats; numbered rectangles, CRISPR spacers; arrows, CRISPR transcription. ermC, integrated erythromycin resistance cassette; acrX, integrated candidate anti-CRISPR cassette. Individual genetic elements are not to scale.

FIG. 19C: Candidate type II-C anti-CRISPR proteins inhibit CRISPR interference in *N. meningitidis*. Results of the transformation assay in *N. meningitidis* strain 8013, and isogenic derivatives with each indicated acr gene integrated at the nics locus (see B), are plotted. The CRISPR-targeted protospacer plasmid (navy) cannot transform wild-type and empty vector-containing cells due to an active CRISPR-Cas system, resulting in zero transformants. BDL=below detection limit of this assay. Plasmid DNA that lacks a target protospacer sequence can transform all strains equally well (yellow). Experiments were repeated three times and error bars represent the standard error of the mean (s.e.m.) between three replicates. Cells were also plated on non-selective media and the total number of cfu/mL present was equivalent in each sample (data not shown).

FIG. 21A: Purified, untagged anti-CRISPR proteins were mixed with purified, 6×His tagged NmeCas9:sgRNA in vitro. The input and elution fractions (before and after nickel affinity purification) are shown on the right and left sides of the Coomassie-stained SDS-PAGE gel, respectively. Mobilities of marker proteins (in kDa) are denoted on the left. AcrE2 is an inhibitor of the type I-E CRISPR-Cas system, and is included in this assay as a negative control.

FIG. 21B: Binding assays were carried out between the same anti-CRISPR proteins tested in (A) and Cas9 from *Actinomyces naeslundii* (AnaCas9). AnaCas9 is a distantly related type II-C Cas9 protein (~20% amino acid sequence identity with NmeCas9).

FIG. 24A: Schematic representation of R-loop structures at a dual target site (DTS3) in the human genome that can be cleaved and edited by either SpyCas9 (top) or NmeCas9 (bottom). Guide sequences (purple), PAMs (boxed), and Cas9 cleavage sites (red line) are indicated.

FIG. 24B: T7E1 assays of NmeCas9 or SpyCas9 editing efficiencies at DTS3 upon transient transfection of human HEK293T cells. Constructs encoding anti-CRISPR proteins were cotransfected as indicated at the top of each lane. Mobilities of T7E1-digested (edited) and -undigested (unedited) bands are indicated to the right, and editing efficiencies ("% lesion") are given at the bottom of each lane.

FIG. 25A-B presents exemplary data showing that AcrIIC1Boe blocks NmeCas9-Mediated Genome Editing at Multiple Human Genome Sites. Related to FIG. 24A-B.

FIG. 25A: T7E1 assays of NmeCas9 editing efficiencies at multiple sites, with canonical (N4GATT) or variant (N4GTTT, N4GTCT) PAMs, upon transient transfection of human HEK293T cells. Plasmid encoding AcrIIC1Boe proteins was co-transfected as indicated at the top of each lane. For the D-TS7 target site, SpyCas9 editing (with and without AcrIIC1Boe) was also tested. Editing efficiencies ("% lesion") are given at the bottom of each lane.

FIG. 25B: For the D-TS3 site tested in FIG. 24A-B, and for each site tested in FIG. 25A, the NmeCas9 sgRNA spacer sequences (5' to 3') and DNA target sites (non-complementary strand, 5' to 3') are listed.

FIG. 26A: T7E1 assays of NmeCas9 editing efficiencies at DTS3 upon transient transfection of human HEK293T cells. Constructs encoding anti-CRISPR proteins were co-transfected as indicated at the top of each lane. The total amount of anti-CRISPR proteins was held constant at 100 ng per well, but the relative amount of a negative control anti-CRISPR (AcrE2) and test anti-CRISPR (AcrIIC1Boe) was varied. Editing efficiencies ("% lesion") are given at the bottom of each lane.

FIGS. 26B-E: As in (A), except that AcrIIC1Nme (B), AcrIIC2Nme (C), and AcrIIC3Nme (D and E) were used. In (D), because inhibition was nearly complete even at the lowest dose (10 ng) of AcrIIC3Nme plasmid, we repeated the titration with lower levels of plasmid in (E), revealing the dose-dependence of inhibition.

FIG. 27A: Schematic representation of plasmids used for expression of dNmeCas9-(sfGFP)$_3$, dSpyCas9-(mCherry)$_3$, their respective telomeric sgRNAs, and anti-CRISPR proteins. The plasmid encoding the anti-CRISPR protein is also marked with the blue fluorescent protein mTagBFP2.

FIGS. 27B-F: Fluorescence images of U2OS cells transiently transfected with plasmids depicted in FIG. 27A. The specific version of each plasmid set (with or without sgRNAs, with or without anti-CRISPRs) is given to the right of each row. First column: differential interference contrast (DIC) and mTagBFP2 imaging, merged. Second column: dNmeCas9-(sfGFP)3. Third column: dSpyCas9-(mCherry)3. Fourth column: dNmeCas9-(sfGFP)3 and dSpyCas9-(mCherry)3, merged. Scale bars, 5 sm.

FIG. 28A: Sequence similarity tree of the interference proteins of a representative set of CRISPR-Cas systems (Makarova et al., 2015). Class 1 systems are multi-subunit effector complexes, whereas Class 2 systems employ single effector proteins. Type and subtype clades are labelled. Stars indicate the types of CRISPR-Cas systems for which anti-CRISPR proteins have been discovered.

FIG. 28B: A maximum likelihood phylogenetic tree of representative Cas9 protein sequences. Each protein is classified based on the CRISPR locus in which it resides as type II-A (blue), type II-B (yellow), or type II-C (purple). Cas9 proteins belonging to any genus that has a type II-C anti-CRISPR ortholog are coloured in red. With the assumption that a given anti-CRISPR ortholog inhibits the CRISPR-Cas system in the species where it is found, this visualization provides an estimate of the breadth of activity encompassed by the anti-CRISPR families discovered here.

DETAILED DESCRIPTION OF THE INVENTION

Figure 1:
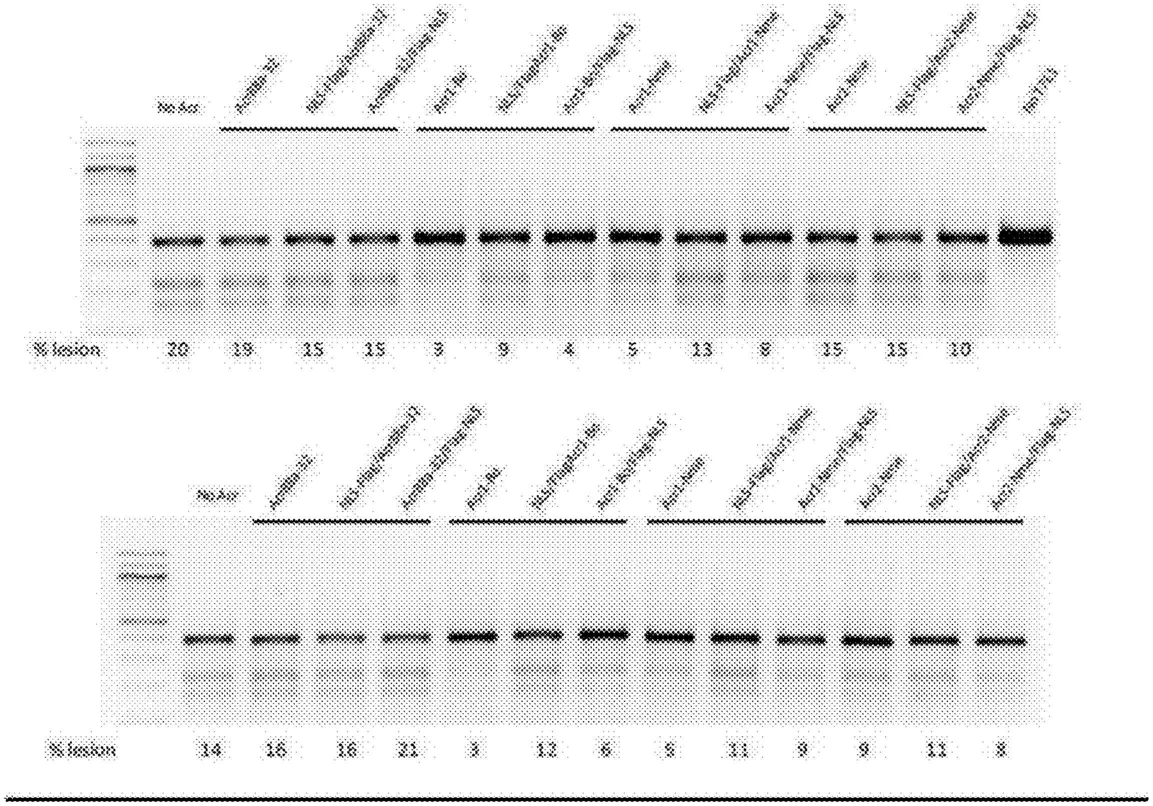
FIG. 1 presents exemplary data showing selective inhibition of NmeCas9 gene editing at the N-TS3 target site with several Acr proteins. NmeCas9+SgRNA plasmid (200 ng)+Acr plasmid (100 ng).

The present invention is related to the field of CRISPR-Cas9 gene editing platforms. In particular, the present invention has identified Type II-C Cas9 anti-CRISPR (Acr) inhibitors that control Cas9 gene editing activity. Co-administration of such Acr inhibitors may provide an advantageous adjunct in permitting safe and practical biological therapeutics through spatial or temporal control of Cas9 activity; controlling Cas9-based gene drives in wild populations to reduce the ecological consequences of such forced inheritance schemes; and contributing to general research into various biotechnological, agricultural, and medical applications of gene editing technologies.

I. CRISPR Gene Editing Platform

CRISPR-Cas systems are adaptive immune systems in bacteria and archaea that help defend against attack by predatory viruses. These systems use small RNAs [CRISPR RNAs (crRNAs)] as guides to identify their nucleic acid targets, which are then cleaved and inactivated. In most instances, the target nucleic acid is DNA, not RNA.

Clustered Regularly Interspaced Short Palindromic Repeat (CRISPR) RNA sequences and CRISPR-associated (Cas) genes form catalytic protein-RNA complexes that utilize the incorporated RNA to generate sequence-specific double strand breaks at a complementary DNA sequence. This nuclease platform has displayed remarkable robustness for targeted gene inactivation or tailor-made genome editing. Sander et al., CRISPR-Cas systems for editing, regulating and targeting genomes. Nature Biotechnology 32, 347-355 (2014); Mali et al. RNA-guided human genome engineering via Cas9. Science 339, 823-826 (2013); Ran et al. Double Nicking by RNA-Guided CRISPR Cas9 for Enhanced Genome Editing Specificity. Cell 154, 1380-1389 (2013); Fu et al., Improving CRISPR-Cas nuclease specificity using truncated guide RNAs. Nature Biotechnology 32, 279-284 (2014); and Wang et al. One-step generation of mice carrying mutations in multiple genes by CRISPR/Cas-mediated genome engineering. Cell 153, 910-918 (2013).

The CRISPR/Cas9 genome engineering system is revolutionizing biological sciences due to its simplicity and efficacy[1-3]. The most commonly studied Cas9 nuclease originates from *Streptococcus pyogenes* (SpyCas9)[4]. SpyCas9 and its associated guide RNA license a DNA sequence for cleavage based on at least two stages of sequence interrogation[4-8]: i) compatibility of a PAM element with the specificity of the PAM-interacting domain, and ii) complementarity of a guide RNA sequence with the target site. Because it is straightforward to program Cas9 to cleave a desired target site through incorporation of a complementary single guide RNA (sgRNA)[4], a primary constraint on Cas9 targeting is the presence of a compatible PAM element[4,9,10]. For example, a PAM-interacting domain of wild-type SpyCas9 (SpyCas9$^{WT}$) preferentially recognizes a NGG element[4], although it can inefficiently utilize other PAM sequences (e.g. nAG, nGA)[9,11]. The simplicity of a SpyCas9/sgRNA system allows facile editing of genomes in a variety of organisms and cell lines[1-3]. Target specificity may be a function of recognition by both the guide RNA (through Watson-Crick base pairing) and an inherent specificity of Cas9 through recognition of a neighboring motif (e.g., for example, a protospacer adjacent motif (PAM)).

A subset of CRISPR-Cas systems (those known as "Type II") employ a protein called Cas9, and this protein (along with its RNA guides) has been adapted as a revolutionary genome editing platform. Variants carrying mutations in its nuclease active sites have also been developed as RNA-guided DNA binding platforms to enable gene labeling and transcriptional control. Cas9 is already in wide use as a research tool, and it is also being used in a broad range of biotechnology applications, and in livestock, agriculture, and elsewhere.

In addition, CRISPR-Cas9 platforms are being developed as a potentially revolutionary therapeutic approach to many diseases, given its potential ability to modify genomic loci that contribute to disease, to destroy the genomes of pathogens, or to introduce therapeutically useful sequences (e.g., chimaeric antigen receptors for cancer immunotherapies). Numerous Cas9s from various sources have been developed and adapted for these purposes, including, but not limited to, Cas9s encoded by the genomes of certain strains of *Streptococcus pyogenes, Streptococcus thermophilus*, and *Staphylococcus aureus*. These three are all from a sub-type of CRISPR-Cas systems known as Type II-A.

Most reported applications thus far have used *S. pyogenes* Cas9 (SpyCas9), which is the best characterized version, and more recently, *S. aureus* Cas9 (SauCas9). In addition to these Type II-A Cas9s, genome editing applications have been developed using *N. meningitidis* Cas9 (NmeCas9; Type II-C). Hou et al., "Efficient genome engineering in human pluripotent stem cells using Cas9 from *Neisseria meningitidis" Proc Natl. Acad Sci. USA* 110:15644-15649 (2013); and Zhang et al., "DNase H activity of *Neisseria meningitidis* Cas9" Molecular Cell 60:242-255 (2015).

A. Cas9 Activity Modulation

One current limitation of Cas9 application is that its activity can be very difficult to control—it is generally active as long as it is present and has access to its crRNA guide usually in the form of a so-called single-guide RNA (sgRNA). This lack of control can introduce difficulties for many reasons. Most notably, although Cas9 is often highly accurate at editing only the genomic locus to which it is directed, off-target effects are not uncommon. Off-target Cas9 activity has an unintended consequence of introducing mutations to unintended sites. This is a concern for many purposes especially, but not exclusively, to clinical therapeutics.

It is well established that the more functional Cas9/sgRNA that is present in a cell, and the longer that the Cas9/sgRNA persists, the greater the likelihood of off-target effects. Although it is not necessary to understand the mechanism of an invention, it is believed that once "on-target" genome edits have occurred, persistent Cas9/sgRNA can no longer recognize and edit the intended locus, thereby completing its intended purpose. Nonetheless, the still-functional Cas9/sgRNA complex can continue to find and edit off-target sites elsewhere.

In one embodiment, the present invention contemplates a composition that inhibits Cas9/sgRNA activity. Although it is not necessary to understand the mechanism of the invention, it is believed that these inhibitor compounds interact with active Cas9/sgRNA and function as an "off switch" that reduces Cas9/sgRNA activity to a minimal amount and/or for a duration necessary for its intended purpose. It is further believed that a Cas9/sgRNA inhibitor composition can limit Cas9/sgRNA activity to particular tissues or organs, or to any given set of user-defined conditions, by "tripping the off-switch" anywhere, at any time or under any circumstance when its activity is not desired.

The present embodiments have specific advantages over other potential ways to control Cas9/sgRNA activity and/or tissue specificity, such as: i) limiting Cas9/sgRNA production; ii) controlling Cas9/sgRNA dosage; iii) use of specific promoters or other gene expression control elements; iv) using transient or tissue-specific delivery modalities. The regulatory control imparted by these alternative approaches fail to be as precise and/or transient as necessary, and any Cas9/sgRNA that does get introduced remains active for as long as it is present.

Others have suggested various methods to control Cas9/sgRNA activity:

i) Cas9/sgRNA can be split into two separate half-proteins, with its dimerization into an active form dependent upon a small molecule (e.g. rapamycin). Zetsche et al., "A split-Cas9 architecture for inducible genome editing and transcription modulation" *Nature Biotechnol.* 33:139-140 (2015). Here, the small molecule acts as an "on-switch," and its withdrawal can substitute for an "off-switch". However, among other limitations, the effects of small molecule withdrawal are not immediate, depending on its off-rate from Cas9 and on the persistence of the small molecules that were previously delivered.

(ii) Cas9/sgRNA can be disrupted by a ligand-dependent intein, rendering Cas9 inactive until a ligand (e.g., 4-hydroxytamoxifen (4-HT)) is added to trigger intein autoexcision and Cas9 activation. Davis et al., "Small molecule-triggered Cas9 protein with improved genome-editing specificity" *Nature Chem. Biol.* 11:316-318 (2015). Again, this is an on-switch mechanism, and the withdrawal of 4-HT will prevent further production of active Cas9. However, there is still no off-switch, and previously produced Cas9 will remain present and active.

(iii) Cas9/sgRNA can be fused to exogenous protein domains that confer light-inducible localization to the nucleus, where the target genome resides. As long as light of the appropriate wavelength is present, the Cas9/sgRNA remains in the nucleus and gene editing continues. When the light is withdrawn, the Cas9/sgRNA translocates to the cytoplasm and nuclear gene editing stops. Nihongaki et al., "Photoactivatable CRISPR-Cas9 for optogenetic genome editing" *Nature Biotechnol.* 33:755-760 (2015). However, it is usually not possible to exert sufficient control over the presence or absence of the appropriate light especially in living plants and animals, or outside of a controlled environment such as a laboratory. Furthermore, a Cas9/sgRNA might still have access to the genome, for example, under conditions as when the nuclear envelope is absent or compromised, e.g. during mitosis.

Accordingly, the identification or development of effective Cas9 off-switches would be a useful improvement in the art. Because CRISPR-Cas systems defend against virus (bacteriophage) predation, these systems impose a strong evolutionary pressure on viruses to develop mechanisms to evade or counteract CRISPR-Cas defensive functions.

B. Type I CRISPR-Cas Inhibitors

Type I CRISPR-Cas systems, in contrast to Cas9-based Type II systems, employ a large, multisubunit protein complex for DNA surveillance and cleavage. As such, Type I systems are not as promising for many gene editing platforms as they comprise a more complicated system. However, Type I systems are prevalent in bacteria and they provide immunity against the viruses that infect bacteria, known as bacteriophages. Bacteriophage genes have been identified that encode protein inhibitors (anti-CRISPR: Acr) of Type I CRISPR-Cas systems. Bondy-Denomy et al., "Bacteriophage genes that inactivate the CRISPR/Cas bacterial immune system" *Nature* 493:429-432 (2013): Bondy-Denomy et al., "Multiple mechanisms for CRISPR-Cas inhibition by anti-CRISPR proteins" *Nature* 526:136-139 (2015); and Pawluk et al., "A new group of phage anti-CRISPR genes inhibits the Type I-E CRISPR-Cas system of *Pseudomonas aeruginosa*" mBio 5:e00896-14 (2014). Each Type I anti-CRISPR identified to date possesses specificity to either the Type I-E or Type I-F subtypes of CRISPR-Cas systems, and therefore would not be expected to have an effect on any Cas9-based Type II systems. The Type I Acr proteins that have been characterized reportedly function by a direct, inhibitory binding to components of the CRISPR-Cas machinery, and each distinct Acr protein reportedly functions by a distinct mechanism of action.

II. Type II Cas9 Inhibitor Compositions

In addition to phage-encoded Acr proteins that prevent Type I CRISPR-based immunity, the identification of Acr-associated (Aca) transcriptional regulators of the helix-turn-helix xenobiotic response element (HTH-XRE) family have also come to light. Aca transcriptional regulators are believed to regulate Acr protein expression, and are commonly encoded within phage/prophage genomes by adjacent, small open reading frames. By using known Aca protein sequences as bioinformatic search queries, additional Aca proteins have been identified. Many of these newly identified Aca genes are encoded by bacteriophages infecting species with Type I CRISPR-Cas systems. Small, previously uncharacterized open reading frames found adjacent to aca genes were shown to possess anti-CRISPR activity against Type I-F and I-E systems.

In one embodiment, the present invention contemplates a composition comprising an aca gene within a *Brackiella oedipodis* genome. In one embodiment, the *Brackiella oedipodis* genome comprises a Type II-C CRISPR-Cas locus. Although it is not necessary to understand the mechanism of an invention, it is believed that the *Brackiella oedipodis* Type II-C CRISPR-Cas locus is the category that includes NmeCas9, and is not analogous to a Type I CRISPR-Cas locus. In fact, it has been determined that the *Brackiella oedipodis* Cas9 locus is ~47% identical to NmeCas9.

Furthermore, it has been found that the *B. oedipodis* Aca protein is adjacent to an uncharacterized ORF that encodes a candidate Acr protein (Acr1Bo). In one embodiment, the present invention contemplates a plurality of Type-II Aca genes located within a plurality of phages, each of which is adjacent to small uncharacterized ORF that encodes a candidate Acr protein, for example:

1. *Brackiella oedipodis* Acr (Acr1Bo)

Open Reading Frame (276 Nucleotides):

(SEQ ID NO: 1)

```
ATGaaagaggtatttaaattaaaaccagagctagtgacttataaaggttg
cggctgggcactggcgtgcatcaaagacggagagatcatcgatctcacct
acgttcgtgaccttggtattgaagaatatgatgaaaacttcgatggcctt
gaacctgaaatcatctattacgatgttgtggcttctcaagcgtgcaaaga
agtcgcctatcgttatgaagaaatgggcgaatttaccttcggcttatgct
cgtgttgggaattcaatgtaatgTAG
```

Protein (91 Amino Acids):

(SEQ ID NO: 2)

```
MKEVFKLKPELVTYKGCGWALACIKDGEIIDLTYVRDLGIEEYDENFDGL
EPEIIYYDVVASQACKEVAYRYEEMGEFTFGLCSCWEFNVM
```

2. *Neisseria meningitidis* Acr #1 (Acr1Nm)

Open Reading Frame (258 Nucleotides):

(SEQ ID NO: 3)

```
ATGaataaaacttataaaattggaaaaaatgccgggtatgatggctgcgg
tctttgtcttgcggccatttctgaaaatgaagctatcaaagttaagtatt
tgcgcgacatttgtcctgattacgatggcgatgataaagctgaggattgg
ctgagatggggaacggacagccgcgtcaaagcagccgctcttgaaatgga
gcagtacgcatatacgtcggttggtatggcctcatgttgggagtttgttg
aactaTGA
```

Protein (85 Amino Acids):

(SEQ ID NO: 4)

```
MNKTYKIGKNAGYDGCGLCLAAISENEAIKVKYLRDICPDYDGDDKAEDW
LRWGTDSRVKAAALEMEQYAYTSVGMASCWEFVEL
```

3. *Neisseria meningitidis* Acr #2 (Acr2 Nm)

Open Reading Frame (372 Nucleotides):

(SEQ ID NO: 5)

```
ATGagcaaaaacaatattttcaacaagtatccaacaattattcacggcga
agcgcgggggagaatgacgaatttgtggtgcatacgcgctacccgcgat
tcttggcgcggaaatcttttgacgacaatttcacgggcgaaatgcctgca
aaacctgttaacggggaattgggacaaatcggcgaaccgcgccgccttgc
ttatgattcacggcttggtttgtggctttctgacttcatcatgttggaca
acaacaagccgaaaaacatggaggattggcttgggcaattaaaagccgcc
tgcgatcgaatcgcggcggatgatttgatgctgaatgaagatgcggcgga
tttggagggctgggatgatTGA
```

Protein (123 Amino Acids):

(SEQ ID NO: 6)

```
MSKNNIFNKYPTIIHGEARGENDEFVVHTRYPRFLARKSFDDNFTGEMPA
KPVNGELGQIGEPRRLAYDSRLGLWLSDFIMLDNNKPKNMEDWLGQLKAA
CDRIAADDLMLNEDAADLEGWDD
```

4. *Neisseria meningitidis* Acr #3 (Acr3 Nm)

Open Reading Frame (351 Nucleotides):

(SEQ ID NO: 7)

```
ATGttcaaacgcgctattatcttcacttctttcaacggctttgaaaaagt
ttctcgaactgaaaaacgccgccttgccaaaatcatcaatgctcgagttt
ccatcatcgacgaatacttgagagccaaagacaccaacgcatcgcttgac
ggtcagtaccgcgctttcttgttcaacgacgaatcgcccgcaatgaccga
atttctggcaaaacttaaagcctttgccgaaagttgcaccggaatcagca
tcgacgcatgggaaattgaagaaagcgaatacgtccgcctgccggtggaa
cgcagggatttcttagcggcagccaacggcaaagagatttttaaaattTA
A
```

Protein (116 Amino Acids):

(SEQ ID NO: 8)

MFKRAIIFTSFNGFEKVSRTEKRRLAKIINARVSIIDEYLRAKDTNASLD

GQYRAFLFNDESPAMTEFLAKLKAFAESCTGISIDAWEIEESEYVRLPVE

RRDFLAAANGKEIFKI

5. *Neisseria meningitidis* Acr #4 (Acr4 Nm)
Open Reading Frame (267 Nucleotides)

(SEQ ID NO: 9)

ATGgcaaaaggtagaacaagcattacagagcggctcaaaaagagccaaaa acgagaggcgcgccgtgatatggcgcacgaatgggcggaaaaatgggagc aggattatttgagcctgctctctcaaatcaaacaggcaatcagcaaagga cacgatgacgagcttatcgacttatttgctgatttacgcgcgctgcaaca gccaaaatttgaggcattgcatcgagtgattgatgagcttatcacgccga cacgggagcttataTGA Protein (88 Amino Acids)

(SEQ ID NO: 10)

MAKGRTSITERLKKSQKREARRDMAHEWAEKWEQDYLSLLSQIKQAISKG

HDDELIDLFADLRAL QQPKFEALHRVIDELITPTRELI

6. *Neisseria meningitidis* Acr #5 (Acr5 Nm)
Open Reading Frame (192 Nucleotides)

(SEQ ID NO: 11)

ATGaaatacgccaaatcaaaatctatcagcaaaatcggtcaatatcatca aacttttaaaatcctttgggataaactaccaaaagaattgattgagaaat caacagccaaaaatctcgccattattattgatttgatgtatgagcaaaaa gaatatggccatacagaggcatggcgcgaattaacatcaTAA Protein (63 Amino Acids)

(SEQ ID NO: 12)

MKYAKSKSISKIGQYHQTFKILWDKLPKELIEKSTAKNLAIIIDLMYEQK

EYGHTEAWRELTS

7. *Ralstonia solanacearum* Acr (Acr6Rs)
Open Reading Frame (312 Nucleotides)

(SEQ ID NO: 13)

ATGtacgcaatctacacggacgcaggaatcctggcagtagcccccactgt ggaggcagcgatcgaacgggccaggtgcgagcatgggctaaaagccgctc ttgtggctcagaacacgagctgcatctaccacggcgggatcgttgatttg accactgcatggcgaatctctgccgattcagagcgagccggagattcgga gacgaaattgcgccgctgctcggcgcgcttggcggcagcagtagaggctg ggcgacttcccgtgttcgctgtgatggcgcatggcgagttagatctaatc gaggatgccTGA Protein (103 Amino Acids)

(SEQ ID NO: 14)

MYAIYTDAGILAVAPTVEAAIERARCEHGLKAALVAQNTSCIYHGGIVDL

TTAWRISADSERAGDSETKLRRCSARLAAAVEAGRLPVFAVMAHGELDLI

EDA

8. *Pseudomonas aeruginosa* Acr (Acr7 Pa)
ORF (261 Nucleotides)

(SEQ ID NO: 15)

ATGctggagcgatgcctccagattgtcaccacgccgggcgctgtgccccg agatcaggcggaggccaacgtttgccgtttggccgggatgatcgtggacg gcaggtatccagtggcaggcaaacgactgtctgatgcggctgcgacctac tttgccgaccatccagagcagcaagtgccgtccgccgaggtcgcccggcg cggctggatcataaacgccccacgcctccggacgcgactggagcgcctgc tgggcgggTAA Protein (86 Amino Acids)

(SEQ ID NO: 16)

MLERCLQIVTTPGAVPRDQAEANVCRLAGMIVDGRYPVAGKRLSDAAATY

FADHPEQQVPSAEVARRGWIINAPRLRTRLERLLGG

9. *Haemophilus parainfluenzae* Acr (AcrIIC4Hpa)
ORF (267 Nucleotides):

(SEQ ID NO: 22)

ATGaagatcaccagcagcaacttcgcgaccattgcgaccagcgagaactt tgcgaagctgagcgtgctgccgaaaaaccaccgtgagccgatcaagggtc tgttcaaaagcgcggttgaacagtttagcagcgcgcgtgacttctttaag aacgagaactacagcaaagagctggcggaaaagttcaacaaagaagcggt gaacgaggcggttgaaaagctgcaaaaagcgatcgatctggcggaaaaac agggcattcaatttTGA Protein (88 Amino Acids)

(SEQ ID NO: 23)

MKITSSNFATIATSENFAKLSVLPKNHREPIKGLFKSAVEQFSSARDFFK

NENYSKELAEKFNKEAVNEAVEKLQKAIDLAEKQGIQF

10. *Simonsiella muelleri* Acr (AcrIIC5s&.)
ORF (393 Nucleotides):

(SEQ ID NO: 24)

ATGaacaacagcatcaagttccacgtgagctacgacggtaccgcgcgtgc gctgtttaacaccaaggagcaggcggaaaaatactgcctggttgaggaaa ttaacgatgagatgaacggctataagcgtaaaagctgggaggaaaagctg cgtgaggaaaactgcgcgagcgtgcaggactgggttgagaagaactacac cagcagctatagcgacctgttcaacatctgcgagattgaagtgagcagcg cgggtcaactggttaagatcgacaacaccgaggtggacgatttcgttgaa aactgctatggctttaccctggaggacgatctggaggaattcaacaaggc gaaacagtacctgcaaaaattttatgcggagtgcgaaaacTGA Protein (130 Amino Acids):

(SEQ ID NO: 25)
MNNSIKFHVSYDGTARALFNTKEQAEKYCLVEEINDEMNGYKRKSWEEKL

REENCASVQDWVEKNYTSSYSDLFNICEIEVSSAGQLVKIDNTEVDDFVE

NCYGFTLEDDLEEFNKAKQYLQKFYAECEN

In one embodiment, the present invention contemplates a composition comprising a Type II CRISPR-Cas9 inhibitor (e.g., an Acr). In one embodiment, the Type II Acr is Acr1Bo, that inhibits a Type II-C CRISPR-Cas system. In one embodiment, the Type II Acr is derived from an *N. meningitidis* strain. In one embodiment, the present invention contemplates a Type II Acr including, but not limited to, AcrIIC1Boe, AcrIIC1Nme, AcrIIC2Nme, AcrIIC3Nme, AcrIIC4Hpa, and AcrIIC5Smu. The data presented herein demonstrates that the Type II Cas9 inhibitors AcrIIC1Boe, AcrII1Nme, AcrIIC2Nme, AcrIIC3Nme, AcrIIC4Hpa, and AcrIIC5Smu control *N. meningitidis* CRISPR-Cas system immune function.

Tests and readouts for NmeCas9 editing, including inactivation of fluorescent reporter genes, as well as standard T7E1 assays (e.g. in the attached figures) to detect the introduction of genomic lesions have already been established. For the latter, HEK293T cells were transiently transfected with plasmids encoding NmeCas9 (fused to epitope tags and nuclear localization sequences) and sgRNAs that target sites adjacent to a functional protospacer adjacent moiety (PAM), usually NNNNGATT, though some variations from that consensus are permissible. Zhang et al., "DNase H activity of *Neisseria meningitidis* Cas9" *Molecular Cell* 60:242-255 (2015); and Hou et al., "Efficient genome engineering in human pluripotent stem cells using Cas9 from *Neisseria meningitidis*" *Proc Natl. Acad Sci. USA* 110:15644-15649 (2013).

Representative genomic target sites used in these preliminary experiments are as follows, showing the entire PCR amplicon:

24-nt NmeCas9 target spacer: Bold
20-nt Spy target spacer: *Italic*
Protospacer Adjacent Moiety: Underlined (NNNNGAT (A/T) for NmeCas9; NGG for SpyCas9)

Target Site N-TS3

(SEQ ID NO: 17)
CATTTCTTTATATGTCTTAATGCTGACCTTCTGCACAAATGCACCACTAT
ACCATTACCAGTTATTACCAGCTAATAGGGTGGGAGCTAATGAACACTTA
CAACTCTGTCCTCAGGAAAGTGCAGAGAAATTCATGCATCCCAGGAGGGG
ATGCTCAGAAAGAGGAAGCTGGTTTATGATTGGACTGCGTGGGCGTTTGC
AAAGCAAGGTTTCATTGAAAAGAGATGTTTTCTTGTGGGGCATTTGAGTC
AATTACCAAAGTCTATTTTTAAAACTTCTCCATATGAGCCTGATCTATCT
CTGAAGTTGTTTTGAAGACCACAGGACTGCTTGTAACATGTGCCATTGCC
ATTCTGCTTTTTATTCTTTTGATTGGAAGGACTAAAATGATTTTCACTTA

Target Site N-TS7

(SEQ ID NO: 18)
GGACAGAAGAGAGTAGGGAGACGAGAAGGCGGAGGACAGAAGAAATGGGG
GAGAGGGAAGAGGACAGAGAGGCTGCGCGCCTCTGAATACGCCAAGTCCA
GCAGAGCTGGAGGCCTGTGAGAGGAGCTGCAAGCTTGAGCAAAGG*GAGAG*
*AGGTGAGCGGATGAA*GGGAGATTGGTGAGTATCCGCCCACGCACCTACTT
GTAAAAAGATCAAGGGGAAACACGCAGAAGGTCCCGCGGGAGTCCTGTGA
CCCACGTGAGGTGCTCGTGCCAGCGCGGGGTGGGAGGTGGTGGGCAATGT
TCGTCGTGGAGTTGAGGAAGAAATTCTCCAGCCTTAAGGAAGCAAAAGAG
TTCAAAGATCAGTGAGGCTGCTCAACAGAGGGATATGCAGATGACAGAAT
GC

Target Site N-TS25

(SEQ ID NO: 19)
GCAATCCACCCAATGCTAACTGGGATGTTTGATTTTGCAGCCTCTTTCAG
AGCAGTTGCTAAAAGTGGCTCCACATCATAAGAGGGCTTCCCTCCCTCAA
TCCATGAGAGCAACTAGGTTTTGCATCAGTGAAAGGAAGAAAAAGCAGGA
GTTTGGCAAGAGGCTGCAAAGAGACGGCACTGGGCTCCACTAGAGTTCCT

-continued
TCCCACCGCGTTTCTCATCCTGTCTTCTGCCTAGTGGATATGTCTGCGTG
GGCGTGCACACACATTGGCTGATGAAACCCCCTTCCTGTTGCACAGGGTC
AGAACTAAGCGAGGTGGGTGTAGCTTTGGAGGGTTCTGAAATCTAAGAAC
CAGCTTCCTTTCCCACCGCTTTCCGCTGAGTCAGTTCACTGCAGAGTGCT
CTGCAGGATCTGGAGGCCTTTGTGTTCA Target Site D-TS3

(SEQ ID NO: 20)
GGACAAAAGCAGCCCATTAGGACCCCCCCACACTCGCACCTCTCCCTGCC
AAGACCTCTAGGAGCAGCAGGGCGGAGAGACAGAGCCTGCCGGTTGGCAT
GGAACAAACTGACT*GAAGGCGAGGTCCGGGGCGG*AGGGGATTGGGTTGTA
GGGCTGTGGAGGAGGGGCGGCGGAGGGGGCGCTGGGGCTCTCGCTTGCTT
CAGCCCAGCCCTTCTAGTCAGCCCGCGACAACTCGCGCCAGCTACGGGGC
CTCAGAGAAGCCGGACTTCGCAAGCACCATGCAGTGGATAAGGGGCGGAT
CGGGAATGGTGAGTGCATGTAACCTTGGCTTCCCTTGCTTGAGCCTCTCA
GTCCCCCAGCCCCACCTCCAGTTCCTCCAACGAGCCACAAGGCAGTGAGC
ACCCTGGCCTCTGCCCACCGCCCTAGCCGCCGTCCTTGAGACACCAGTGA
GCTTGCTGTGGCCATTTTAGGAGTCC

Target Site D-TS7

(SEQ ID NO: 21)
AGGACTGCTCTCAGCTACCGGCCTCCTCTGGATGACGGGACTGCAGGAAC
CACGAGAACCCCAGTTCTAGCTCCCGGGGTGGGCAGGCTGCTTGGCAGGC
AGGCCGCCTTCCCTCCACCAGGAGTCAGGTCTCCAGCCAGAGGTCCTGAC
CCAGGGCACAAGTGCTCGCACTGGGAAGCAGGCCTCTGAGGCAGGACGTC
TTCTCCTGTGGTGGAGTGGGGGTGTGGGCAGGGCAGGGAGGCCAGCAGAG
AGAGGCTCGGGGAGCAGGCTCTGTGGGCTTGCAGGAGGCAGGTCTGTGGC
CCCTCCCTGGACCCTAGCCTAATGCCCCCTGCACCCCATGCCTATGTTCC
AGCTTCCTGGGTCTGCAGGTCCAGCCGGCT*GGCACCCTCCATGTACCCA*
*G*GGGAGATTCCAGCCAGACACCCGCCCCCCGGCCCTGGCTAAGAAGTTGC
TTCCTGTTGCCAGCATGACCTACCCTCGCCTCTTTGATGCCATCCGCTGC
CACCTCCTTTTGCTCCTGGACCCTTTAGCCTCTCTGCCCTT

Genomic DNA was extracted and a fragment containing the target site was subjected to polymerase chain reaction amplification. The resultant amplicons were heat-denatured and re-annealed to form heteroduplexes. The heteroduplexes were then digested with T7E1 that cleaves DNA containing a mismatch or bulge. The amount of T7E1 digestion reflects the degree of heteroduplex formation, which in turn reflects the efficiency of mutagenesis at the target site by NmeCas9. The generated plasmids each expressed an Acr for testing. As a negative control, plasmids were generated that expressed a previously characterized, similarly sized Acr (Acr88a-32: 84 amino acids). Acr88a-32 specifically inhibits an unrelated Type I-E CRISPR-Cas system and would be expected to have no effect on any form of Cas9. Pawluk et al., "A new group of phage anti-CRISPR genes inhibits the Type I-E CRISPR-Cas system of *Pseudomonas aeruginosa*" *mBio* 5:e00896-14 (2014).

Each individual Acr was expressed from a separate plasmid, each in one of three forms: i) the native phage-encoded sequence (with no additional amino acids appended); ii) with an N-terminal fusion of a nuclear localization signal (NLS) and a FLAG epitope tag; and iii) with a C-terminal fusion of an NLS and a FLAG tag. Although it is not necessary to understand the mechanism of the invention, Acrs of between 85 to 123 amino acids are believed to be well below the size limit for passive protein diffusion through the nuclear pores.

The data presented herein shows that with an NmeCas9 target site N-TS3 15-20% editing efficiencies were observed during standard non-inhibited NmeCas9 editing assays. At one-half the relative amounts/ratios of transfected plasmids encoding Type II CRISPR-Cas inhibitor proteins, reasonably strong inhibitory effects were seen with untagged Acr1Bo and Acr1Nm, and mild effects are seen with untagged Acr2 Nm. Partial inhibitory effects were observed with tagged Acrs, especially C-terminally-tagged Acr1Bo ("Acr1Bo/Flag-NLS"). The negative control (Acr88a-32) has no consistent inhibitory effect. These results suggest that the putative Type II-C inhibitors limit NmeCas9 editing efficiency, but might need to be expressed in higher amounts (relative to NmeCas9) for full inhibition to be observed. The data also suggests that some of the tags might be compatible with Acr function. See, FIG. 1.

Figure 2:
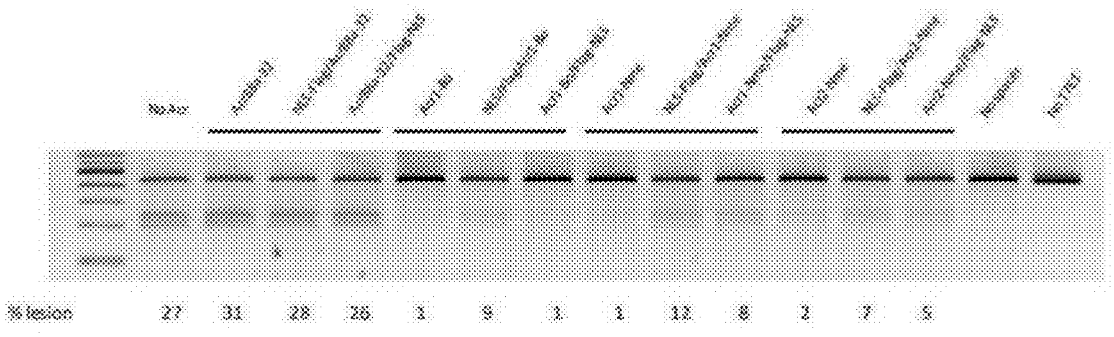
FIG. 2 presents exemplary data showing selective inhibition of NmeCas9 gene editing at the N-TS25 target site with several Acr proteins. NmeCas9+SgRNA plasmid (200 ng)+Acr plasmid (200 ng).
Figure 3:
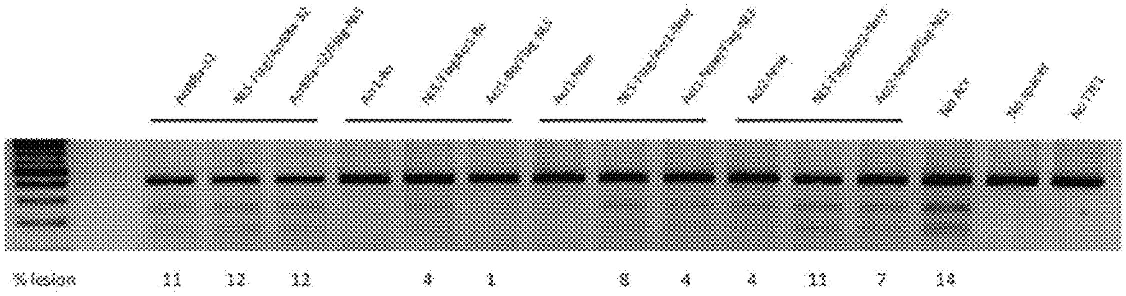
FIG. 3 presents exemplary data showing selective inhibition of NmeCas9 gene editing at the N-TS7 target site with several Acr proteins. NmeCas9+SgRNA plasmid (200 ng)+Acr plasmid (200 ng).

Additional tests with different target sites (e.g., N-TS25 and N-TS7) were performed with equivalent amounts of Acr plasmids that revealed robust NmeCas9 inhibition. All three untagged Acr proteins were strongly inhibitory, as was a C-terminally-tagged Acr1 Bo. Other tagged Acrs showed partial effects, whereas the negative control Acr88a-32 is non-functional. See FIGS. 2 and 3, respectively.

Figure 4:
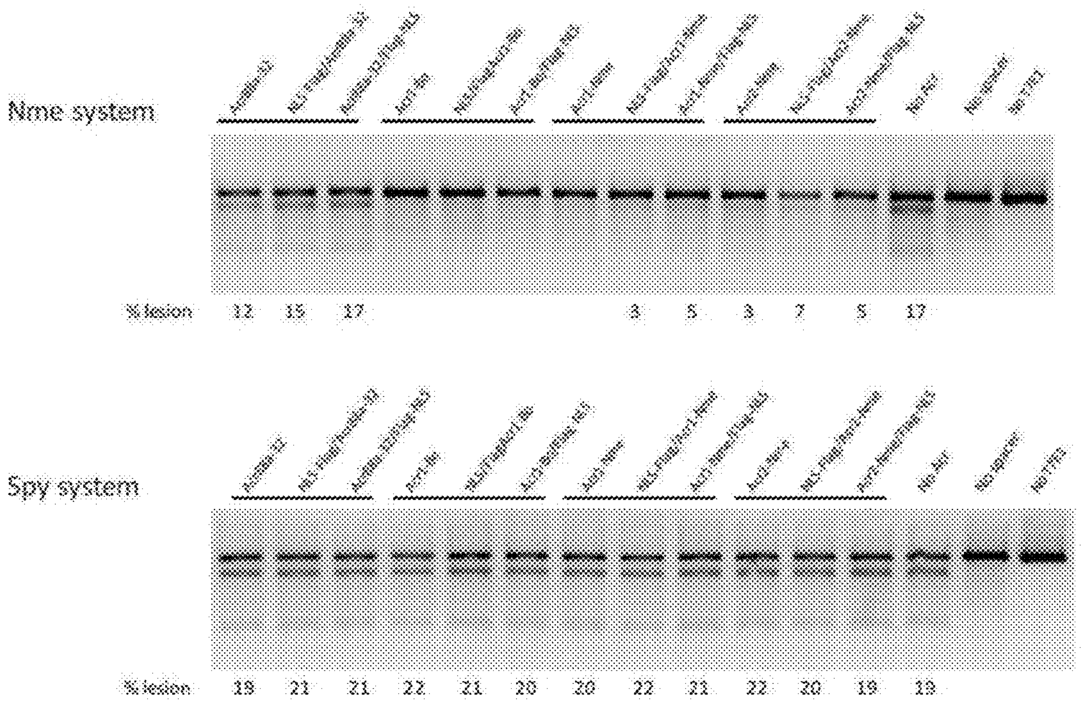
FIG. 4 presents exemplary data showing selective inhibition of NmeCas9 (Type II-C) gene editing versus SpyCas9 (Type II-A) gene editing at the D-TS7 dual target site with several Acr proteins (both tagged and untagged). Nme/Spy Cas9+SgRNA plasmid (150 ng)+Acr plasmid (100 ng).

A "dual" target site was edited (e.g., D-TS7) where "dual" refers to the fact that the site can be targeted by either SpyCas9 (Type II-A) or NmeCas9 (Type II-C). The capacity for dual targeting results from the fact that dual site flanking sequences (e.g., for example, GGGAGATT) matches the NGG PAM consensus for SpyCas9, as well as the NNNN-GATT PAM consensus for NmeCas9. Therefore, this similarity allows a direct comparison of the relative inhibitory effects of Acr proteins on SpyCas9 and NmeCas9 on the exact same site, under otherwise equivalent conditions. Also, SpyCas9 and NmeCas9 expression constructs were used that had identical promoters, terminal fusions, etc. to facilitate direct comparisons. The results show that various Type II Acr inhibitors demonstrated strong inhibition of NmeCas9 editing activity, but no inhibition of SpyCas9 activity at the same site. This shows that the Type II Acr inhibitors (both tagged and untagged) are likely specific for Type II-C systems and cannot function on the distantly related Type II-A system. See, FIG. 4. A second dual target site, D-TS3, was tested using only untagged Acrs showing similar results. See, FIG. 5.

Figure 6:
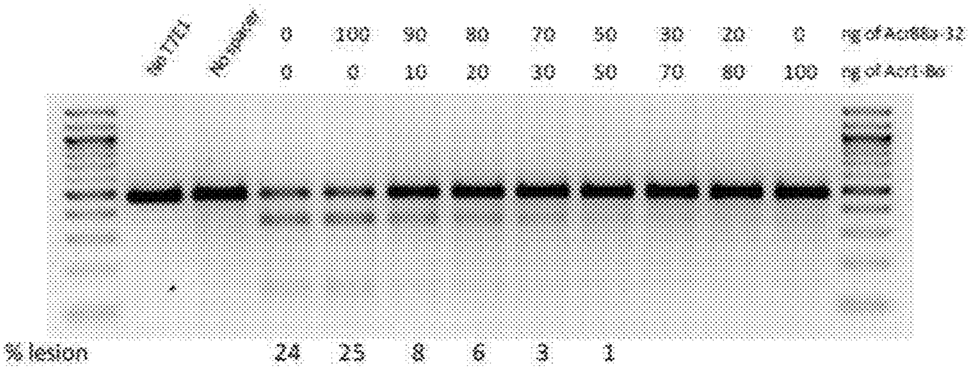
FIG. 6 presents exemplary data showing a dose response relationship of Acr1Bo inhibition of NmeCas9 (Type II-C) gene editing at the D-TS3 target site. NmeCas9+SgRNA plasmid (150 ng)+Acr plasmid (150 ng).
Figure 7:
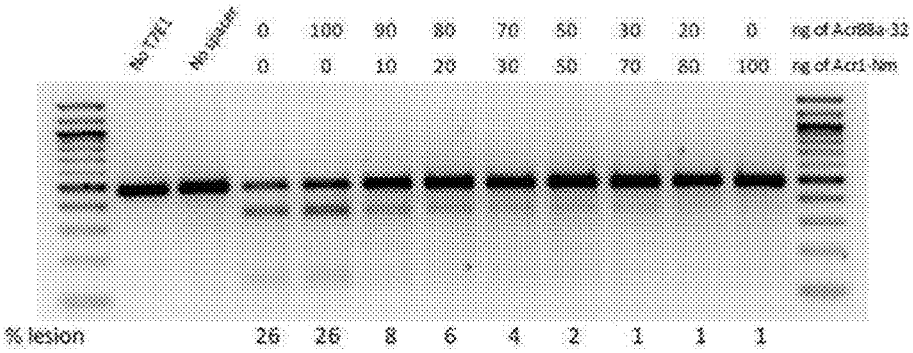
FIG. 7 presents exemplary data showing a dose response relationship of Acr1Nm inhibition of NmeCas9 (Type II-C) gene editing at the D-TS3 target site. NmeCas9+SgRNA plasmid (150 ng)+Acr plasmid (150 ng).
Figure 8:
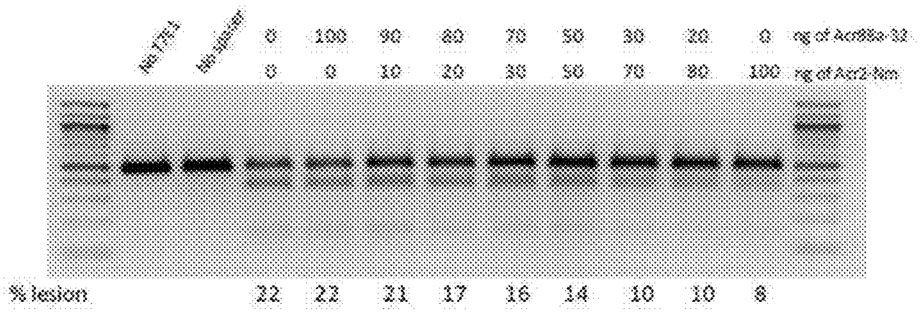
FIG. 8 presents exemplary data showing a dose response relationship of Acr2 Nm inhibition of NmeCas9 (Type II-C) gene editing at the D-TS3 target site. NmeCas9+SgRNA plasmid (150 ng)+Acr plasmid (150 ng).

Further tests using NmeCas9 editing of the D-TS3 target site with either untagged Acr1Bo, Acr1Nm, or Acr2 Nm shows that the inhibitory effect of these Acrs on NmeCas9 editing is dose-dependent. See, FIGS. 6, 7 and 8, respectively. The inhibitory effects of both Acr1Bo and Acr1Nm were observed to be complete. However, the inhibitory effect of Acr2 Nm was incomplete.

Figure 5:
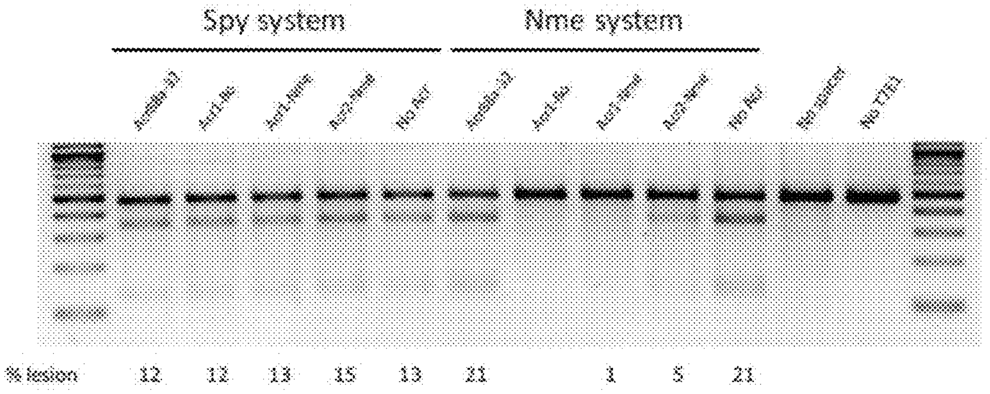
FIG. 5 presents exemplary data showing selective inhibition of NmeCas9 (Type II-C) gene editing versus SpyCas9 (Type II-A) gene editing at the D-TS3 dual target site with several Acr proteins (some untagged). Nme/Spy Cas9+SgRNA plasmid (150 ng)+Acr plasmid (100 ng).
Figure 9:
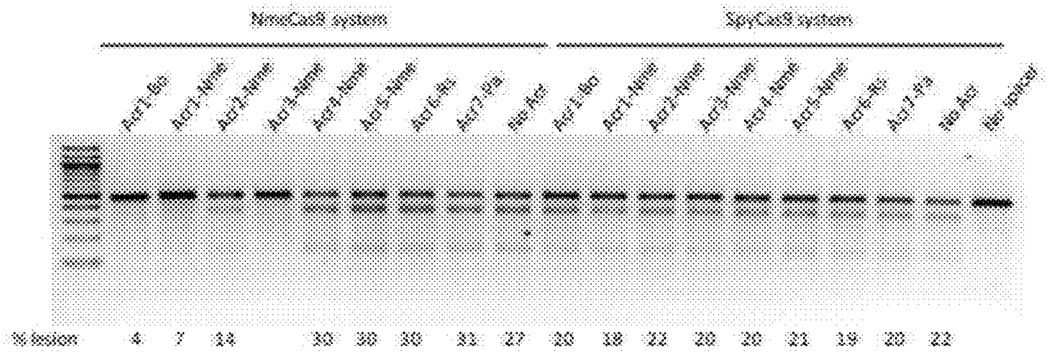
FIG. 9 presents exemplary data showing selective inhibition of NmeCas9 (Type II-C) gene editing versus SpyCas9 (Type II-A) gene editing at the D-TS3 dual target site with several Acr proteins (complete untagged set). Nme/Spy Cas9+SgRNA plasmid (150 ng)+Acr plasmid (100 ng).

The dual target site, D-TS3 was tested with complete set of untagged Acrs, unlike the above data presented in FIG. 5. The tests reveal Acr3 Nm to be an effective NmeCas9 inhibitor, while having no effect on SpyCas9 inhibition. See FIG. 9.

Figure 10:
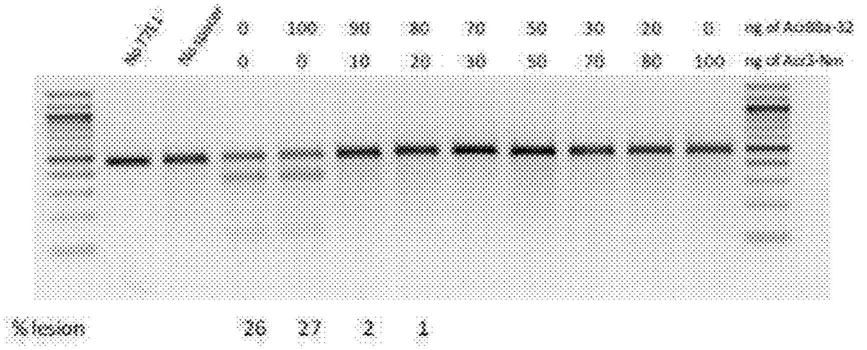
FIG. 10 presents exemplary data showing a dose response relationship of Acr3 Nm inhibition of NmeCas9 (Type II-C) gene editing at the D-TS3 target site. NmeCas9+SgRNA plasmid (150 ng)+Acr plasmid (150 ng).

FIG. 10 presents exemplary data showing a dose response relationship of Acr1Bo inhibition of NmeCas9 (Type II-C) gene editing at the D-TS3 target site. NmeCas9+SgRNA plasmid (150 ng)+Acr plasmid (150 ng).

A dose response relationship between Acr3 Nm and NmeCas9 editing of the D-TS3 target site shows that complete inhibition occurs even with very small amounts of transfected Acr3 Nm plasmid, suggesting that Acr3 Nm may be a particularly potent inhibitor. See, FIG. 10.

In conclusion, these data demonstrate that various NmeCas9 inhibitors can prevent NmeCas9 gene editing activity in human cells. Although it is not necessary to understand the mechanism of the invention, it is believed that these Acr inhibitors represent Cas9 genome editing "off-switches".

A. Truncated Acr Proteins

In one embodiment, the present invention contemplates a truncated nucleic acid sequence encoding an Acr protein derived from the group including, but not limited to, SEQ ID NO: 1, SEQ ID NO: 3, SEQ ID NO: 5, SEQ ID NO: 7, SEQ ID NO: 9, SEQ ID NO: 11, SEQ ID NO: 13 and SEQ ID NO: 15.

In one embodiment, the present invention contemplates an Acr protein comprising a truncated amino acid sequence derived from the group including, but not limited to, SEQ ID NO: 2, SEQ ID NO: 4, SEQ ID NO: 6, SEQ ID NO: 8, SEQ ID NO: 10, SEQ ID NO: 12, SEQ ID NO: 14 and SEQ ID NO: 16.

B. Acr Dimer Proteins

In one embodiment, the present invention contemplates a homodimer Acr protein selected from the group including, but not limited to, (SEQ ID NO: 2)-(SEQ ID NO: 2), (SEQ ID NO: 4)-(SEQ ID NO: 4), (SEQ ID NO: 6)-(SEQ ID NO: 6), (SEQ ID NO: 8)-(SEQ ID NO: 8), (SEQ ID NO: 10)-(SEQ ID NO: 10), (SEQ ID NO: 12)-(SEQ ID NO: 12), (SEQ ID NO: 14)-(SEQ ID NO: 14), and/or (SEQ ID NO: 16)-(SEQ ID NO: 16).

In one embodiment, the present invention contemplates a heterodimer Acr protein comprising at least two different sequences selected from the group including, but not limited to, SEQ ID NO: 2, SEQ ID NO: 4, SEQ ID NO: 6, SEQ ID NO: 8, SEQ ID NO: 10, SEQ ID NO: 12, SEQ ID NO: 14, and/or SEQ ID NO: 16.

In one embodiment, the present invention contemplates a heterodimer Acr protein selected from the group including, but not limited to, (SEQ ID NO: 2)-(SEQ ID NO: 4), (SEQ ID NO: 2)-(SEQ ID NO: 6), (SEQ ID NO: 2)-(SEQ ID NO: 8), (SEQ ID NO: 2)-(SEQ ID NO: 10), (SEQ ID NO: 2)-(SEQ ID NO: 12), (SEQ ID NO: 2)-(SEQ ID NO: 14), and/or (SEQ ID NO: 2)-(SEQ ID NO: 16).

In one embodiment, the present invention contemplates a heterodimer Acr protein selected from the group including, but not limited to, (SEQ ID NO: 4)-(SEQ ID NO: 6), (SEQ ID NO: 4)-(SEQ ID NO: 8), (SEQ ID NO: 4)-(SEQ ID NO: 10), (SEQ ID NO: 4)-(SEQ ID NO: 12), (SEQ ID NO: 4)-(SEQ ID NO: 14), and/or (SEQ ID NO: 4)-(SEQ ID NO: 16).

In one embodiment, the present invention contemplates a heterodimer Acr protein selected from the group including, but not limited to, (SEQ ID NO: 6)-(SEQ ID NO: 8), (SEQ ID NO: 6)-(SEQ ID NO: 10), (SEQ ID NO: 6)-(SEQ ID NO: 12), (SEQ ID NO: 6)-(SEQ ID NO: 14), and/or (SEQ ID NO: 6)-(SEQ ID NO: 16).

In one embodiment, the present invention contemplates a heterodimer Acr protein selected from the group including, but not limited to, (SEQ ID NO: 8)-(SEQ ID NO: 10), (SEQ ID NO: 8)-(SEQ ID NO: 12), (SEQ ID NO: 8)-(SEQ ID NO: 14), and/or (SEQ ID NO: 8)-(SEQ ID NO: 16).

In one embodiment, the present invention contemplates a heterodimer Acr protein selected from the group including, but not limited to, (SEQ ID NO: 10)-(SEQ ID NO: 12), (SEQ ID NO: 10)-(SEQ ID NO: 14), and/or (SEQ ID NO: 10)-(SEQ ID NO: 16).

In one embodiment, the present invention contemplates a heterodimer Acr protein selected from the group including, but not limited to, (SEQ ID NO: 12)-(SEQ ID NO: 14), and/or (SEQ ID NO: 12)-(SEQ ID NO: 16).

In one embodiment, the present invention contemplates a heterodimer Acr protein of (SEQ ID NO:14)-(SEQ ID NO:16).

Figure 16:
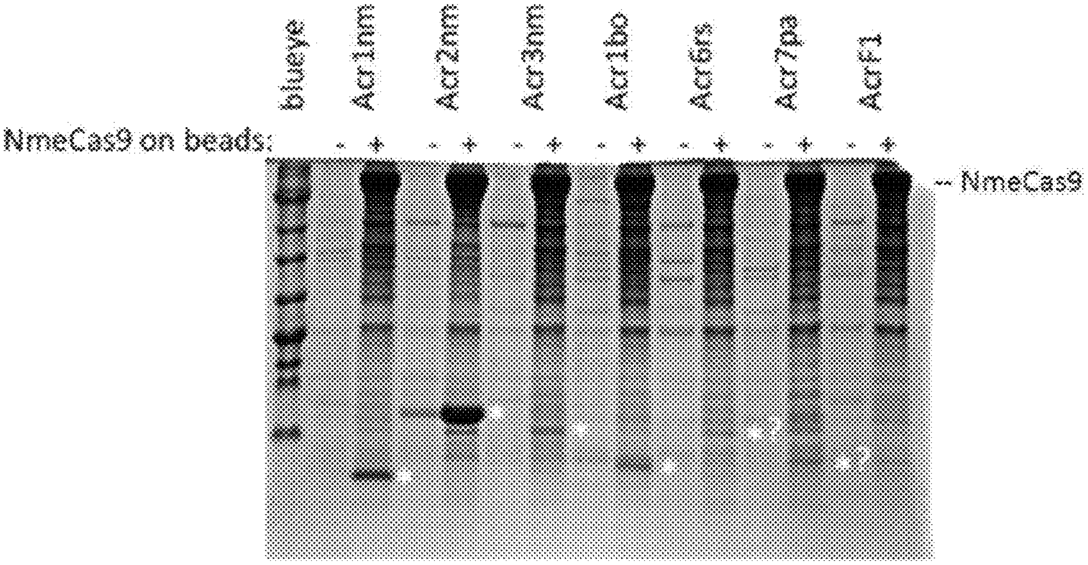
FIG. 16 presents exemplary data showing direct binding of Acr proteins with a Cas9 protein. In particular, a Coomassie-stained SDS-PAGE analysis shows binding interactions between NmeCas9 and Acr1Nm, Acr2 Nm, Acr3 Nm, and Acr1Bo (indicated with *), with possible preliminary evidence for interactions between NmeCas9 and Acr6rs and Acr7pa (indicated with *?). AcrF1, a type I-F anti-CRISPR, is used as a negative control.
Figure 17:
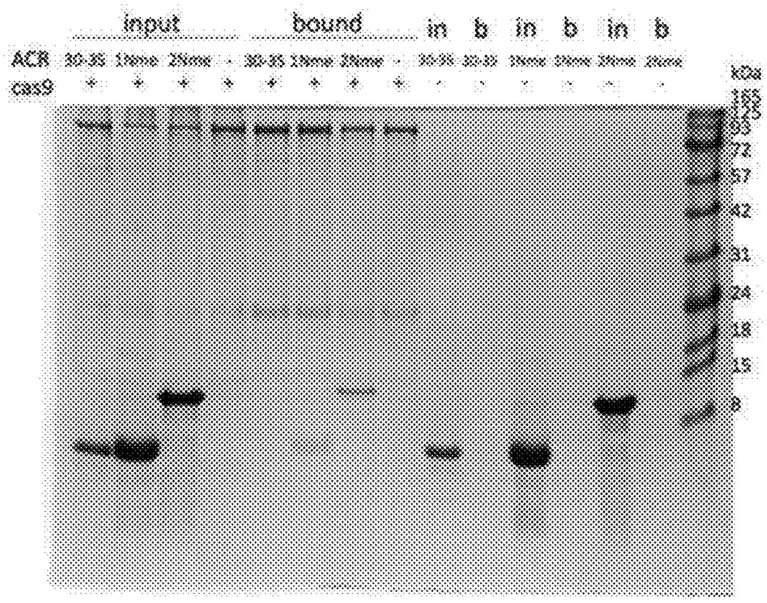
FIG. 17 presents exemplary data showing direct binding of Acr proteins with a NmeCas9 protein. Input (i.e. total protein) and elution fractions are shown. AcrF1 (labelled here as 30-35), a type I-F anti-CRISPR, is used as a negative control.
Figure 18:
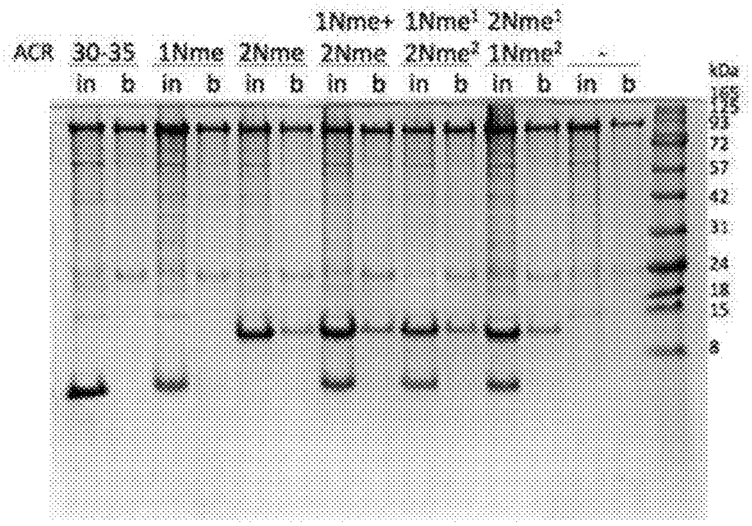
FIG. 18 presents exemplary data showing the simultaneous, non-competitive, binding of Acr1Nm and Acr2 Nm to a NmeCas9 protein.

The data presented herein demonstrate a direct binding of several Acrs to NmeCas9, as well as data suggesting that Acr1Nm and Acr2 Nm can simultaneously bind to NmeCas9. For example, *E. coli* lysates containing untagged, overexpressed anti-CRISPR proteins were incubated with Ni-NTA resin alone (−) or Ni-NTA resin with 6×His-tagged NmeCas9 bound (+) and the resultant elution fractions were analyzed by SDS-PAGE followed by Coomassie staining. See FIG. 16. A direct interaction between Acr1Nm and Acr2Nnm with NmeCas9 was also shown using purified, untagged anti-CRISPR proteins mixed with Ni-NTA resin alone (−) or Ni-NTA resin with 6×His-tagged NmeCas9 bound (+), with the input and resultant elution fractions analyzed by Coomassie-stained SDS-PAGE. See FIG. 17. Although it is not necessary to understand the mechanism of an invention, it is believed that a fusion protein comprising the active binding sites of Acr1Nm and Acr2 Nm would act synergistically to provide improved gene editing than would be expected from either Acr alone or a mere additive function of being used simultaneously as separate proteins. This is because Acr1Nm and Acr2 Nm are shown herein to simultaneously bind to NmeCas9. Ni-NTA resin with 6×His-NmeCas9 bound was incubated with purified, untagged Acr2 Nm followed by Acr1Nm, or vice versa. The amount of each Acr eluted with NmeCas9 was not decreased when NmeCas9 was pre-bound with the other Acr. See FIG. 18. Therefore, this data suggests that Acr1Nm and Acr2 Nm do not compete to bind NmeCas9 and that they bind distinct, non-overlapping sites on the NmeCas9 protein. Although it is not necessary to understand the mechanism of an invention, it is believed that these data raise the possibility that a combination of Acr1Nm and Acr2 Nm would have a synergistic effect on NmeCas9 activity than either Acr alone.

C. Acr Fusion/Adduct Proteins

In one embodiment, the present invention contemplates an Acr fusion protein. In one embodiment, the fusion protein comprises a nuclear localization sequence. In one embodiment, the fusion protein comprises a epitope sequence tag. In one embodiment, the epitope sequence tag is FLAG (e.g., DYKDDDDK) (SEQ ID NO: 98).

Figure 11A:
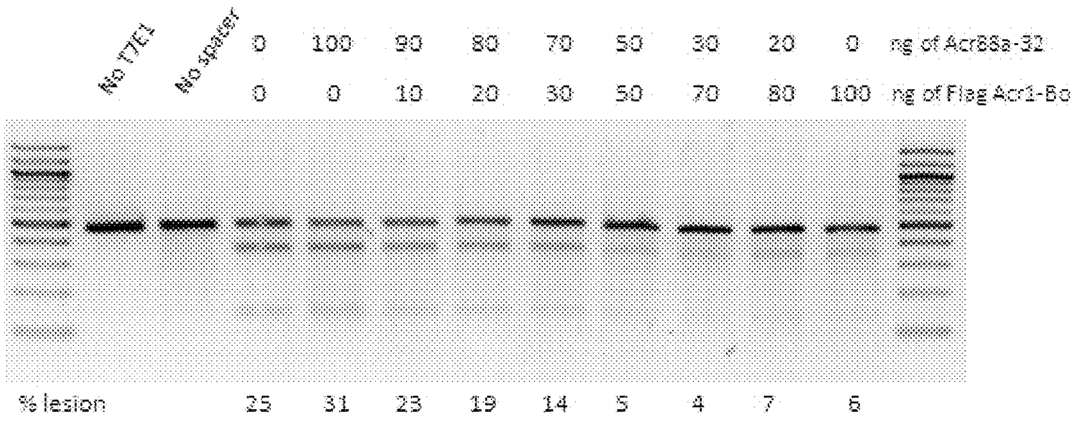
FIG. 11A-B presents exemplary data showing a titration of tagged Acr1Bo DTS3 site editing with Acr88-32 as a negative control using 150 ng Cas9/150 ng SgRNA.
Figure 11B:
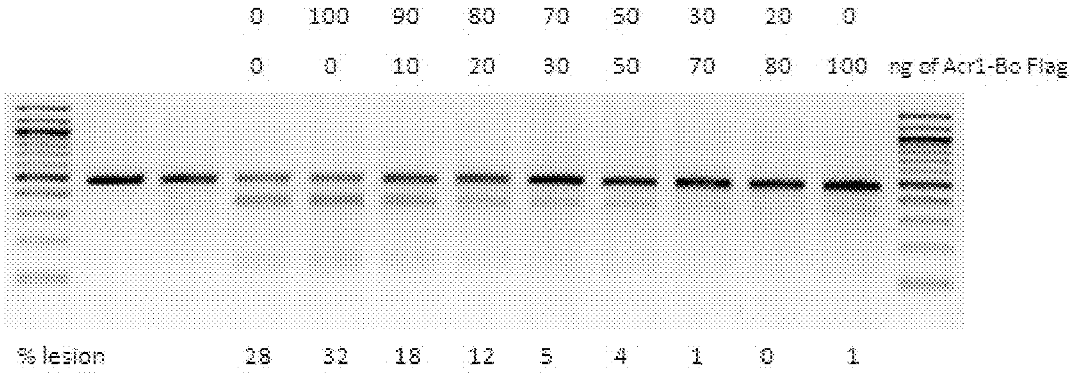
Figure 12A:
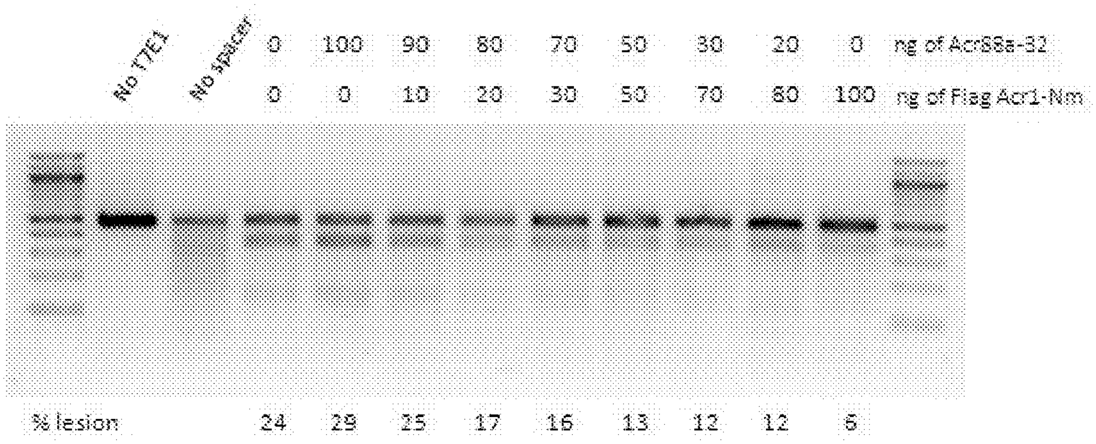
FIG. 12A-B presents exemplary data showing a titration of tagged Acr1Nm DTS3 site editing with Acr88-32 as a negative control using 150 ng Cas9/150 ng SgRNA.
Figure 12B:
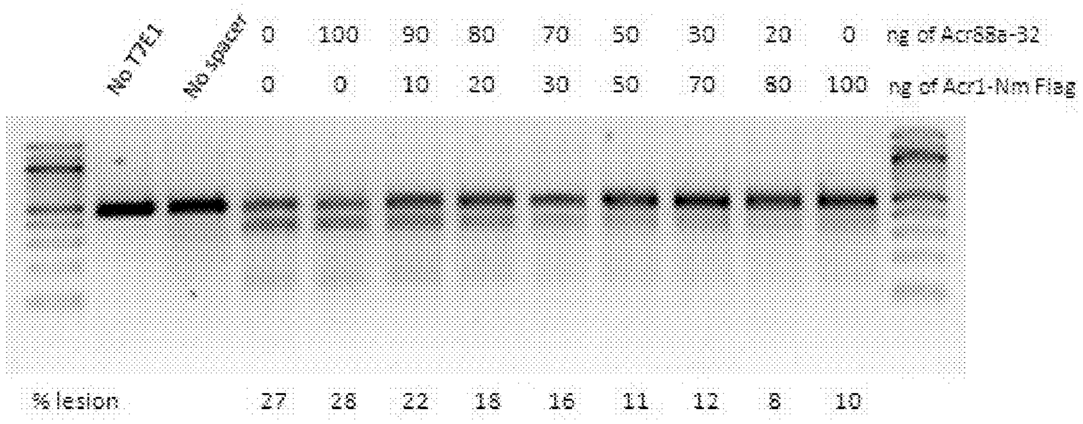
Figure 13A:
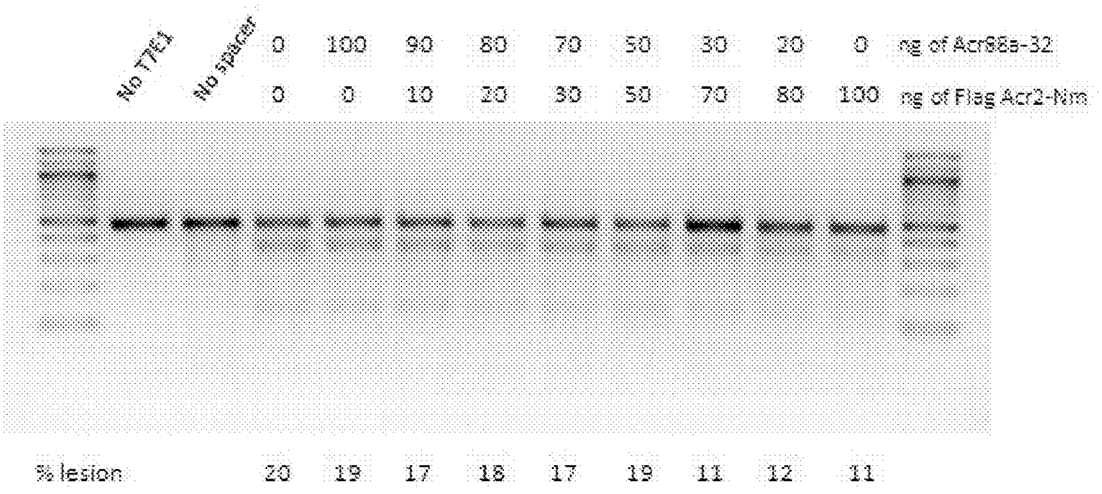
FIG. 13A-B presents exemplary data showing a titration of tagged Acr2 Nm DTS3 site editing with Acr88-32 as a negative control using 150 ng Cas9/150 ng SgRNA.
Figure 13B:
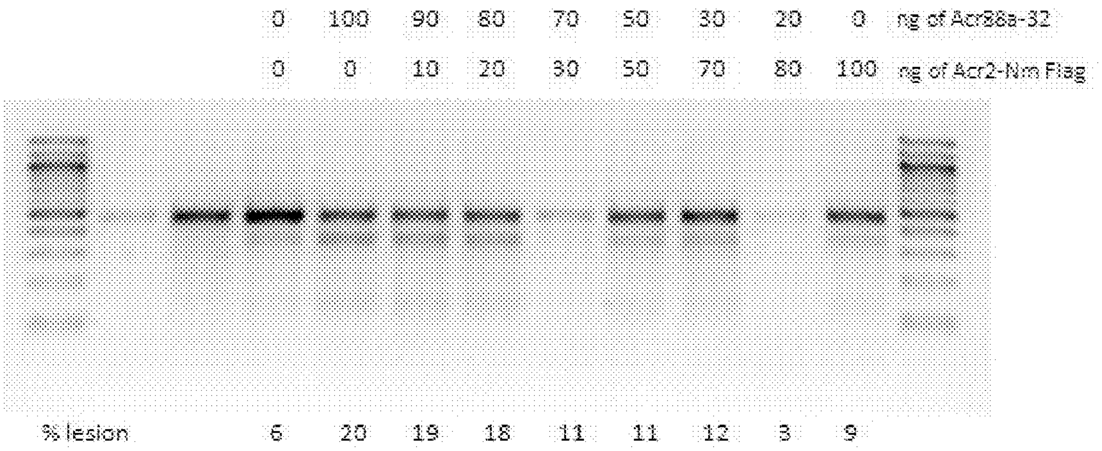
Figure 14A:
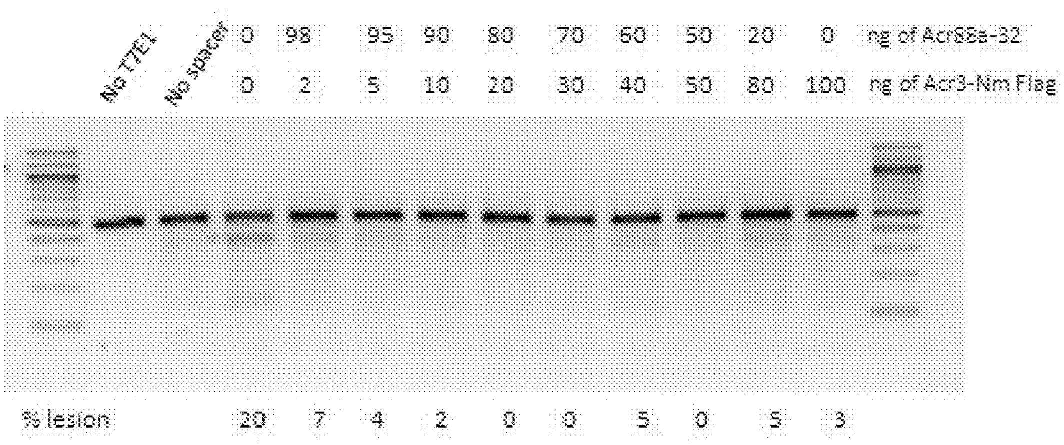
FIG. 14A-B presents exemplary data showing a titration of tagged Acr3 Nm DTS3 site editing with Acr88-32 as a negative control using 150 ng Cas9/150 ng SgRNA.
Figure 14B:
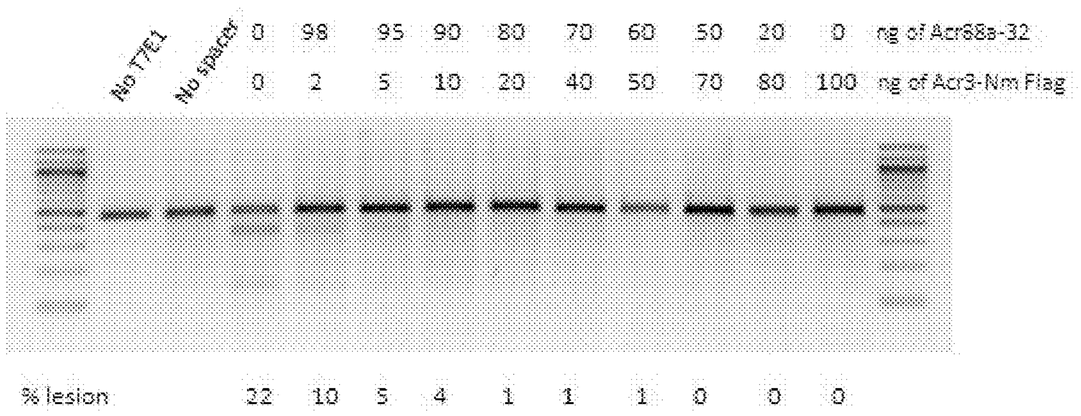
Figure 15A:
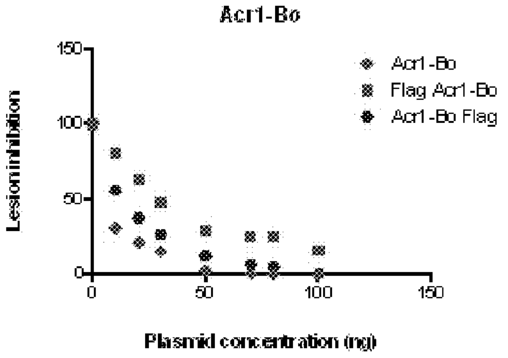
FIG. 15A-D presents a quantitative summary of the titration data showing that Acr adduct proteins (e.g., FLAG tagged) have similar activities as compared to Acr proteins without an adduct.
Figure 15B:
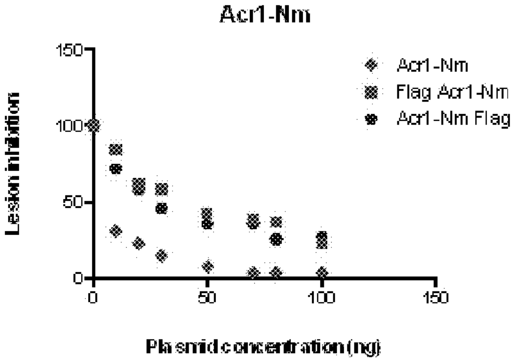
Figure 15C:
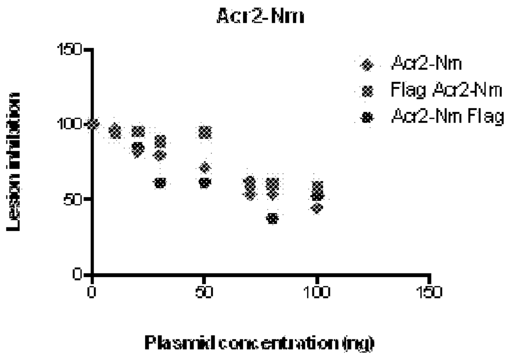
Figure 15D:
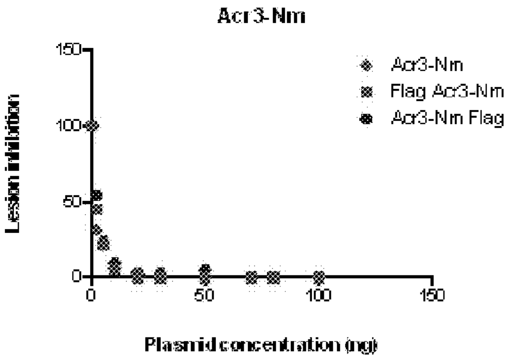

The data presented here demonstrates that FLAG-tagged Acr proteins have similar gene editing inhibitory activity as an Acr protein without a FLAG tag. For example, a titration of FLAG-tagged Acr proteins were assayed with the negative control Acr88-32 protein. The data further demonstrated similar activity whether the FLAG tag was attached to either the C-terminal or N-terminal end. For example, the gene editing of Acr1Bo was similar when attached at either the C-terminal or N-terminal end. See, FIG. 11A and FIG. 11B. Similar data was shown for Acr1Nm, Acr2 Nm and Acr3 Nm. See, FIGS. 12A/B, 13A/B and 14A/B, respectively. These data are quantitated and summarized. See, FIGS. 15A-15D.

D. Acr Mutated Proteins

In one embodiment, the present invention contemplates a mutated Acr protein. In one embodiment, the Acr protein comprises at least one non-wild type amino acid residue. In one embodiment, the Acr protein comprises at least two non-wild type amino acid residues. In one embodiment, the Acr protein comprises at least three non-wild type amino acid residues. In one embodiment the non-wild type amino acid residue represents an $AA^{WT}$→Ala mutation. In one embodiment, the non-wild type amino acid residue represents a Cys→Arg mutation. In one embodiment, the non-wild type amino acid residue represent a Phe→Ser mutation.

III. Methods of Using Type II Cas9 Inhibitor Compositions

In one embodiment, the present invention contemplates a method for controlling Cas9 genome editing and/or genome binding that provides a limitation on Cas9 activity. In one embodiment, the controlling is a limitation on Cas9 activity duration. In one embodiment, the controlling is a limitation on Cas9 activity efficiency. In one embodiment, the controlling is a limitation on Cas9 activity spatial extent. In one embodiment, the controlling is a limitation on Cas9 activity tissue specificity. In one embodiment, the controlling is a limitation on Cas9 activity environmental condition.

A. Biological Therapeutics

In one embodiment, the present invention contemplates a method for treating and/or preventing disease. In one embodiment, the disease is a mammalian disease. In one embodiment, the mammalian disease is a human disease. In one embodiment, the mammalian disease is a livestock disease. In one embodiment, the disease is an avian disease. In one embodiment, the disease is an agricultural product disease.

1. Minimization of Off-Target Effects

In one embodiment, the present invention contemplates a method of controlling Cas9 activity duration. For example, Cas9/sgRNA could be delivered into a cell, allowed to function for a predetermined duration that was shown empirically to yield efficient on-target editing, and then inactivated through the delivery of the Acr protein.

2. Control of Spatial Activity

In one embodiment, the present invention contemplates a method of controlling Cas9 spatial activity providing a Cas9 having at least two tissue or cell type specific activities and at least one Acr inhibitor selective for at least one of the plurality of tissue or cell type specific activities. Although it is not necessary to understand the mechanism of an invention, it is believed that Cas9 spatial control by using Acr inhibitors would permit administration of a Cas9 having multiple tissue or cell type specific activities, where simultaneous administration of Acrs selective for unwanted tissue/cell type activity would result in Cas9 activity on only a selected subset of possible cell types or tissues.

B. Gene Drives

In one embodiment, the present invention contemplates a method for controlling Cas9-based "gene drives" to modify the genomes of entire populations of organisms for potentially beneficial purposes. Examples include, but are not limited to: i) preventing the spread of genes in insect vectors of infectious disease (malaria, dengue, etc.); ii) preventing the ability of a general population to act as a host for a pathogen; or iii) rendering a specific population sub-fertile or even sterile.

However, uncontrolled gene drives have the potential for negative unintended consequences of ecosystem-wide genetic modification. anti-CRISPR proteins could possibly be used as an "antidote" that could slow the further spread of an "out-of-control" gene drive, in the event that negative unintended consequences become apparent. For instance, if a Cas9 gene drive is engineered into e.g. the mosquito *Aedes aegypti*, another population of *A. aegypti* could be generated that expresses the Acr protein, and held in reserve for later release into the same population, if needed. The Acr-expressing population would be gene drive-resistant.

IV. Acr Proteins as CRISPR-Cas9 "Off-Switches"

Although it is not necessary to understand the mechanism of an invention, it is believed that CRISPR-Cas9 technology would be enhanced by an ability to inhibit Cas9 function spatially, temporally, or conditionally. As discussed above, small proteins encoded by bacteriophages have been shown to inhibit the CRISPR-Cas systems of host bacteria. These "anti-CRISPRs" were specific to type I CRISPR-Cas systems that do not employ the Cas9 protein. In some embodiments, the present invention contemplates a plurality of Cas9 inhibitors. For example, the data presented herein suggest at least three distinct families of anti-CRISPR proteins that specifically inhibit the CRISPR-Cas9 system of *Neisseria meningitidis*. As shown, these anti-CRISPR proteins bind directly to *N. meningitidis* Cas9 (NmeCas9), and can be used as potent inhibitors of genome editing, for example, in human cells. These anti-CRISPR proteins are the first known "off-switches" for CRISPR-Cas9 activity, and they provide a genetically encodable means to inhibit CRISPR-Cas9 genome editing in eukaryotes.

In one embodiment, the present invention contemplates a method comprising CRISPR-Cas9 mediated genome editing for clinical therapeutics. For example, Cas9 is a nuclease that can be programmed with a guide RNA molecule to cut nearly any desired DNA sequence (Gasiunas et al., 2012; Jinek et al., 2012), enabling mutagenesis or editing at the site of cleavage (Cho et al., 2013; Cong et al., 2013; Hwang et al., 2013; Jiang et al., 2013; Jinek et al., 2013; Mali et al., 2013). This RNA-guided DNA editing technology has been suggested for development to provide personalized gene therapy to correct inherited disease, for sequence-specific targeting of pathogens to treat infectious disease, and many other applications (Bikard et al., 2014; Ebina et al., 2013; Gomaa et al., 2014; Kaminski et al., 2016; Ousterout et al., 2015; Wu et al., 2013; Yin et al., 2014).

Although the utility of Cas9 DNA targeting is widely acknowledged, there are currently limited means to exert control over Cas9 activity once it has been activated or delivered, leading to practical difficulties and safety concerns that are of importance in a clinical setting. For example, off-target effects (cleavage and mutation at unintended, near-cognate genomic sites) are exacerbated by excessive or prolonged Cas9 activity (Fu et al., 2014; Hsu et al., 2013; Pattanayak et al., 2013). Many potential therapeutic applications of CRISPR-Cas9 require editing at specific target tissues. Consequently, collateral Cas9 activity in ancillary tissues is at best useless and at worst a safety risk. For example, when zygotic injections of CRISPR Cas9 components are used to generate mutant animals, Cas9 activity after the initial rounds of mitosis can give rise to mosaic genotypes (Wang et al., 2013; Yen et al., 2014). Alternately, precise Cas9 gene editing involves homology-dependent repair (HDR). Because HDR pathways are suppressed during the G1 phase of the cell cycle, Cas9 activity during G1 increases the background of undesired imprecise edits. (Orthwein et al., 2015)) Recently, CRISPR-Cas9 gene drives (supra) have been developed, in part to advance the long-term goal of eradicating disease vectors such as mosquitos (Gantz et al., 2015; Hammond et al., 2016). A danger of this approach is that gene drives, once introduced into the environment, could be difficult to restrain, and could have unpredictable ecological consequences. Based on these and other considerations, the performance and safety of CRISPR-Cas9 applications could be greatly improved if Cas9 activity could be more effectively controlled. Several groups have devised methods to activate CRISPR Cas9 genome editing in response to specific cues, including light-inducible and drug-inducible Cas9 activity. (Nihongaki et al., 2015; Nunez et al., 2016; Wright et al., 2015). However, a robust, specific, and genetically-encodable "off-switch" for Cas9 activity has not yet been identified.

In one embodiment, the present invention contemplates CRISPR-Cas9 technologies that are derived from a type II CRISPR-Cas9 adaptive immune systems of bacteria. In one embodiment, a type II CRISPR-Cas9 complex can target and destroy foreign DNA entities such as bacteriophages (phages) and plasmids (Barrangou et al., 2007; Deltcheva et al., 2011). Although the Cas9 ortholog from *Streptococcus pyogenes* strain SF370 (SpyCas9, subtype II-A) is commonly used, type II CRISPR-Cas systems from several other bacterial species have also been adapted for eukaryotic genome editing (Makarova et al., 2015); Cong et al., 2013; Esvelt et al., 2013; Hirano et al., 2016; Hou et al., 2013; Lee et al., 2016; Muller et al., 2016; Ran et al., 2015). For example, a Cas9 from *Neisseria meningitidis* (NmeCas9; subtype II-C) may be an effective tool for human genome editing (Makarova et al., 2015; Esvelt et al., 2013; Hou et al., 2013; Lee et al., 2016). One advantage of NmeCas9 is because it prone to off-target effects (Esvelt et al., 2013; Hou et al., 2013; Lee et al., 2016). Alternatively a "Dead" NmeCas9 (dNmeCas9), in which nuclease active-site residues have been mutated, has also proven to be an effective, specific RNA-guided genome binding platform (Esvelt et al., 2013; Hilton et al., 2015; Kearns et al., 2015; Ma et al., 2015b). Similarly, dSpyCas9 and other nuclease-inactivated orthologs may also be useful in the presently disclosed invention. (Dominguez et al., 2016; Wang et al., 2016)).

A. *Neisseria Meningitidis* Anti-CRISPR Proteins

Preliminary studies characterized a conserved feature of anti-CRISPR (acr) genes as a downstream gene encoding a putative transcriptional regulator. For example, two distinct families were identified having helix-turn-helix (HTH) containing anti-CRISPR associated (Aca) proteins, which are referred to herein as Aca1 and Aca2. Identification of genes encoding Aca proteins in diverse bacterial species are also represented in five other families of type I-F acr genes encoded directly upstream of the aca genes. (Pawluk et al., 2016).

Figure 19A:
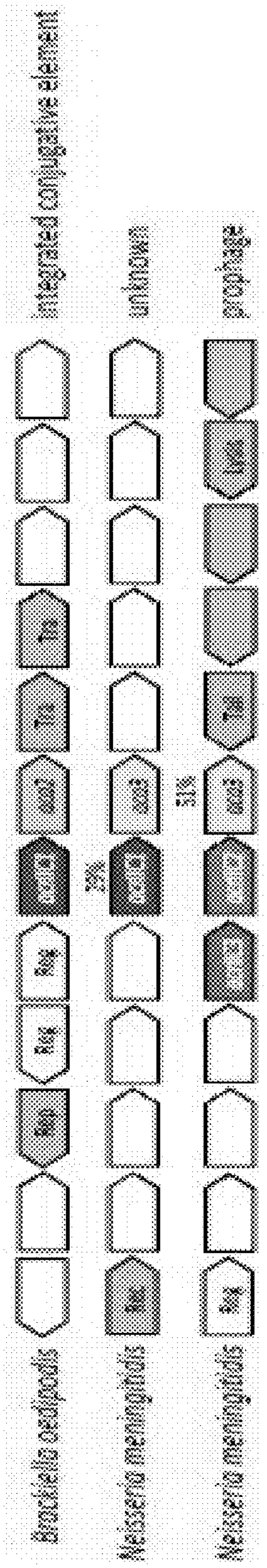
FIG. 19A-C presents illustrative embodiments regarding the identification and validation of type II-C anti-CRISPR proteins.
Figure 20:
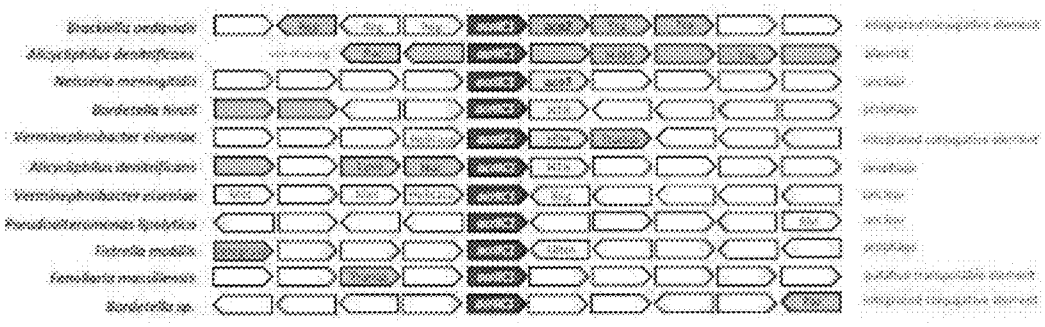
FIG. 20 presents a schematic of putative AcrIIC1 orthologs that are widely dispersed in MGEs of different species. The schematic representation of AcrIIC1 orthologs is identified by PSI-BLAST and their genomic contexts. The species in which each ortholog is found and its predicted genomic region classification (i.e., prophage, integrated conjugative element) are indicated. Gene arrows are not drawn to scale. Grey arrows represent genes that have a clear connection to mobile DNA; either by function (i.e. integrase) or by evidence of horizontal transfer as determined by BLAST search. Known, relevant gene functions are indicated by labels: Rep, plasmid replication protein; Reg, transcriptional regulator; Tra, conjugal transfer protein; Par, plasmid partitioning protein; H-NS, histone-like nucleoid-structuring protein; HTH, helix-turn-helix DNA-binding protein; Transp, transposase; Lysis, phage lysis cassette; Nuc, nuclease; Met, methyltransferase; RM, restriction modification system.

In one embodiment, the present invention contemplates a plurality of genes encoding inhibitors of type II CRISPR-Cas systems. In one embodiment, type II acrs are located upstream of aca genes in MGEs within species bearing type II systems. For example, an anti-CRISPR gene in a *Brackiella oedipodis* putative encodes a 91-residue hypothetical protein (accession WP_028357638.1) lying directly upstream of an aca2 gene. FIG. 19A. This putative anti-CRISPR possessed several orthologs encoded in MGEs of diverse Proteobacteria, and a distant, putative ortholog in a Firmicute, *Fenollaria massiliensis*. FIG. 20.

The data suggest that the most frequently observed homologs of the CRISPR-Cas system among these species was a type II-C homolog. In one embodiment, the present invention contemplates an anti-CRISPR family that inhibits the activity of one or more representative type II-C Cas9 orthologs.

*N. meningitidis* strain 8013 harbors a type II-C CRISPR-Cas system (Zhang et al., 2013; Zhang et al., 2015). Further, strains of *N. meningitidis* are among the genomes that contain an MGE encoding a member of this putative anti-CRISPR family. FIG. 19A, FIG. 20. Consequently, NmeCas9 was used to establish proof of principle for Type II Cas9 inhibitor proteins. See, Table 1 and Table 2.

TABLE 1

Representative Nucleotide And Amino Acid Sequences Of Type II NmeCas9 Inhibitor Proteins

| Anti-CRISPR | DNA sequence | Protein sequence | SEQ ID NO: |
|---|---|---|---|
| AcrIIC1$_{Boe}$ | ATGGCCAAGGAGGTCTTCAAGCTGAAGCCGGAGCTGGTGACGT ACAAGGGCTGCGGGTGGGCCCTGGCCTGCATCAAGGATGGCGA | MAKEVFKLKPELVTYKGCGWALACIK DGEIIDLTYVRDLGIEEYDENFDGLE | 26, 27 |

TABLE 1-continued

| Representative Nucleotide And Amino Acid Sequences Of Type II NmeCas9 Inhibitor Proteins | | | |
|---|---|---|---|
| Anti-CRISPR | DNA sequence | Protein sequence | SEQ ID NO: |
| | GATCATCGACCTGACCTACGTGCGTGACCTGGGCATCGAGGAG TACGATGAAAACTTCGACGGCCTGGAGCCGGAGATCATCTATT ACGACGTCGTCGCCTCGCAGGCGTGCAAGGAAGTGGCCTACCG CTATGAAGAGATGGGCGAATTCACCTTCGGCCTCTGCAGCTGC TGGGAATTCAACGTCATGTAA | PEIIYYDVVASQACKEVAYRYEEMGE PTFGLCSCWEFNVM | |
| AcrIIC1$_{Nme}$ | ATGGCCAATAAAACTTATAAAATTGGAAAAAATGCCGGGTATG ATGGCTGCGGTCTTTGTCTTGCGGCCATTTCTGAAAATGAAGC TATCAAAGTTAAGTATTTGCGCGACATTTGTCCTGATTACGAT GGCGATGATAAAGCTGAGGATTGGCTGAGATGGGGAACGGACA GCCGCGTCAAAGCAGCCGCTCTTGAAATGGAGCAGTACGCATA TACGTCGGTTGGTATGGCCTCATGTTGGGAGTTTGTTGAACTA TGA | MANKTYKIGKNAGYDGCGLCLAAISE NEAIKVKYLRDICPDYDGDDKAEDWL RWGTDSRVKAAALEMEQYAYTSVGMA SCWEFVEL | 28, 29 |
| AcrIIC2$_{Nme}$ | ATGGCCAGCAAAAACAATATTTTCAACAAGTATCCAACAATTA TTCACGGCGAAGCGCGGGGGGAGAATGACGAATTTGTGGTGCA TACGCGCTACCCGCGATTCTTGGCGCGGAAATCTTTTGACGAC AATTTCACGGGCGAAATGCCTGCAAAACCTGTTAACGGGGAAT TGGGACAAATCGGCGAACCGCGCCGCCTTGCTTATGATTCACG GCTTGGTTTGTGGCTTTCTGACTTCATCATGTTGGACAACAAC AAGCCGAAAAACATGGAGGATTGGCTTGGGCAATTAAAAGCCG CCTGCGATCGAATCGCGGCGGATGATTTGATGCTGAATGAAGA TGCGGCGGATTTGGAGGGCTGGGATGATTGA | MASKNNIFNKYPTIIHGEARGENDEF VVHTRYPRFLARKSFDDNFTGEMPAK PVNGELGQIGEPRRLAYDSRLGLWLS DFIMLDNNKPKNMEDWLGQLKAACDR IAADDLMLNEDAADLEGWDD | 30, 31 |
| AcrIIC3$_{Nme}$ | ATGGCCTTCAAACGCGCTATTATCTTCACTTCTTTCAACGGCT TTGAAAAAGTTTCTCGAACTGAAAAACGCCGCCTTGCCAAAAT CATCAATGCTCGAGTTTCCATCATCGACGAATACTTGAGAGCC AAAGACACCAACGCATCGCTTGACGGTCAGTACCGCGCTTTCT TGTTCAACGACGAATCGCCCGCAATGACCGAATTTCTGGCAAA ACTTAAAGCCTTTGCCGAAAGTTGCACCGGAATCAGCATCGAC GCATGGGAAATTGAAGAAAGCGAATACGTCCGCCTGCCGGTGG AACGCAGGGATTTCTTAGCGGCAGCCAACGGCAAAGAGATTTT TAAAATTTAA | MAFKRAIIFTSFNGFEKVSRTEKRRL AKIINARVSIIDEYLRAKDTNASLDG QYRAFLFNDESPAMTEFLAKLKAFAE SCTGISIDAWEIEESEYVRLPVERRD FLAAANGKEIFKI | 32, 33 |
| AcrE2 | ATGGCCAATACCTATCTCATCGACCCCCGCAAAAACAACGACA ACTCCGGCGAGCGCTTCACGGTTGACGCTGTCGACATTACAGC CGCCGCGAAGAGCGCAGCCCAACAGATTCTTGGCGAGGAATTC GAGGGCCTCGTATACCGTGAAACCGGGGAGAGTAACGGAAGTG GCATGTTCCAGGCCTACCACCACCTGCACGGCACTAACCGCAC GGAGACGACCGTTGGCTATCCGTTTCATGTAATGGAACTCTGA | MANTYLIDPRKNNDNSGERFTVDAVD ITAAAKSAAQQILGEEFEGLVYRETG ESNGSGMFQAYHHLHGTNRTETTVGY PFHVMEL | 34, 35 |

TABLE II

| Specifications For Type II NmeCas9 Inhibitor Proteins | | | | | | |
|---|---|---|---|---|---|---|
| Anti-CRISPR | Species | Genome region prediction | Accession II | % ID to * | Size (aa) | Tested? |
| AcrIIC1 | * *Brackiella oedipodis* | putative integrated conjugative element | WP_028357638.1 | 100 | 91 | Yes |
| | *Alicycliphilus denitirificans* | plasmid | ADV02121.1 | 26 | 92 | |
| | *Neisseria meningitidis* | unclear | WP_049360089.1 | 29 | 85 | Yes |
| | *Bordetella hinzii* | prophage | WP_032962436.1 | 29 | 87 | |
| | *Verminephrobacter eiseniae* | putative integrated conjugative plasmid | WP_041950174.1 | 23 | 103 | |
| | *Alicycliphilus denitirificans* | prophage | WP_013520332.1 | 28 | 133 | |
| | *Verminephrobacter eiseniae* | unclear | ABM59472.1 | 23 | 147 | |
| | *Pseudoaiteromonas lipolytica* | unclear | WP_036972373.1 | 30 | 117 | |
| | *Tistrellamobilis* | prophage | WP_014743597.1 | 32 | 85 | |
| | *Fenollaria massiliensis* | putative transposable element | WP_019214717.1 | 28 | 149 | |
| | *Bordetella* sp. | putative integrated conjugative plasmid | WP_019939893.1 | 29 | 87 | |
| AcrIIC2 | * *Neisseria maningitidis* | prophage | WP_042743678.1 | 100 | 123 | Yes |
| | *Neisseria maningitidis* | prophage | CWP55982.1 | 96 | 132 | |
| | *Neisseria maningitidis* | prophage | WP_061725849.1 | 96 | 123 | |
| | *Neisseria maningitidis* | prophage | WP_002212355.1 | 95 | 123 | |
| | *Neisseria maningitidis* | prophage | WP_021439709.1 | 94 | 123 | |
| | *Neisseria maningitidis* | prophage | WP_061695141.1 | 93 | 123 | |
| | *Neisseria maningitidis* | prophage | WP_002238681.1 | 92 | 123 | |
| | *Neisseria maningitidis* | prophage | WP_002231709.1 | 91 | 123 | |
| | *Neisseria maningitidis* | prophage | WP_061693463.1 | 90 | 123 | |

TABLE II-continued

| Specifications For Type II NmeCas9 Inhibitor Proteins | | | | | | |
|---|---|---|---|---|---|---|
| Anti-CRISPR | Species | Genome region prediction | Accession II | % ID to * | Size (aa) | Tested? |
| | *Neisseria maningitidis* | prophage | WP_061706309.1 | 90 | 123 | |
| | *Neisseria maningitidis* | prophage | WP_002255675.1 | 89 | 123 | |
| | *Neisseria maningitidis* | prophage | WP_061384810.1 | 89 | 123 | |
| | *Ralstonia solanacearum* | putative integrated conjugative element | WP_019718638.1 | 33 | 130 | |
| | *Ralstonia solanacearum* | putative integrated conjugative element | WP_011001812.1 | 32 | 130 | |
| | *Ralstonia solanacearum* | putative integrated conjugative element | AMP37321.1 | 32 | 130 | |
| | *Ralstonia syzygii* | unclear | CCA86204.1 | 32 | 130 | |
| | *Ralstonia solanacearum* | putative transposable element | WP_013212199.1 | 32 | 130 | |
| | *Cupriavidus basilensis* | unclear | WP_017226229.1 | 31 | 128 | |
| | *Ralstonia solanacearum* | putative transposable element | WP_014616771.1 | 31 | 130 | |
| | *Ralstonia solanacearum* | putative integrated conjugative element | WP_003265552.1 | 31 | 130 | |
| | *Ralstonia solanacearum* | putative integrated conjugative element | WP_013205753.1 | 31 | 130 | |
| | *Ralsronia mannitolilytica* | unclear | WP_045787125.1 | 31 | 130 | |
| | *Ralstonia pickettii* | unclear | WP_024975412.1 | 31 | 130 | |
| | *Ralstonia pickettii* | putative transposable element | WP_004634308.1 | 31 | 131 | |
| | *Ralstonia* sp. | unclear | WP_048932645.1 | 31 | 129 | |
| | *Ralstonia* sp. | unclear | WP_009240943.1 | 31 | 131 | |
| | *Ralstonia* sp. | putative integrated conjugative element | WP_021194849.1 | 31 | 129 | |
| | *Ralstonia* sp. | unclear | WP_039599631.1 | 31 | 129 | |
| | *Cupriavidus basilensis* | unclear | WP_006163540.1 | 30 | 128 | |
| | *Cupriavidus basilensis* | unclear | WP_043347745.1 | 30 | 128 | |
| | *Burkholderiaceae bacterium* | unclear | WP_045235538.1 | 30 | 128 | |
| | *Ralstonia* sp. | unclear | WP_027681138.1 | 30 | 131 | |
| | *Cupriavidus* sp. | unclear | WP_039006692.1 | 30 | 126 | |
| | *Cupriavidus* sp. | unclear | WP_066735805.1 | 29 | 130 | |
| | *Cupriavidus* sp. | unclear | WP_035835797.1 | 28 | 130 | |
| | *Cupriavidus* sp. | unclear | WP_019451860.1 | 28 | 130 | |
| | *Cupriavidus* sp. | unclear | WP_020202326.1 | 28 | 128 | |
| | *Cupriavidus pauculus* | unclear | WP_061960205.1 | 28 | 127 | |
| | *Cupriavidus metallidurans* | unclear | WP_011516945.1 | 28 | 130 | |
| | *Cupriavidus* sp. | unclear | WP_029046347.1 | 28 | 126 | |
| | *Cupriavidus nantongensis* | unclear | WP_062800778.1 | 28 | 126 | |
| | *Cupriavidus oxalaticus* | prophage | WP_063238209.1 | 28 | 126 | |
| | *Cupriavidus gilardii* | unclear | WP_053822121.1 | 27 | 127 | |
| | *Cupriavidus* sp. | unclear | WP_035882356.1 | 27 | 127 | |
| | *Cupriavidus* sp. | unclear | EKZ95749.1 | 27 | 130 | |
| | *Cupriavidus* sp. | unclear | WP_035818297.1 | 27 | 126 | |

Figure 19B:
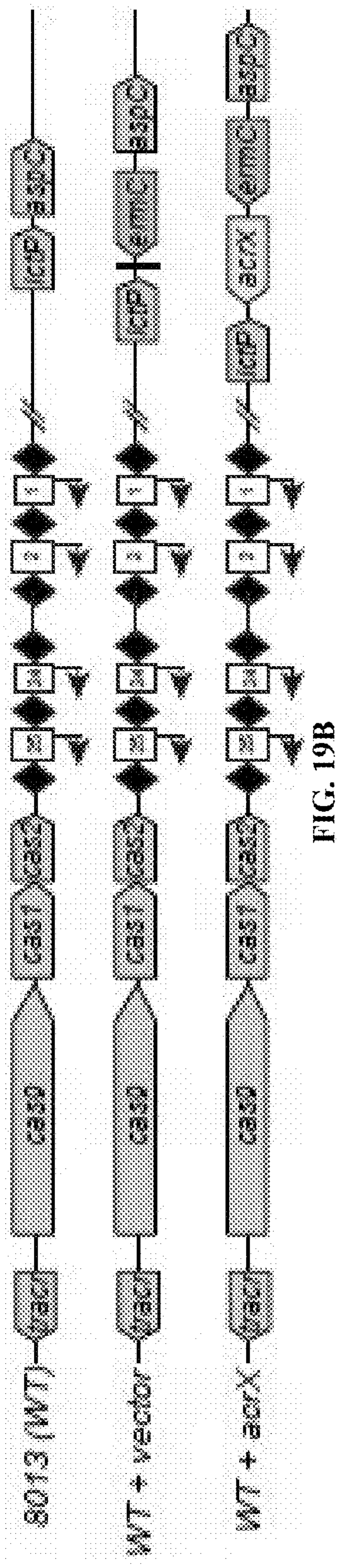
Figure 19C:
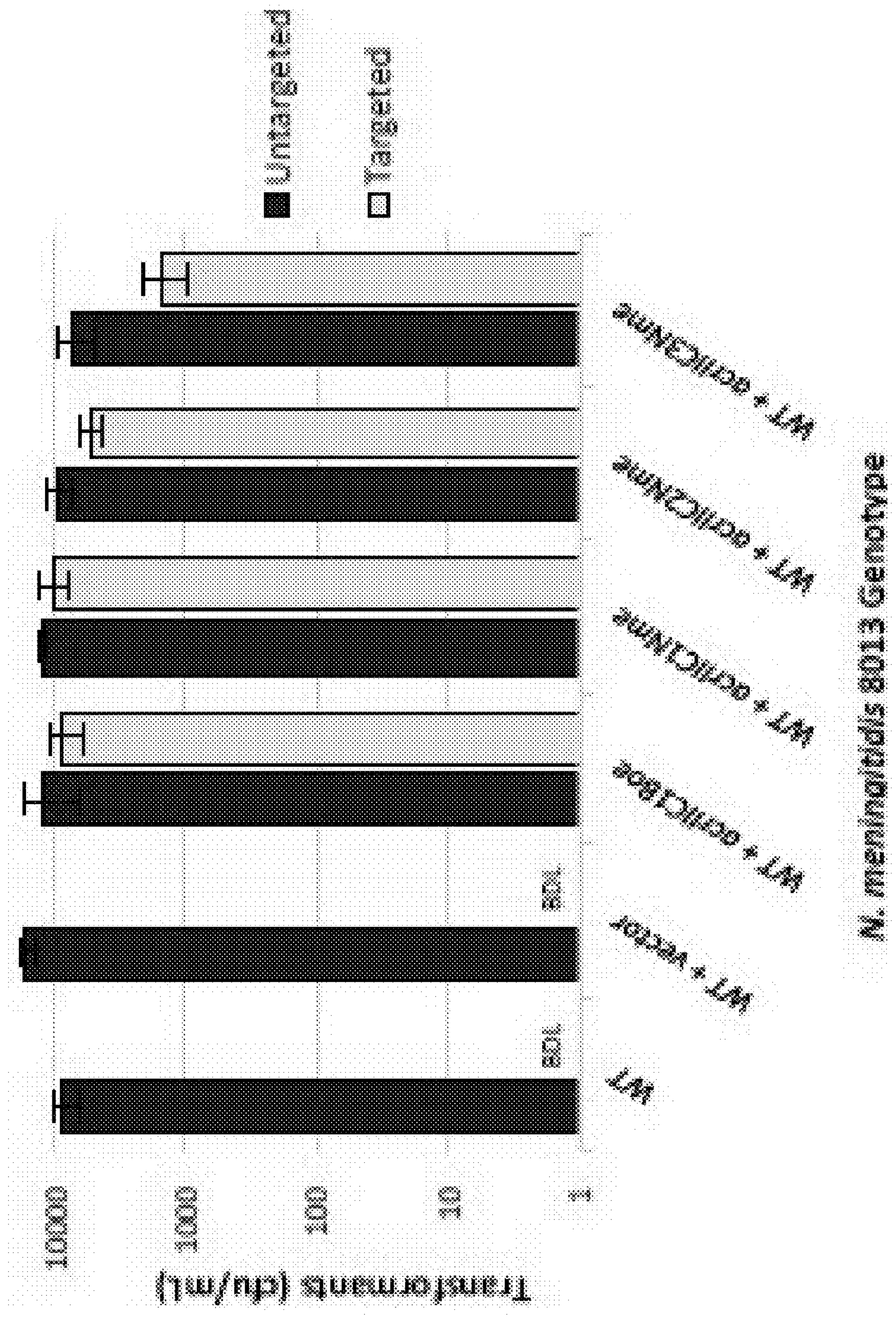

Candidate type II-C anti-CRISPR proteins from *B. oedipodis* and *N. meningitidis* genes to inhibit type II-C CRISPR-Cas activity was measured in their native context, using a previously described natural transformation assay in *N. meningitidis* 8013. FIG. 19A; Zhang et al., 2013; Zhang et al., 2015. In this assay, the transformation frequency of a plasmid bearing a CRISPR targeted protospacer sequence was compared to that of a control plasmid lacking the protospacer. A wild-type strain, as well as isogenic derivatives with an integrated, empty nics (e.g., an *Neisseria* intergenic complementation site), and either of the two candidate anti-CRISPR proteins were driven by a *N. meningitidis* cas9 promoter. FIG. 19B. In wild-type cells and the empty-vector control, robust type II-C CRISPR-Cas activity resulted in a ≥$10^4$-fold decrease in the transformation frequency of CRISPR-targeted DNA. Strikingly, expression of the putative anti-CRISPR proteins resulted in equal transformation frequencies when targeted or untargeted DNA was used, reflecting a lack of CRISPR interference. FIG. 19C.

These data showed that the type II-C CRISPR-Cas system of *N. meningitidis* was inhibited by proteins encoded by at least two putative anti-CRISPR genes, which are named herein acrIIC$1_{Boe}$ and acrIIC$1_{Nme}$. Although acrIIC$1_{Boe}$ has presumably evolved to inhibit the Cas9 ortholog found in *B. oedipodis* (BoeCas9), NmeCas9 is 47% identical to BoeCas9, suggesting that this similarity is sufficient to account for the observed cross-species inhibition. For the most part, the above identified acrIIC1 orthologs, except acrIIC$1_{Boa}$, were not found adjacent to aca1 or aca2 genes, but were instead encoded upstream of genes encoding distinct HTH-containing proteins. FIG. 19A-C, FIG. 20.

In one embodiment, the present invention contemplates a plurality of aca genes that encode a plurality of anti-CRISPR proteins. For example, two distinct genes were cloned that were located in a putative *N. meningitidis* prophage immediately upstream of the candidate aca3 gene. These genes also displayed robust anti-CRISPR activity and are referred to herein as acrIIC$2_{Nme}$ and acrIIC3$N_{Nme}$. FIGS. 19B and 19C; Table 1 and Table 2. These results demonstrate the existence of anti-CRISPR genes that are active against a type II CRISPR-Cas system.

B. Direct Interaction of Type II-C Anti-CRISPR Proteins with NmeCas9

Figure 21A:
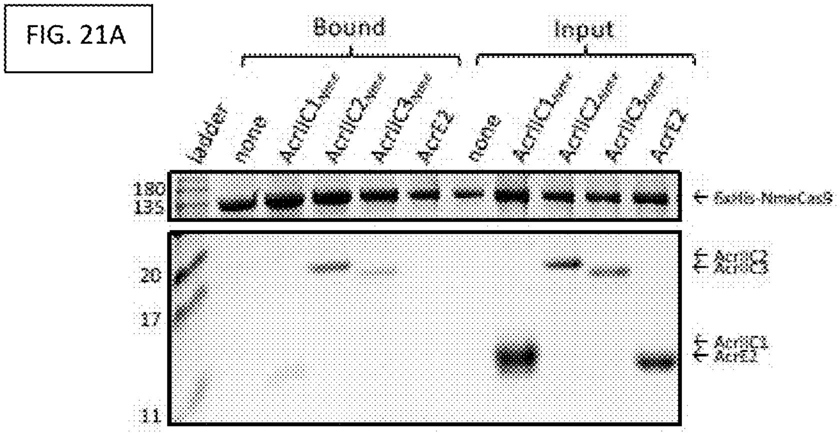
FIG. 21A-B presents exemplary data showing that anti-CRISPR proteins bind directly to NmeCas9:sgRNA.
Figure 21B:
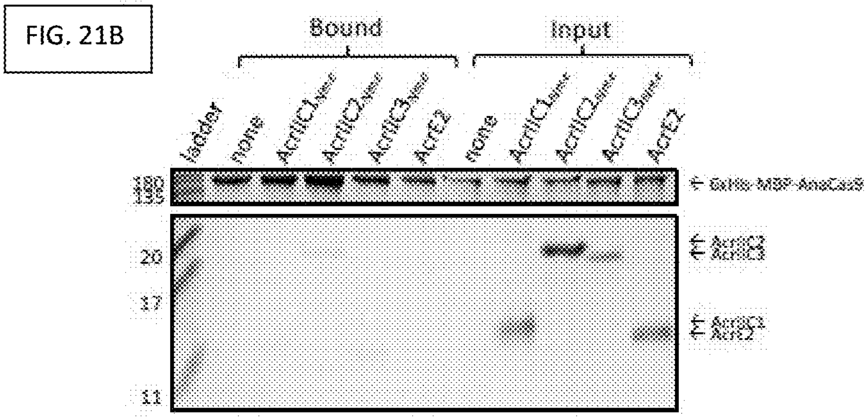
Figure 22:
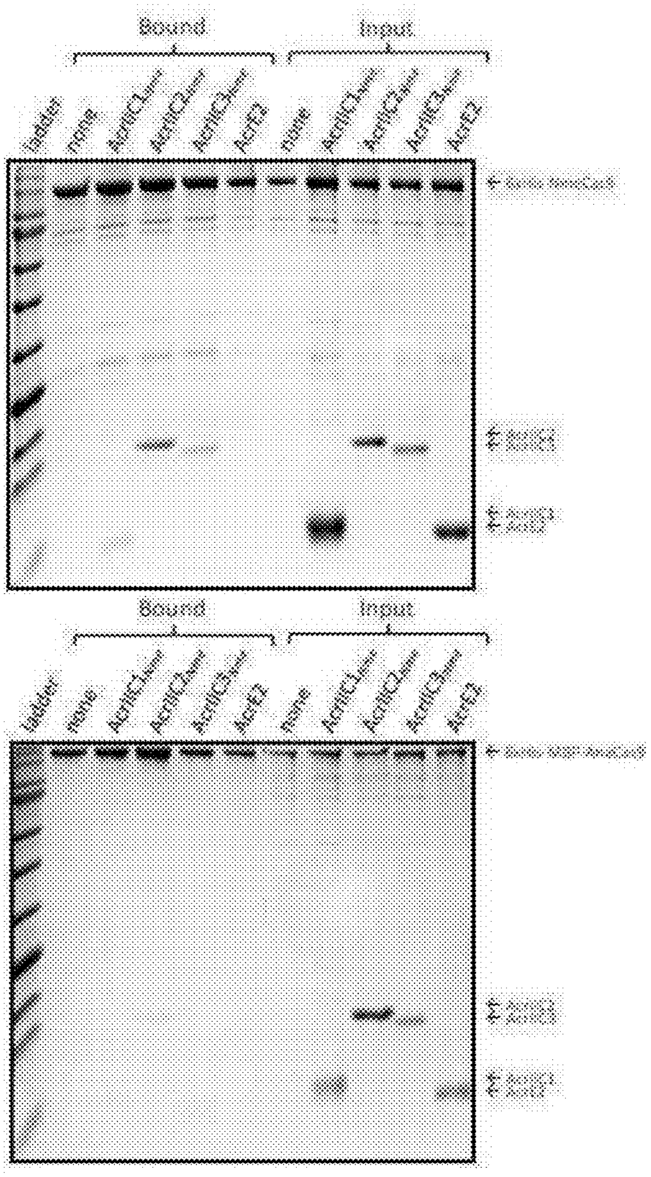
FIG. 22 redisplays the exemplary data of FIG. 21A-B as uncropped images of the Coomassie-stained SDS-PAGE analysis.

A direct interaction of type II-C anti-CRISPR proteins with NmeCas9 was determined by mixing purified, untagged anti-CRISPR proteins with purified, 6×His-tagged NmeCas9 protein (preloaded with coexpressed sgRNA) and conducting nickel affinity chromatography to assess whether the anti-CRISPR proteins directly bound NmeCas9 in vitro. It was found that AcrIIC1Nme, AcrIIC2Nme, and AcrIIC3Nme were all retained on the nickel column, reflecting an association with NmeCas9. By contrast, a previously identified type I anti-CRISPR protein (AcrE2; (Pawluk et al., 2014)) did not associate with NmeCas9, and the anti-CRISPR proteins did not bind significantly to AnaCas9. FIGS. 21B and 22. AnaCas9 is a distantly related type II-C Cas9 homolog with ~20% sequence identity to NmeCas9. Jinek et al., 2014; Ma et al., 2015a. These data demonstrate that the anti-CRISPR proteins disclosed herein specifically bind to NmeCas9.

Figure 23:
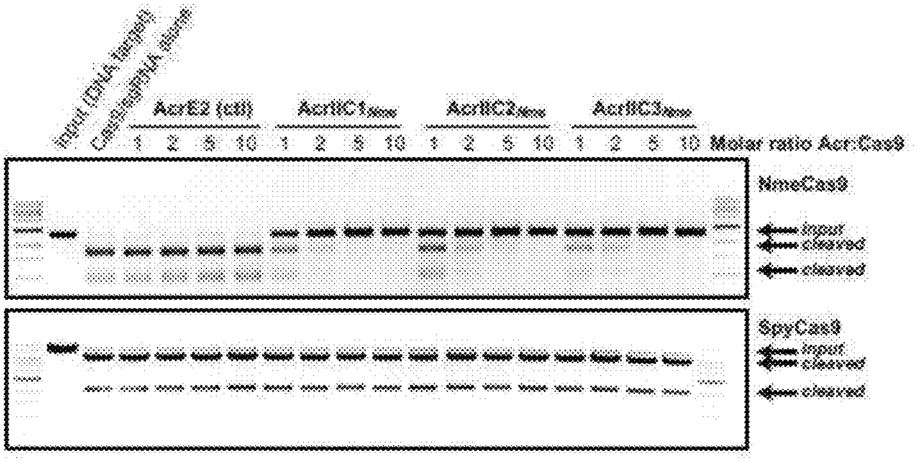
FIG. 23 presents exemplary data showing that type II-C Anti-CRISPR proteins specifically block in vitro DNA cleavage by NmeCas9. Linear plasmid DNA bearing a protospacer adjacent to a PAM sequence was subjected to in vitro digestion by purified, recombinant, sgRNA-programmed NmeCas9 (upper panel) or SpyCas9 (lower panel). Where indicated at the top of each lane, Cas9 was preincubated with purified anti-CRISPR proteins as indicated with AcrE2 as a negative control. Molar equivalents of anti-CRISPR protein (relative to Cas9) are shown at the top of each lane, and mobilities of input and cleaved DNAs are denoted on the right.

To assess the effect of the anti-CRISPR proteins on Cas9 enzymatic activity, in vitro DNA cleavage assays were performed. (Zhang et al., 2015) When purified NmeCas9 was loaded with in vitro transcribed sgRNA and then mixed with target DNA, robust and specific cleavage was observed. FIG. 23. Cleavage was unaffected by prior incubation of NmeCas9 with increasing amounts of the control, type I-specific anti-CRISPR, AcrE2. In contrast, addition of the *N. meningitidis* anti-CRISPR proteins to these reactions resulted in inhibition of NmeCas9-catalyzed cleavage in a dose-dependent manner. Approximately 50% cleavage inhibition resulted when the anti-CRISPR proteins were added at a 1:1 molar ratio, and complete inhibition was seen at a 5:1 anti-CRISPR:NmeCas9 ratio. FIG. 23. The DNA cleavage activity of *S. pyogenes* Cas9 (SpyCas9), which is the most commonly used Cas9 for genome editing, was not affected by addition of any of the anti-CRISPR proteins (FIG. 23, lower panel). This result was expected because SpyCas9 belongs to the type II-A CRISPR-Cas type and is very distantly related to NmeCas9. Overall, these in vitro data clearly demonstrate that these anti-CRISPR proteins directly bind to and specifically inhibit the DNA cleavage activity of NmeCas9. The inhibitory effects of anti-CRISPR proteins on NmeCas9 in its sgRNA-loaded form imply that the natural protective functions of the anti-CRISPR proteins require inhibition of crRNA/tracrRNA-loaded NmeCas9 that is already present in the host cell at the time of phage infection.

C. Anti-CRISPR Proteins Inhibit NmeCas9 Genome Editing

In one embodiment, the present invention contemplates a plurality of direct anti-CRISPR protein inhibitors of NmeCas9 activity that are off-switches for CRISPR-Cas9 genome editing in mammalian cells. For example, HEK293T cells were co-transfected with three plasmids: one expressing NmeCas9, one expressing a genome-targeting sgRNA, and one expressing an anti-CRISPR. Genome editing efficiency was determined using an established T7 endonuclease 1 (T7E1)-based protocol. Strikingly, it was found that each of the anti-CRISPR proteins greatly decreased the ability of NmeCas9 to create genome lesions in cultured human cells. FIG. 24A-B, FIG. 25A-B, FIG. 26A-E and Table 3.

TABLE 3

Templates For Transcription Of sgRNAs That Target Several Human Genome Sites

| PLASMID NAME/CONSTRUCT | TARGET SITE | T7E1 F-OLIGO | T7E1 R-OLIGO | SPACER CLONING F-OLIGO | SPACER CLONING R-OLIGO |
|---|---|---|---|---|---|
| pEJS161: pSimpleII-NmeCas9-sgRNA/NTS1C | N-TS1C | GCACTTATTCTGGCCCCTGACTGC | GAGAACCATGGTCTGGGGAAGAAGACC | CACCGTGGTCTGGGGTACAGCCTTGGCA | CAACTGCCAAGGCTGTACCCCAGACCAC |
| pEJS173: pSimpleII-NmeCas9-sgRNA/NTS4B | N-TS4B | AGAGGAGCCTTCTGACTGCTGCAGA | AGGTCCTGGCCTTGCCTTCGA | CACCGGACAGGAGTCGCCAGAGGCCGGT | CAACACCGGCCTCTGGCGACTCCTGTCC |
| pEJS174: pSimpleII-NmeCas9-sgRNA/NTS4C | N-TS4C | AGAGGAGCCTTCTGACTGCTGCAGA | AGGTCCTGGCCTTGCCTTCGA | CACCGGGGCTGGCTCCACGTCGCGCCGC | CAACGCGGCGCGACGTGGAGCCAGCCCC |
| pEJS212: pSimpleII-NmeCas9-sgRNA/NTS7 | N-TS7 | GGACAGAAGAGAGTAGGGAGACGAG | GCATTCTGTCATCTGCATATCCCTCTG | CACCGAGGGAGAGAGGTGAGCGGATGAA | CAACTTCATCCGCTCACCTCTCTCCCTC |
| pEJS224: pSimpleII-NmeCas9-sgRNA/NTS8 | N-TS8 | TGCCTCACGTAACAGTTGAGACCC | TGCCCTCCCCGCTGGAACCT | CACCGGACGCAATTCCAGAGGTGATGGG | CAACCCCATCACCTCTGGAATTGCGTCC |
| pEJS236: pSimpleII-NmeCas9-sgRNA/NTS11 | N-TS11 | ACAGGCAACTCCATCCATGAGCC | CTTCACAGCACTTAGGACTGTCTG | CACCGTTCCAGTTGGGAAGGGCCAGTGC | CAACGCACTGGCCCTTCCCAACTGGAAC |
| pEJS323: pSimpleII-NmeCas9-sgRNA/NTS25 | N-TS25 | GCAATCCACCCAATGCTAACTGG | TGAACACAAAGGCCTCCAGATCC | CACCGGTTTCTCATCCTGTCTTCTGCCT | CAACAGGCAGAAGACAGGATGAGAAACC |
| pEJS337: pLK.01-NmeSgRNA/DTS3 | D-TS3 (Nme) | GGACAAAAGCAGCCCATTAG | GGACTCCTAAAATGGCCACA | CACCGACTGAAGGCGAGGTCCGGGGCGG | CAACCCGCCCCGGACCTCGCCTTCAGTC |
| pEJS399: pLK.01-SpySgRNA/DTS3 | D-TS3 (Spy) | GGACAAAAGCAGCCCATTAG | GGACTCCTAAAATGGCCACA | ACCGGAAGGCGAGGTCCGGGGCGG | AAACCCGCCCCGGACCTCGCCTTC |

TABLE 3-continued

Templates For Transcription Of sgRNAs That Target Several Human Genome Sites

| | | | | | |
|---|---|---|---|---|---|
| pEJS341: pLK.O1-NmeSgRNA/DTS7 | D-TS7 (Nme) | AGGACTGCTCTCAGCTACCG | AAGGGCAGAGAGGCTAAAGG | CACCGGCTGGCACCCTCCATGTACCCAG | CAACCTGGGTACATGGAGGGTGCCAGCC |
| pEJS400: pLK.O1-SpySgRNA/DTS7 | D-TS7 (Spy) | AGGACTGCTCTCAGCTACCG | AAGGGCAGAGAGGCTAAAGG | ACCGGGCACCCTCCATGTACCCAG | AAACCTGGGTACATGGAGGGTGCC |
| pEJS468: pLK.O1-NmeSgRNA/DTS13-Telomere | D-TS13 (Nme-telomere) | N/A | N/A | ACCGTTAGGGTTAGGGTTAGGGTTAGGG | CAACCCCTAACCCTAACCCTAACCCTAA |
| pEJS469: pLK.O1-SpySgRNA/DTS13-Telomere | D-TS13 (Spy-telomere) | N/A | N/A | ACCGTTAGGGTTAGGGTTAGGGTT | AAACAACCCTAACCCTAACCCTAA |

| PLASMID NAME/CONSTRUCT | SPACER SEQUENCE | LOCUS NAME | CHROMOSOME NUMBER | SEQ ID NO: |
|---|---|---|---|---|
| pEJS161: pSimpleII-NmeCas9-sgRNA/NTS1C | GTGGTCTGGGGTACAGCCTTGGCA | SLC9A9 | 3 | 36, 37, 38, 39, 40 |
| pEJS173: pSimpleII-NmeCas9-sgRNA/NTS4B | GGACAGGAGTCGCCAGAGGCCGGT | FLJ00328 | 14 | 41, 42, 43, 44, 45 |
| pEJS174: pSimpleII-NmeCas9-sgRNA/NTS4C | GGGGCTGGCTCCACGTCGCGCCGC | FLJ00328 | 14 | 46, 47, 48, 49, 50 |
| pEJS212: pSimpleII-NmeCas9-sgRNA/NTS7 | GAGGGAGAGAGGTGAGCGGATGAA | LOC100505797 | 18 | 51, 52, 53, 54, 55 |
| pEJS224: pSimpleII-NmeCas9-sgRNA/NTS8 | GGACGCAATTCCAGAGGTGATGGG | ESPN | 1 | 56, 57, 58, 59, 60 |
| pEJS236: pSimpleII-NmeCas9-sgRNA/NTS11 | GTTCCAGTTGGGAAGGGCCAGTGC | SMARCB1 | 22 | 61, 62, 63, 64, 65 |
| pEJS323: pSimpleII-NmeCas9-sgRNA/NTS25 | GGTTTCTCATCCTGTCTTCTGCCT | AC193513 | 7 | 66, 67, 68, 69, 70 |
| pEJS337: pLK.O1-NmeSgRNA/DTS3 | GACTGAAGGCGAGGTCCGGGGCGG | ARHGEF9 | X | 71, 72, 73, 74, 75 |
| pEJS399: pLK.O1-SpySgRNA/DTS3 | GAAGGCGAGGTCCGGGGCGG | ARHGEF9 | X | 76, 77, 78, 79, 80 |
| pEJS341: pLK.O1-NmeSgRNA/DTS7 | GGCTGGCACCCTCCATGTACCCAG | LSP1 | 11 | 81, 82, 83, 84, 85 |
| pEJS400: pLK.O1-SpySgRNA/DTS7 | GGCACCCTCCATGTACCCAG | LSP1 | 11 | 86, 87, 88, 89, 90 |
| pEJS468: pLK.O1-NmeSgRNA/DTS13-Telomere | TTAGGGTTAGGGTTAGGGTTAGGG | N/A | N/A | 91, 92, 93 |
| pEJS469: pLK.O1-SpySgRNA/DTS13-Telomere | TTAGGGTTAGGGTTAGGGTT | N/A | N/A | 94, 95, 96 |

In one embodiment, the present invention contemplates anti-CRISPR proteins that are less than approximately 14 kDa. Although it is not necessary to understand the mechanism of an invention it is believed that these anti-CRISPR proteins are small enough to diffuse freely through nuclear pores such that they can inhibit NmeCas9 genome editing even without an appended, heterologous nuclear localization sequence (NLS).

These plasmid titration experiments demonstrated that at least three anti-CRISPR families could completely inhibit type II Cas9 gene editing (e.g., 100% inhibition), with AcrIIC3Nme appearing to be the most potent. However, gene editing was inhibited at least 70%, preferably 75% and most preferably 90% or greater. FIG. 26A-E. The superior potency of AcrIIC3Nme anti-CRISPR activity in mammalian cells is noteworthy given that it was slightly less effective at inhibiting transformation interference in meningococcal cells. FIG. 19C. The variations in activities of these anti-CRISPR proteins in mammalian cells are likely due to differences in expression or stability as they all displayed similar inhibitory activities in vitro. FIG. 23. Consistent with other in vitro results, the anti-CRISPR proteins had no effect on editing mediated by SpyCas9 targeting the same genomic site. FIGS. 24A-B and 25A-B. In addition, type I-E anti- CRISPR AcrE2 had no significant inhibitory effect in any of these experiments. In no instance was any sign of cellular toxicity observed by any anti-CRISPR protein. In one embodiment, the present invention contemplates a plurality of anti-CRISPR proteins that precisely control Cas9-mediated genome editing by means of inhibition.

D. AcrIIC3Nme Prevents dNmeCas9 Genome Binding

"Dead" Cas9 (dCas9) orthologs, including dNmeCas9 have been reported to be useful for RNA-guided DNA binding without Cas9-catalyzed DNA cleavage. Esvelt et al., 2013; Hilton et al., 2015; 228 Kearns et al., 2015; Ma et al., 2015b. Although it is not necessary to understand the mechanism of an invention, it is believed that dCas9 proteins have a wide range of domains and functionalities that can be fused or tethered to the DNA-bound dCas9/sgRNA complex. Dominguez et al., 2016; Wang et al., 2016.

Figure 24A:
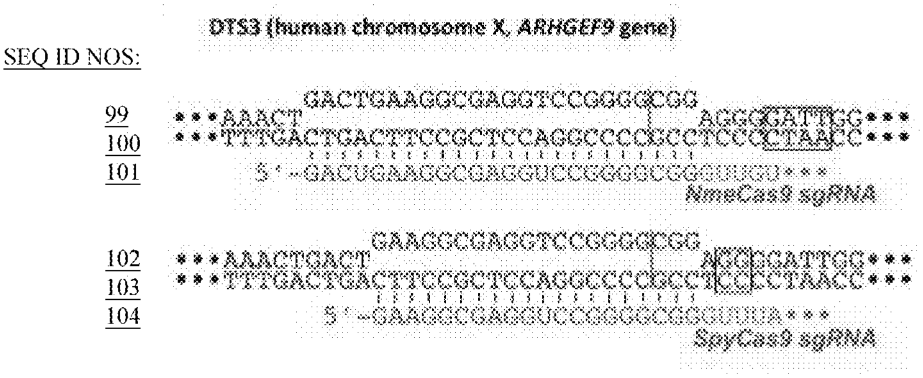
FIG. 24A-B presents exemplary data showing that type II-C anti-CRISPR proteins specifically block genome editing by NmeCas9 in human cells.
Figure 24B:
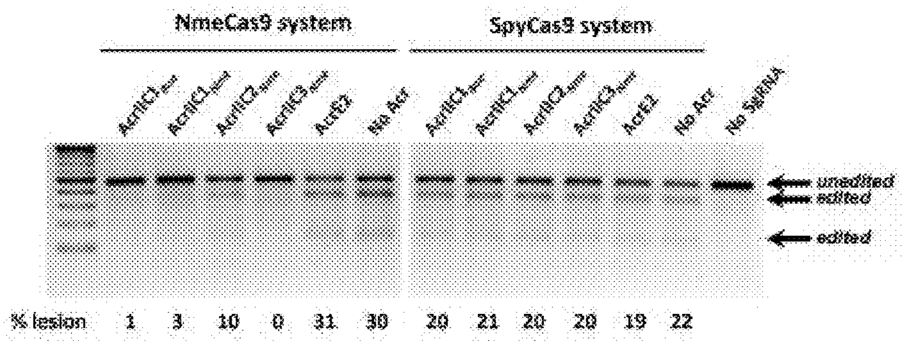
Figure 25A:
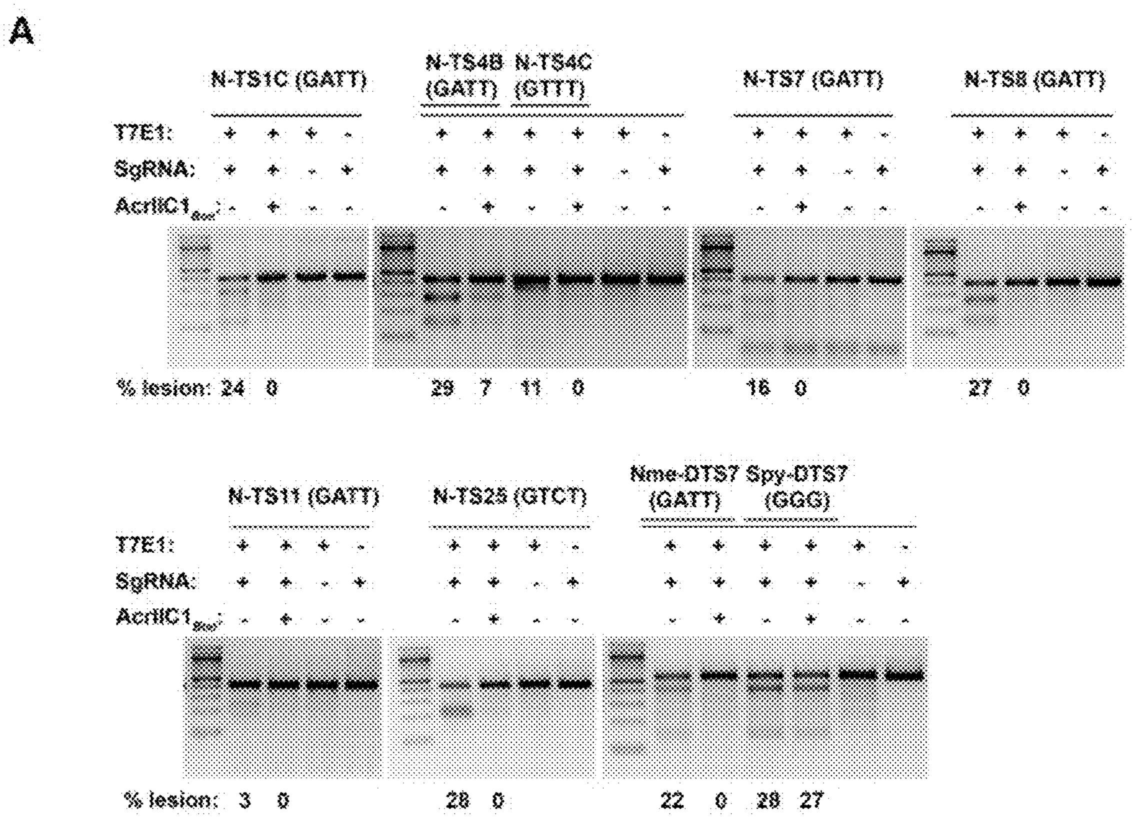
Figure 26A:
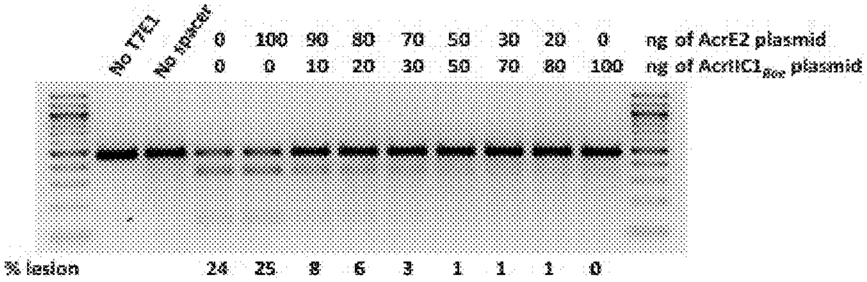
FIG. 26A-E presents exemplary data showing plasmid titration of anti-CRISPR proteins in human genome editing. Related to FIG. 24A-B.
Figure 26B:
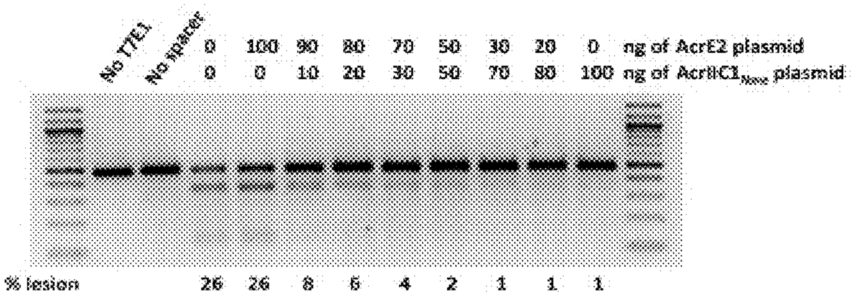
Figure 26C:
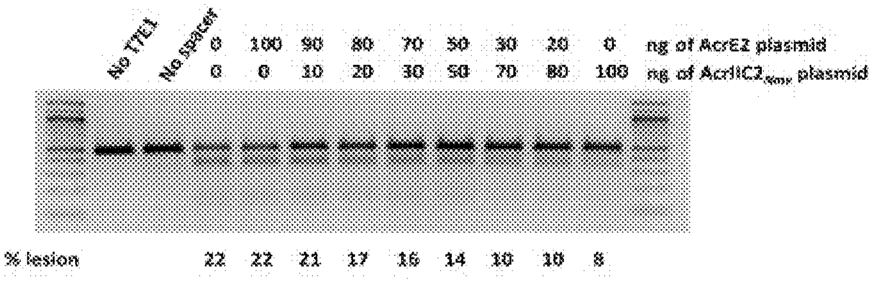
Figure 26D:
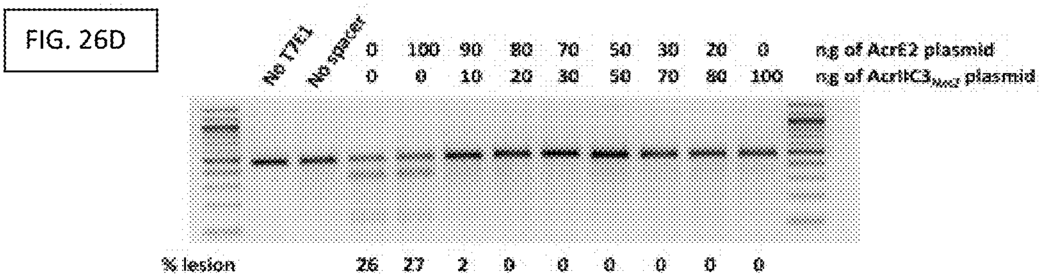
Figure 26E:
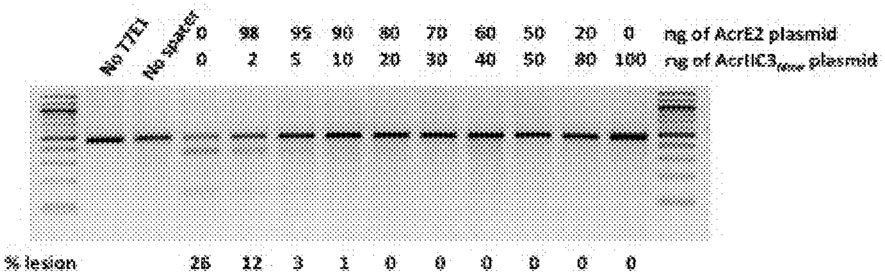

As shown above, anti-CRISPR inhibition of sgRNA-guided NmeCas9 DNA cleavage and genome editing could reflect either inhibition upstream of stable R-loop formation, or inhibition of NmeCas9 catalytic activation after stable R-loop formation. FIGS. 23 and 24A-B. In the former case, the anti-CRISPR could be used as an off-switch not only for genome editing, but also for dNmeCas9 DNA binding applications such as CRISPRi and CRISPRa. Dominguez et al., 2016; Wang et al., 2016.

Figure 27A:
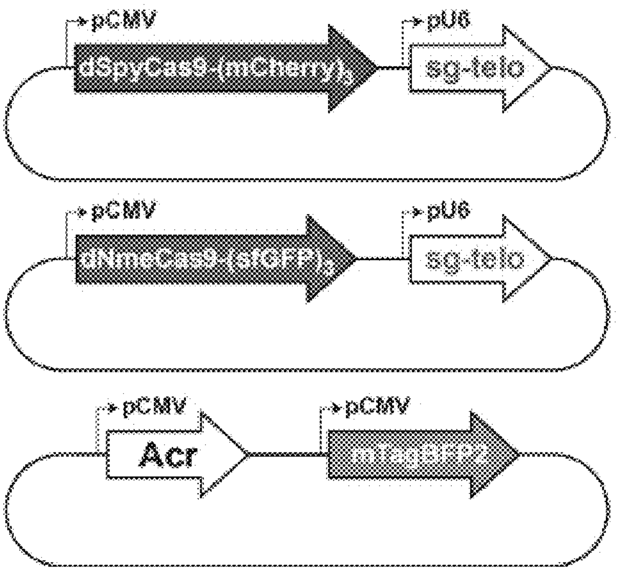
FIG. 27A-F presents exemplary data showing that AcrIIC2Nme and AcrIIC3Nme prevents DNA binding by NmeCas9 in human cells.
Figures 27B, 27C, 27D, 27E, 27F:
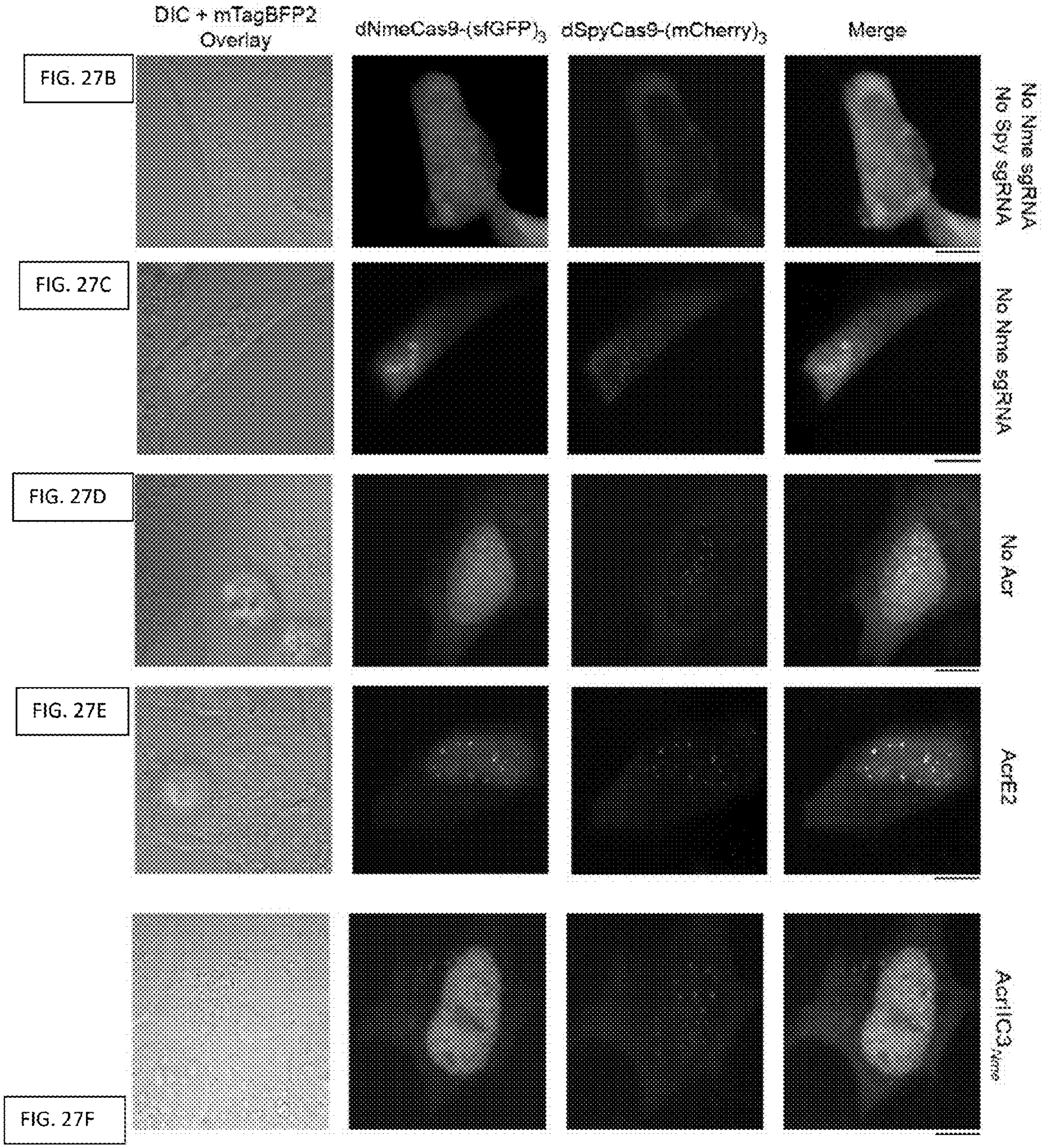

To determine whether a genome editing inhibitor (e.g., AcrIIC3Nme) can prevent stable DNA binding by dNmeCas9 in mammalian cells, a previously developed system was used in which superfolder (sf) GFP-labeled dNmeCas9 and mCherry-labeled dSpyCas9 are simultaneously colocalized to telomeric loci by cognate sgRNAs upon co-transfection of their expression plasmids in U2OS cells. FIG. 27A; Ma et al., 2015b. Colocalization of telomeric dNmeCas9-$(sfGFP)_3$ and dSpyCas9-$(mCherry)_3$ foci was observed as long as both of the telomere-directed sgRNAs were included as the two dCas9 orthologs. FIGS. 27B-D. A co-transfected, mTagBFP2-marked plasmid also carrying an anti-CRISPR expression cassette was also tested. FIG. 27A, bottom. AcrE2 had no effect on telomeric colocalization of dNmeCas9-$(sfGFP)_3$ and dSpyCas9-$(mCherry)_3$. FIG. 27E. In contrast, co-expression of AcrIIC3Nme prevented the co-localization of dNmeCas9-$(sfGFP)_3$ with the dSpyCas9-$(mCherry)_3$ telomeric foci. FIG. 27F.

Telomeric dNmeCas9-$(sfGFP)_3$ foci were observed in 94% (31 out of 33) of cells in the absence of any Acr protein, and 88% (31 out of 37) of cells in the presence of the negative control AcrE2 protein. By contrast, 0% of cells (0 out of 46) exhibited dNmeCas9-(sfGFP)3 telomeric foci when AcrIIC3Nme was coexpressed. These results confirm the robust inhibitory effect of AcrIIC3Nme on stable, sgRNA-programmed DNA binding by dNmeCas9, and indicate that they can be used as a potent off-switch not only for NmeCas9 genome editing, but also for dNmeCas9-based applications in mammalian cells.

E. Global Inhibition of Type II-C CRISPR-Cas9 by Anti-CRISPR Proteins

Figure 28A:
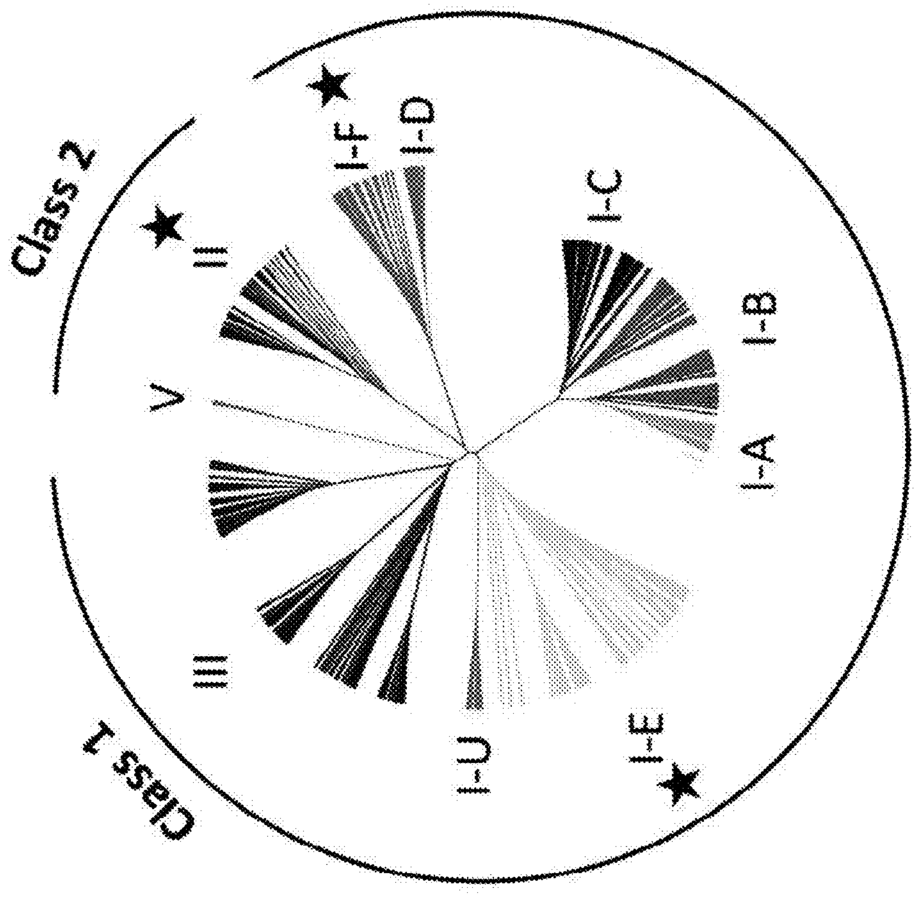
FIG. 28A-B presents an exemplary analysis showing that anti-CRISPR proteins may interact with most, if not all, CRISPR-Cas systems.
Figure 28B:
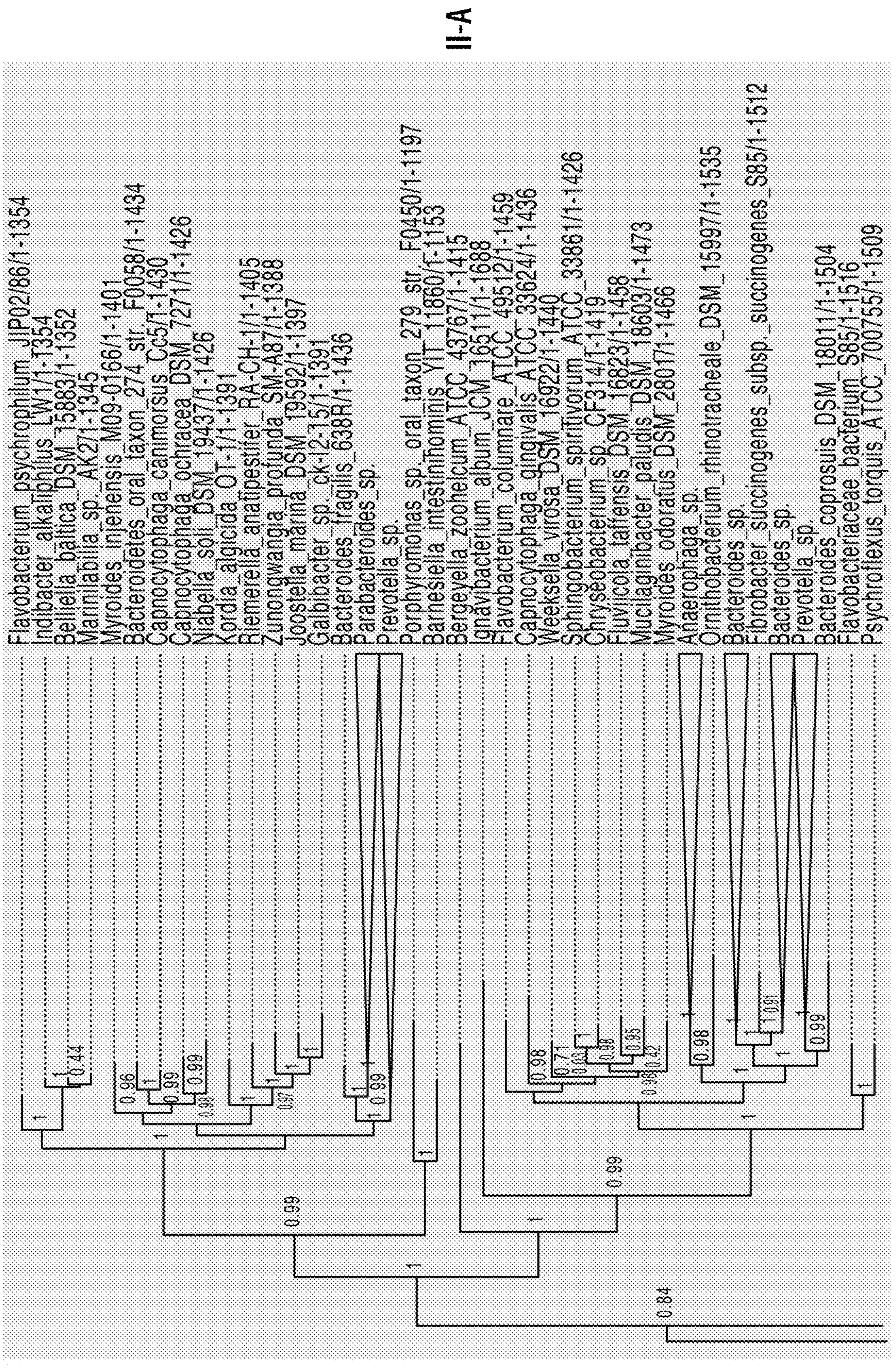
Figure 28B:
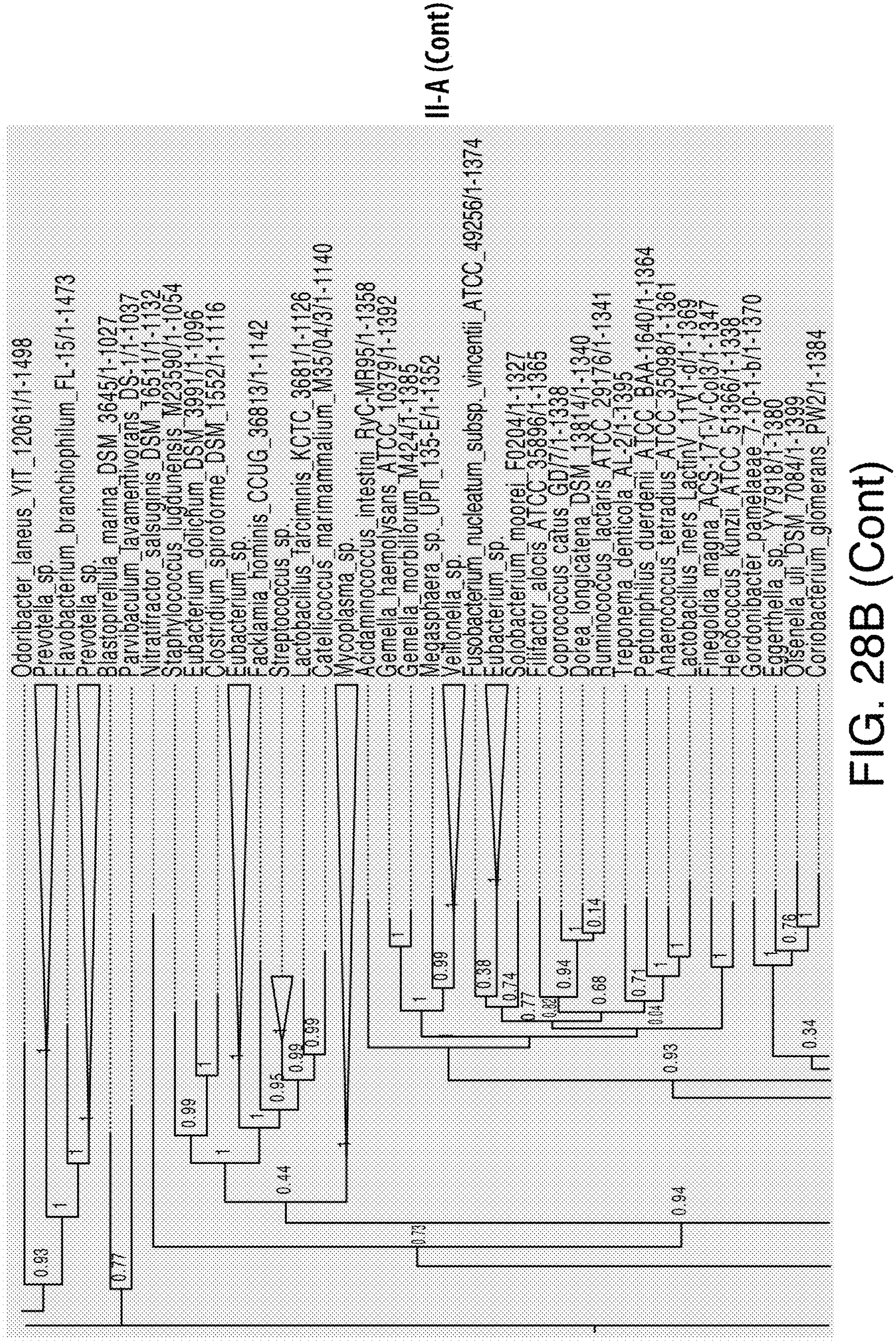
Figure 28B:
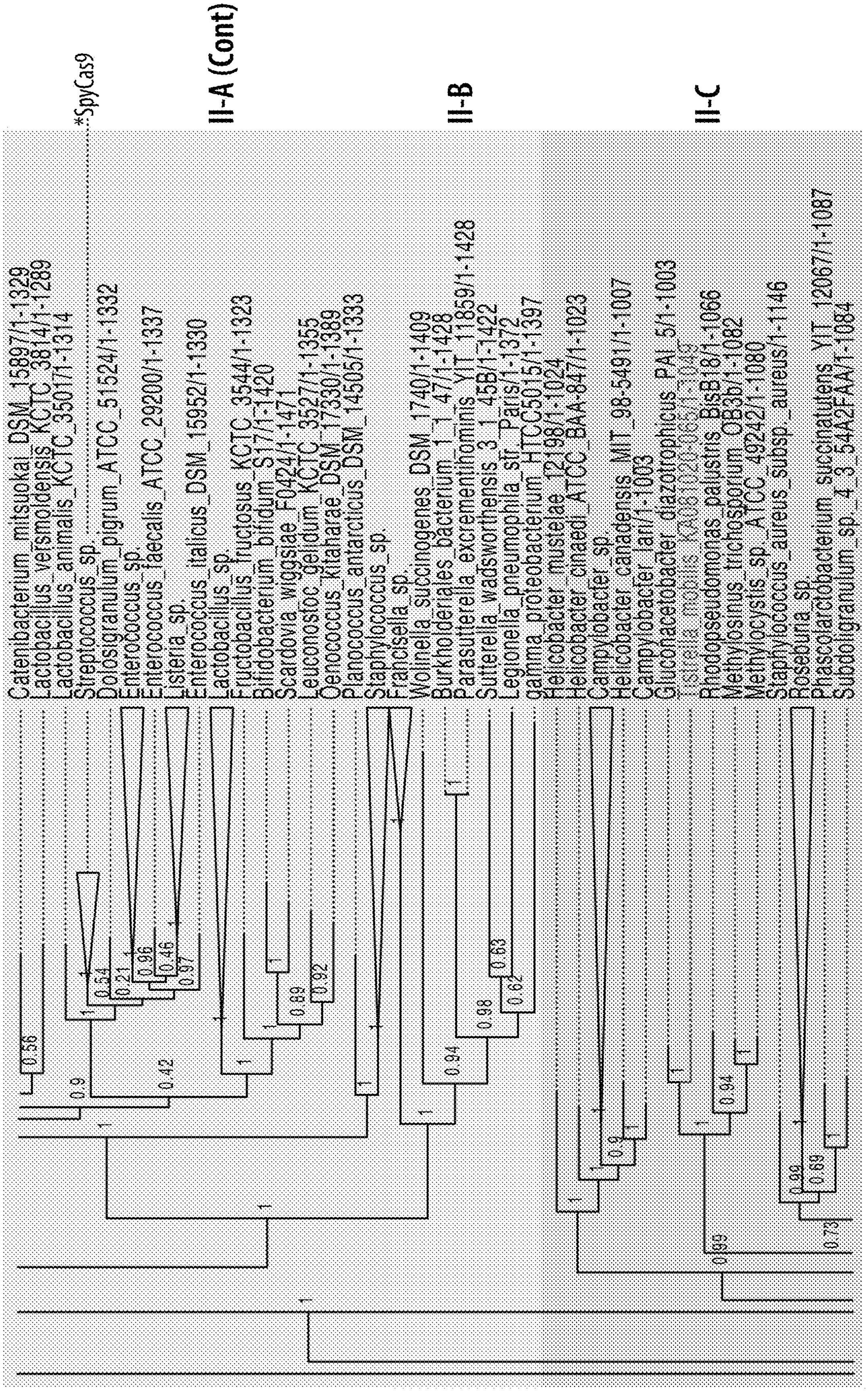
Figure 28B:
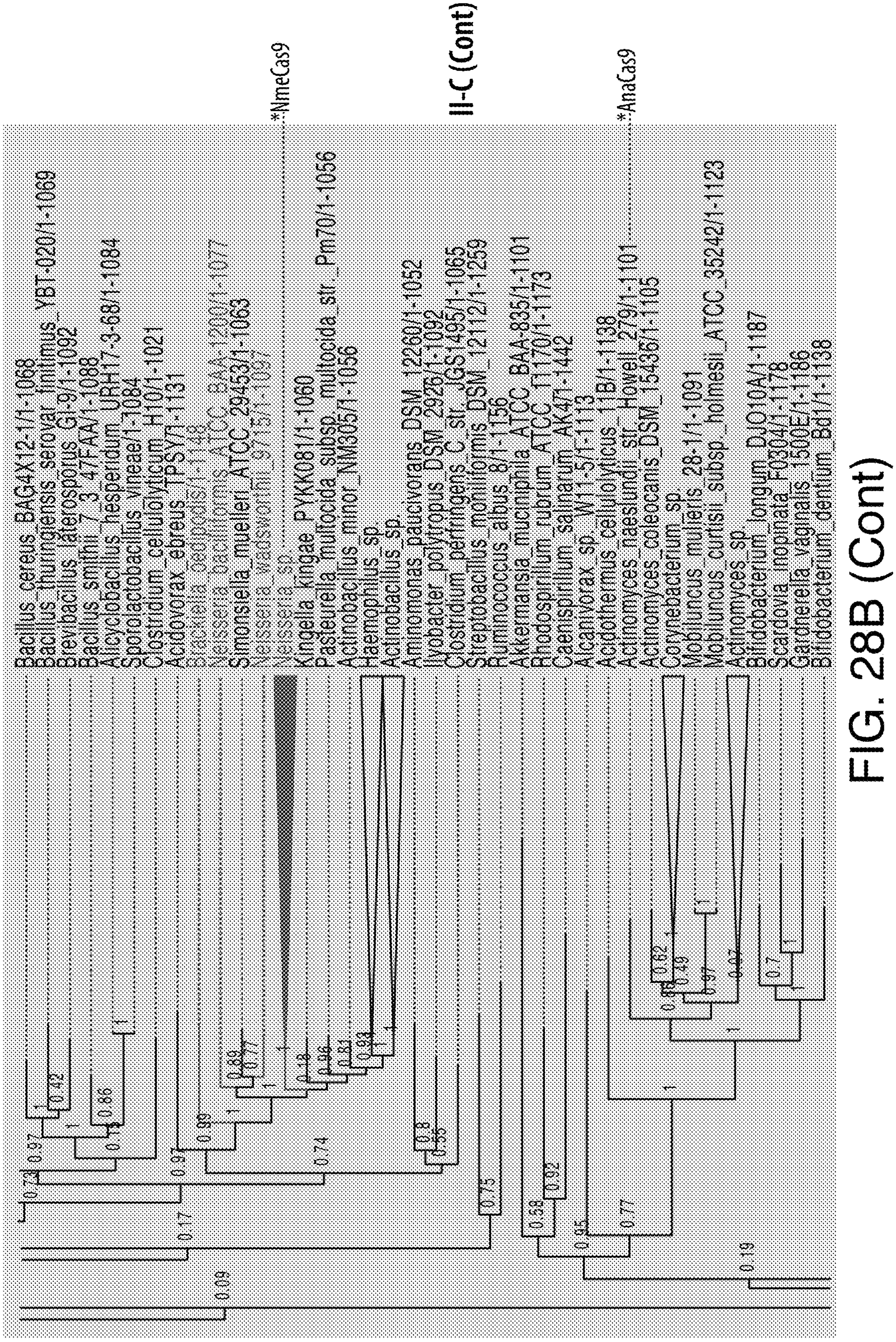
Figure 28B:
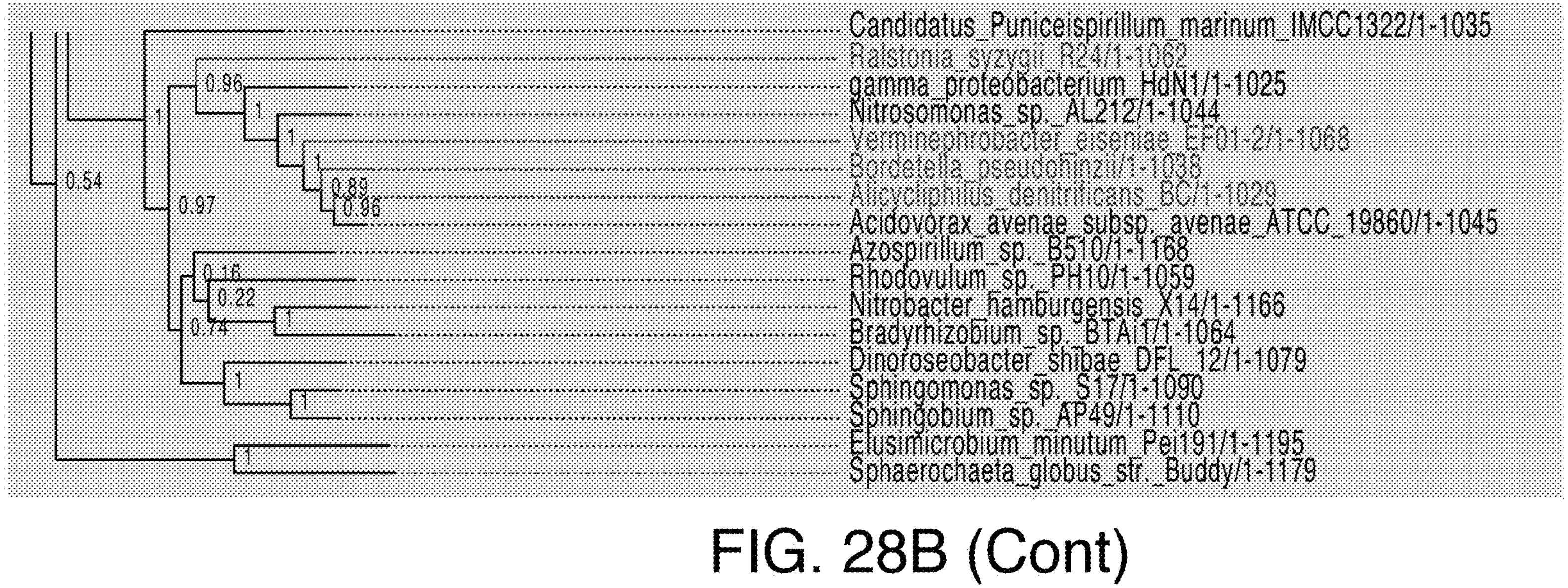
Figure 29:
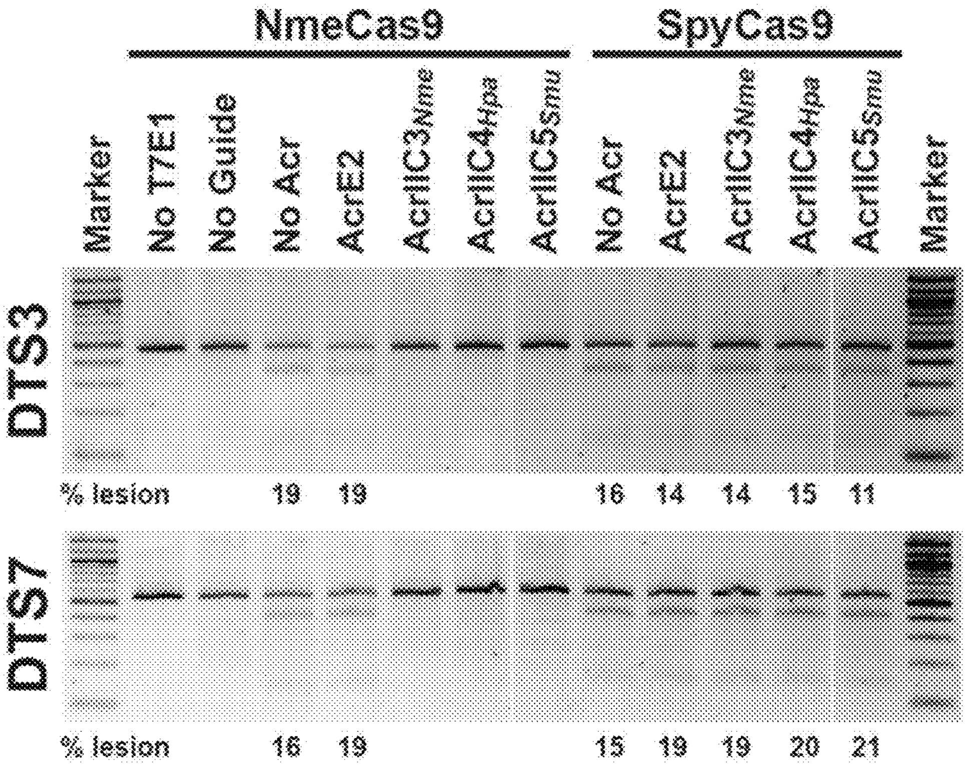
FIG. 29 presents exemplary data showing selective inhibition of NmeCas9 (Type II-C) gene editing vs. SpyCas9 (Type II-A) gene editing at the D-TS3 (top panel) and D-TS7 (bottom panel) dual target sites with three Acr proteins (AcrIIC3Nme (positive control), AcrIIC4Hpa and AcrIIC5Smu). Nme/Spy Cas9+SgRNA plasmids (150 ng each)+Acr plasmid (100 ng).
Figure 30:
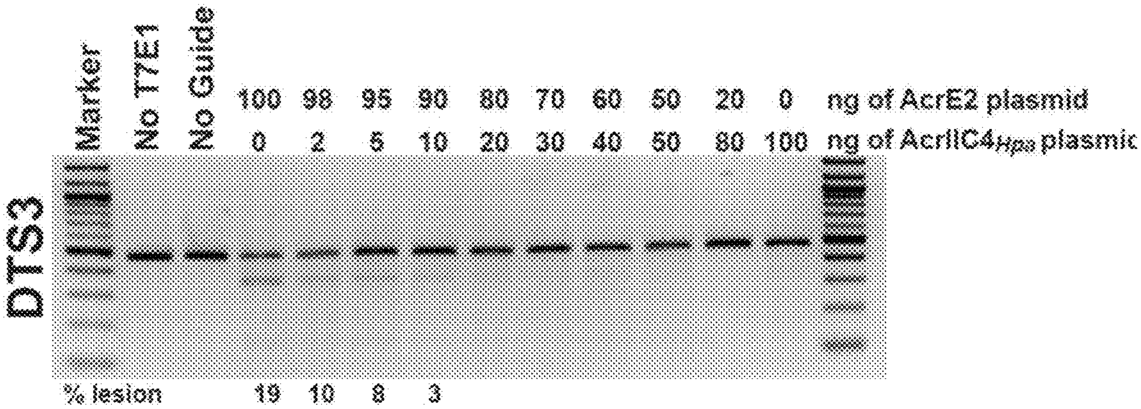
FIG. 30 presents exemplary data showing a dose-response relationship of AcrIIC4Hpa (top panel) and AcrIIC5Smu (bottom panel) inhibition of NmeCas9 (Type II-C) editing at the D-TS3 dual target site. NmeCas9+SgRNA plasmids (150 ng each)+Acr plasmid (100 ng).
Figure 30:
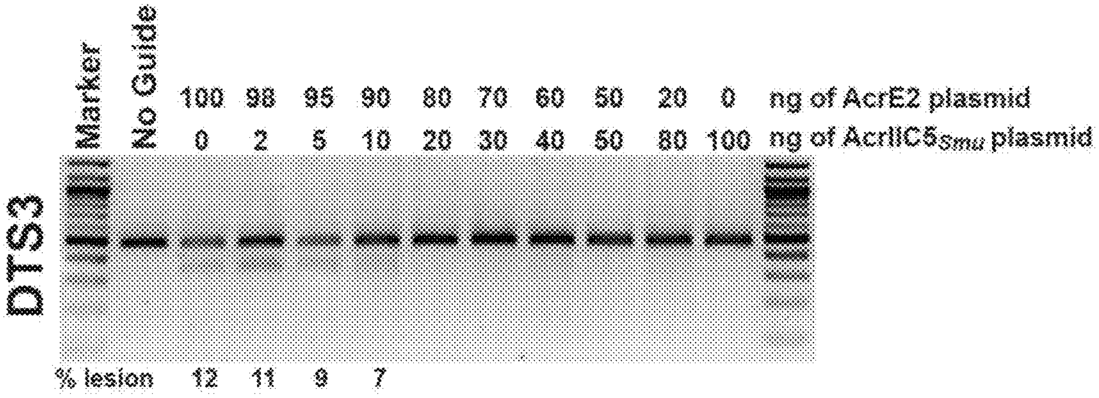
Figures 31A, 31B, 31C, 31D, 31E:
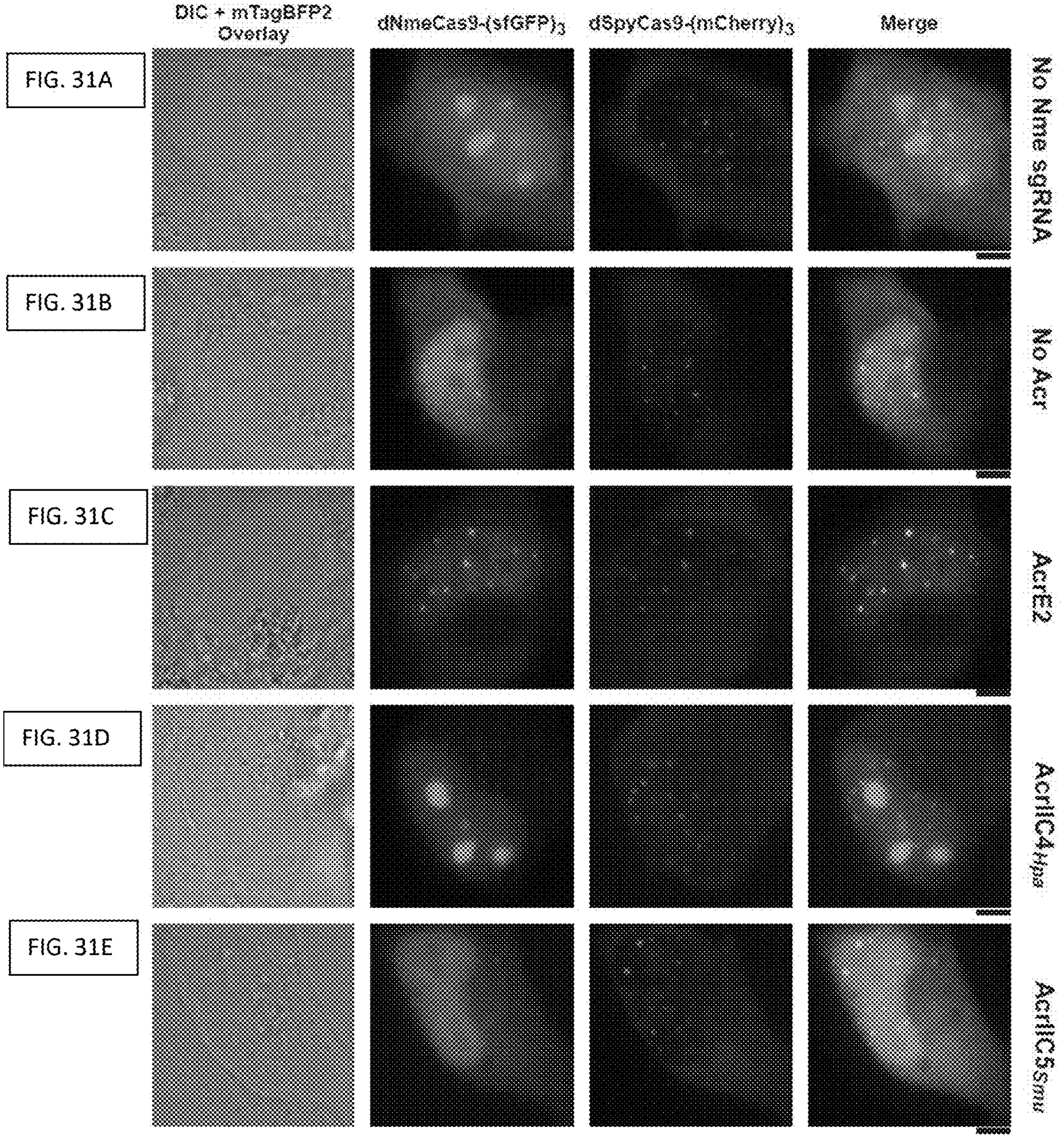
FIG. 31A-F (panels A-E) presents fluorescence images of U2OS cells transiently transfected with plasmids depicted in FIG. 27A. The specific version of each plasmid set (with or without sgRNAs, with or without anti-CRISPRs) is given to the right of each row. First column: differential interference contrast (DIC) and mTagBFP2 imaging, merged. Second column: dNmeCas9-(sfGFP)3. Third column: dSpyCas9-(mCherry)3. Fourth column: dNmeCas9-(sfGFP)3 and dSpyCas9-(mCherry)3, merged. Scale bars, 5 μm. Panel F: Quantitation of dNmeCas9-(sfGFP)3 telomeric foci, as judged by co-localization with dSpyCas9-(mCherry)3 telomeric foci, in cells that express no anti-CRISPR, negative control anti-CRISPR (AcrE2), AcrIIC3Nme, AcrIIC4Hpa, or AcrIIC5Smu. Foci were scored blind.
Figure 31F:
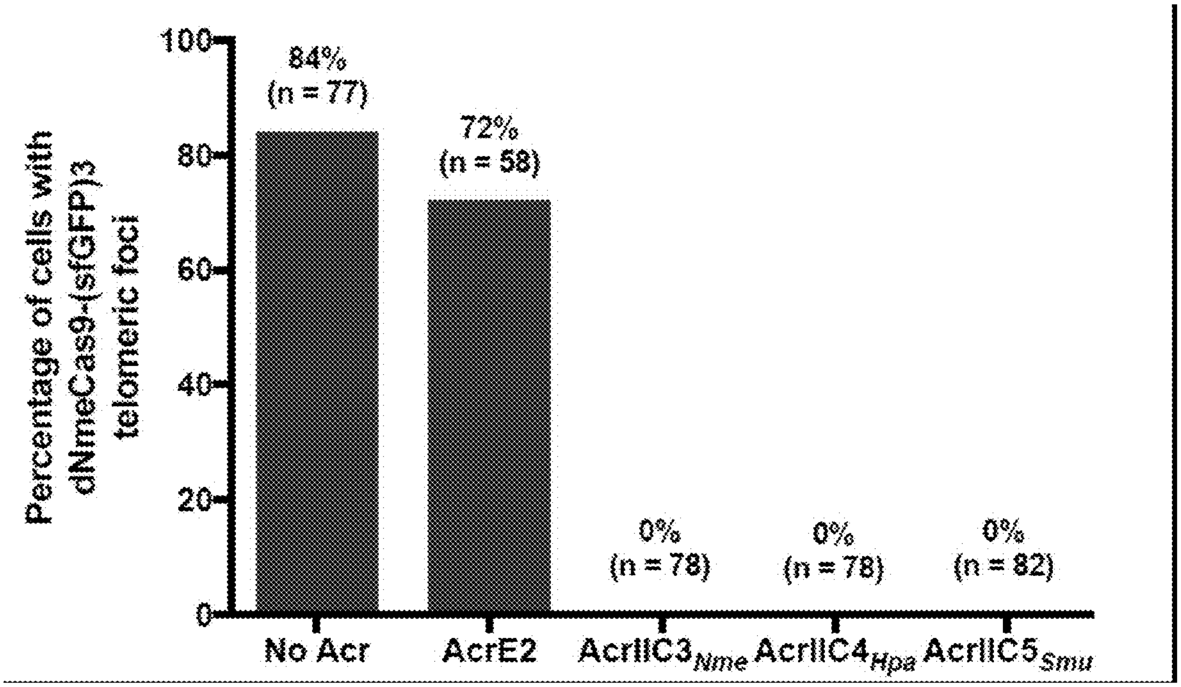
Figure 32:
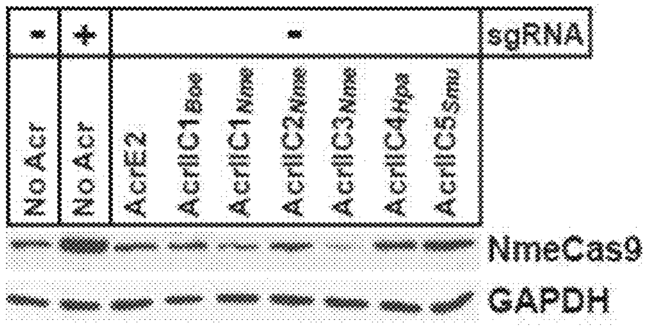
FIG. 32 presents exemplary data showing that some Acr proteins affect the ability of NmeCas9 to accumulate when co-expressed in human cells, either without (upper panel) or with (lower panel) co-expressed sgRNA. HEK293 cells were transfected with NmeCas9+SgRNA plasmids (100 ng each)+Acr plasmid (200 ng). In each panel, HA-tagged NmeCas9 was detected by probing a western blot of total protein (20 micrograms per lane) from transfected cells, using anti-HA antibodies. Detection of GAPDH protein with an anti-GAPDH antibody was used as a loading control, as indicated.
Figure 32:
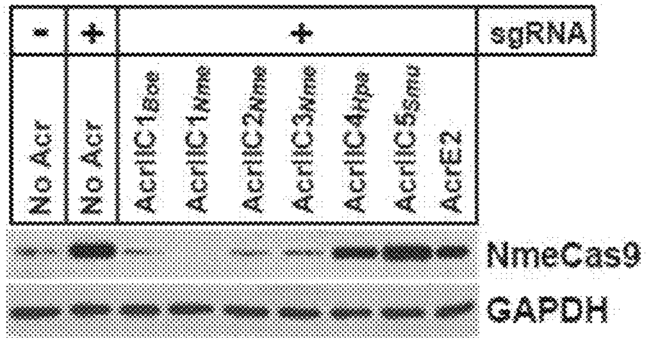
Figure 33:
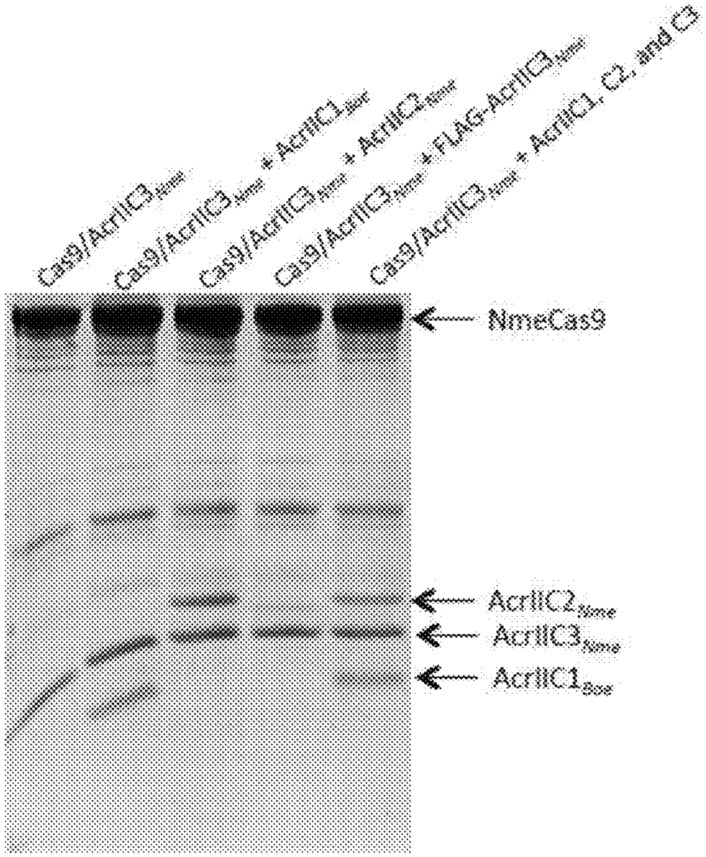
FIG. 33 shows that AcrIIC1, AcrIIC2, and AcrIIC3 bind to NmeCas9 at distinct interaction surfaces. Untagged AcrIIC3$_{Nme}$ was co-expressed with 6His-tagged NmeCas9 in *E. coli*. The complex of the two proteins was purified using Ni-affinity chromatography. Following purification, this NmeCas9/AcrIIC3$_{Nme}$ complex was incubated with purified, untagged AcrII1$_{Boe}$, AcrIIC2$_{Nme}$, or both proteins. NmeCas9 and bound proteins were then purified using a second Ni-affinity column and the resulting complexes were analyzed by SDS-PAGE followed by Coomassie staining. All three anti-CRISPR proteins are able to bind NmeCas9 simultaneously, and the binding of one did not abrogate the binding of any other. This indicates that they could be used simultaneously to inhibit the activity of Cas9 and decrease the chances of anti-CRISPR resistant mutants arising.
Figure 34:
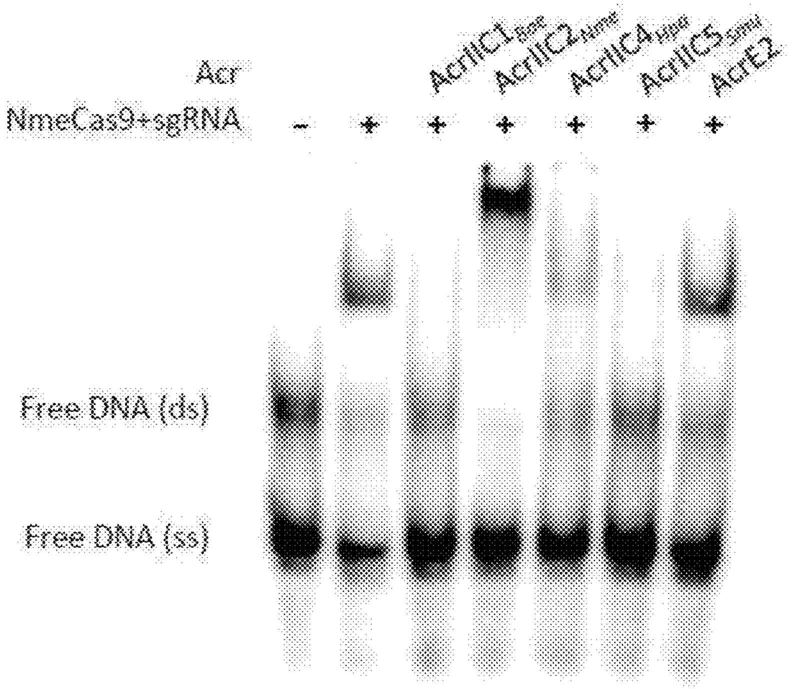
FIG. 34 presents DNA binding by NmeCas9 in the absence and presence of anti-CRISPR proteins, assayed using an electrophoretic mobility shift assay. Purified NmeCas9+sgRNA is present in all lanes but the first one. The relevant anti-CRISPR protein added to the reaction is noted above each lane. NmeCas9+sgRNA and the anti-CRISPR proteins were premixed and incubated on ice for 5 minutes, $^{32}$P-labelled DNA was added, and the reactions were incubated for 30 minutes at 37° C. AcrIIC1$_{Boe}$ and AcrIIC5$_{Smu}$ completely block Cas9 DNA-binding, while AcrIIC4$_{Hpa}$ partially inhibits binding at the concentration used. AcrIIC2$_{Nme}$ does not interfere with DNA binding, and appears to bind to the NmeCas9/DNA complex. AcrE2, an anti-CRISPR protein for the type I-E CRISPR system, does not inhibit DNA binding by NmeCas9.
Figure 35:
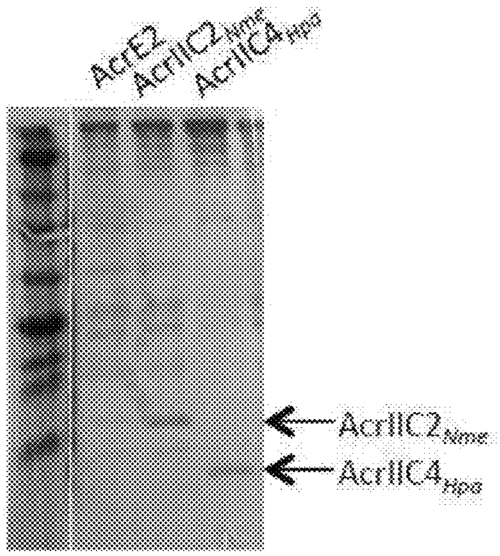
FIG. 35 shows a direct interaction of AcrIIC4Hpa with NmeCas9. Untagged AcrIIC4Hpa was co-expressed with 6His tagged NmeCas9 and the complex was purified and visualized by SDS-PAGE followed by Coomassie staining.

CRISPR-Cas systems may be divided into at least two broad classes, each encompassing several types and many subtypes. For example, Class 1 systems employ multi-subunit surveillance complexes, whereas Class 2 systems have single, large effector proteins like Cas9. Makarova et al., 2015; FIG. 28A-B/6A. Preliminary data on anti-CRISPR proteins acting on type I systems (i.e., for example belonging to Class 1) suggest that each anti-CRISPR protein acts on a particular range of systems within one subtype due to the specificity of protein-protein interactions between the anti-CRISPR and Cas proteins. Bondy-Denomy et al., 2015; Bondy-Denomy et al., 2013; Pawluk et al., 2014; Pawluk et al., 2016. Although it is not necessary to understand the mechanism of an invention, it is believed that an anti-CRISPR gene will likely be selected for if it inhibits the CRISPR-Cas system of the bacterium in which it is found as these genes are almost always located on MGEs that have successfully invaded a host. This belief was used to accurately predict that some anti-CRISPR proteins described here might block type II-C CRISPR-Cas system of *N. meningitidis*. A potential general impact of anti-CRISPR activity on type II CRISPR-Cas systems can be visualized using a phylogenetic tree of Cas9 showing their relationships as direct binding targets of the type II-C anti-CRISPR proteins. FIG. 28B. Bacterial genera in which known type II-C anti-CRISPR homologs are encoded are indicated in red. From this analysis, based on the phylogenetic breadth spanned by the anti-CRISPR orthologs, it can be proposed that greater than half of the type II-C CRISPR-Cas systems may be susceptible to three of the anti-CRISPR families disclosed herein. These data, combined with preliminary studies of type I-F CRISPR-Cas systems and their cognate anti-CRISPR proteins, suggests that even the relatively small number of anti-CRISPR gene families discovered to date can have a broad impact on CRISPR-Cas systems in bacteria. As anti-CRISPR proteins have been reported to inhibit both Class 1 and Class 2 CRISPR-Cas systems, the methods described herein would be expected to identify additional anti-CRISPR proteins that might be capable of inhibiting all types and subtypes of CRISPR-Cas systems.

The data presented herein is the first to describe the existence of three different families of type II-C anti-CRISPR proteins. In one embodiment, the present invention contemplates anti-CRISPR proteins that block genome editing by NmeCas9 in cultured human cells. Although it is not necessary to understand the mechanism of an invention, it is believed that genetically encoded Cas9 inhibitors provide a means to spatially, temporally, or conditionally control Cas9 activity, thereby potentially allowing tissue-, cell cycle stage-, developmental stage-, or stimulus-specific inactivation of genome editing.

It is generally believed that target site precision and tissue specificity play a role when considering clinical CRISPR-Cas9 applications of gene therapy, where prolonged or misexpressed nuclease activity may exacerbate undesirable off-target effects. In one embodiment, the present invention contemplates an effective Cas9 off-switch that ameliorates off-target effects through expression or delivery strategies that enable anti-CRISPR proteins to accumulate whenever or wherever editing activity is unwanted. In one embodiment, the present invention contemplates methods comprising anti-CRISPR proteins for regulating a gene drive with CRISPR-Cas9 to force inheritance of desired alleles (e.g. in insect populations), possession of a functioning "off-switch" may provide a useful security or containment measure to avert unintended adverse consequences.

The data presented herein also show that anti-CRISPR proteins may bind directly to the NmeCas9/sgRNA complex and inhibit in vitro DNA cleavage. Given the completely unrelated sequences of these anti-CRISPR proteins, it may be expected that the anti-CRISPR proteins may abrogate activity through different mechanisms. This mechanism was the case for previously reported Type I-F anti-CRISPR proteins. Bondy-Denomy et al., 2015. As the data has determined that AcrIIC3Nme prevents stable genomic localization of sgRNA-loaded dNmeCas9 in mammalian cells, these proteins can be used as an off-switch for dNmeCas9-based applications. Alternatively, it remains possible that other anti-CRISPR proteins might allow NmeCas9 DNA-binding activity but prevent catalytic activation. If so, this mechanism would effectively create an NmeCas9 complex with a utility for modulation of transcription, similar to a type I-F anti-CRISPR protein. Dominguez et al., 2016; Wang et al., 2016; Bondy-Denomy et al., 2015.

It should be noted that CRISPR-Cas systems are present in approximately half of sequenced prokaryotic genomes and are widespread across diverse bacterial and archaeal lineages. The extreme diversity in, and purifying selective pressure on, CRISPR-Cas systems, combined with the co-occurrence of several different CRISPR-Cas system types in many genomes, is indicative of a dynamic co-evolutionary battle for survival between prokaryotes and parasitic MGEs. Makarova et al., 2015; Takeuchi et al., 2012. CRISPR-Cas systems are expected to pose a significant challenge to the process of horizontal gene transfer, especially given their ability to acquire heritable immunity against newly encountered threats and to upgrade their arsenal through new spacer acquisition. Barrangou et al., 2007; Fineran et al., 2014; Richter et al., 2014. However, recent studies have shown that the presence of a CRISPR Cas system does not correlate with lower levels of HGT over evolutionary timescales, or with a lower number of acquired prophage elements. Gophna et al., 2015; Touchon et al., 2016. We propose that widespread MGE-encoded anti-CRISPR proteins could reconcile this paradox. Also from an evolutionary perspective, it is noted that Cas9 from type II-A systems play a role not only for the interference function of existing spacers, but also for the adaptive acquisition of new spacers. Heler et al., 2015; Wei et al., 2015. If this adaptation role of type II-A Cas9 extends to type II-C systems, as seems likely, then Cas9-associating anti-CRISPR proteins may prevent the acquisition of new spacers in response to ongoing invasions.

A recent in vitro evolution study showed that the only way for phages to escape CRISPR338 mediated extinction is by the expression of an anti-CRISPR gene (van Houte et al., 2016). In strong accordance with the Red Queen theory, it has been reported that a total of seventeen distinct anti-CRISPR protein families are widespread among Proteobacteria, each inhibiting either type I-E, I-F, or II-C systems. Bondy-Denomy et al., 2013; Pawluk et al., 2014; Pawluk et al., 2016. The fact that anti-CRISPR proteins have evolved to inhibit both Class 1 and Class 2 CRISPR-Cas systems strongly suggests that they exist for other CRISPR-Cas types as well. FIG. 28A. It may be suggested that anti-CRISPR activity can have a large impact on CRISPR-Cas systems across prokaryotes and on horizontal gene transfer.

V. Kits

In one embodiment, the present invention contemplates a kit comprising an Acr protein. In one embodiment, the kits may be used for biological therapeutics. In one embodiment the kits may be used for gene drives. In one embodiment, the kit may be used for cell line manipulation. In one embodiment, the kit may be used for drug target validation.

VI. Pharmaceutical Formulations

The present invention further provides pharmaceutical compositions (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 μg to 100 g per kg of body weight, once or more daily, to once every 20 years.

VI. Composition Delivery Systems

The present invention contemplates several composition delivery systems that provide for roughly uniform distribution, have controllable rates of release of their components (e.g., vectors, proteins, nucleic acids, drugs etc.). A variety of different media are described below that are useful in creating composition delivery systems. It is not intended that any one medium or carrier is limiting to the present invention. Note that any medium or carrier may be combined with another medium or carrier; for example, in one embodiment a polymer microparticle carrier attached to a compound may be combined with a gel medium.

Carriers or mediums contemplated by this invention comprise a material selected from the group comprising gelatin, collagen, cellulose esters, dextran sulfate, pentosan polysulfate, chitin, saccharides, albumin, fibrin sealants, synthetic polyvinyl pyrrolidone, polyethylene oxide, polypropylene oxide, block polymers of polyethylene oxide and polypropylene oxide, polyethylene glycol, acrylates, acrylamides, methacrylates including, but not limited to, 2-hydroxyethyl methacrylate, poly(ortho esters), cyanoacrylates, gelatin-resorcin-aldehyde type bioadhesives, polyacrylic acid and copolymers and block copolymers thereof.

One embodiment of the present invention contemplates a composition delivery system comprising therapeutic agents as described herein.

Microparticles

One embodiment of the present invention contemplates a medium comprising a microparticle. Preferably, microparticles comprise liposomes, nanoparticles, microspheres, nanospheres, microcapsules, and nanocapsules. Preferably, some microparticles contemplated by the present invention comprise poly(lactide-co-glycolide), aliphatic polyesters including, but not limited to, poly-glycolic acid and poly-lactic acid, hyaluronic acid, modified polysacchrides, chitosan, cellulose, dextran, polyurethanes, polyacrylic acids, psuedo-poly(amino acids), polyhydroxybutrate-related copolymers, polyanhydrides, polymethylmethacrylate, poly(ethylene oxide), lecithin and phospholipids.

Liposomes

One embodiment of the present invention contemplates liposomes capable of attaching and releasing therapeutic agents described herein. Liposomes are microscopic spherical lipid bilayers surrounding an aqueous core that are made from amphiphilic molecules such as phospholipids. For example, a liposome may trap a therapeutic agent between the hydrophobic tails of the phospholipid micelle. Water soluble agents can be entrapped in the core and lipid-soluble agents can be dissolved in the shell-like bilayer. Liposomes have a special characteristic in that they enable water soluble and water insoluble chemicals to be used together in a medium without the use of surfactants or other emulsifiers. Liposomes can form spontaneously by forcefully mixing phosopholipids in aqueous media. Water soluble compounds are dissolved in an aqueous solution capable of hydrating phospholipids. Upon formation of the liposomes, therefore, these compounds are trapped within the aqueous liposomal center. The liposome wall, being a phospholipid membrane, holds fat soluble materials such as oils. Liposomes provide controlled release of incorporated compounds. In addition, liposomes can be coated with water soluble polymers, such as polyethylene glycol to increase the pharmacokinetic half-life. One embodiment of the present invention contemplates an ultra high-shear technology to refine liposome production, resulting in stable, unilamellar (single layer) liposomes having specifically designed structural characteristics. These unique properties of liposomes, allow the simultaneous storage of normally immiscible compounds and the capability of their controlled release.

In some embodiments, the present invention contemplates cationic and anionic liposomes, as well as liposomes having neutral lipids. Preferably, cationic liposomes comprise negatively-charged materials by mixing the materials and fatty acid liposomal components and allowing them to charge-associate. Clearly, the choice of a cationic or anionic liposome depends upon the desired pH of the final liposome mixture. Examples of cationic liposomes include lipofectin, lipofectamine, and lipofectace.

One embodiment of the present invention contemplates a medium comprising liposomes that provide controlled release of at least one therapeutic agent. Preferably, liposomes that are capable of controlled release: i) are biodegradable and non-toxic; ii) carry both water and oil soluble compounds; iii) solubilize recalcitrant compounds; iv) prevent compound oxidation; v) promote protein stabilization; vi) control hydration; vii) control compound release by variations in bilayer composition such as, but not limited to, fatty acid chain length, fatty acid lipid composition, relative amounts of saturated and unsaturated fatty acids, and physical configuration; viii) have solvent dependency; iv) have pH-dependency and v) have temperature dependency.

The compositions of liposomes are broadly categorized into two classifications. Conventional liposomes are generally mixtures of stabilized natural lecithin (PC) that may comprise synthetic identical-chain phospholipids that may or may not contain glycolipids. Special liposomes may comprise: i) bipolar fatty acids; ii) the ability to attach antibodies for tissue-targeted therapies; iii) coated with materials such as, but not limited to lipoprotein and carbohydrate; iv) multiple encapsulation and v) emulsion compatibility.

Liposomes may be easily made in the laboratory by methods such as, but not limited to, sonication and vibration. Alternatively, compound-delivery liposomes are commercially available. For example, Collaborative Laboratories, Inc. are known to manufacture custom designed liposomes for specific delivery requirements.

Microspheres, Microparticles and Microcapsules

Microspheres and microcapsules are useful due to their ability to maintain a generally uniform distribution, provide stable controlled compound release and are economical to produce and dispense. Preferably, an associated delivery gel or the compound-impregnated gel is clear or, alternatively, said gel is colored for easy visualization by medical personnel.

Microspheres are obtainable commercially (Proleasem, Alkerme's: Cambridge, Mass.). For example, a freeze dried medium comprising at least one therapeutic agent is homogenized in a suitable solvent and sprayed to manufacture microspheres in the range of 20 to 90 μm. Techniques are then followed that maintain sustained release integrity during phases of purification, encapsulation and storage. Scott et al., *Improving Protein Therapeutics With Sustained Release Formulations*, Nature Biotechnology, Volume 16:153-157 (1998).

Modification of the microsphere composition by the use of biodegradable polymers can provide an ability to control the rate of therapeutic agent release. Miller et al., *Degradation Rates of Oral Resorbable Implants* (*Polylactates and Polyglycolates: Rate Modification and Changes in PLA/PGA Copolymer Ratios*, J. Biomed. Mater. Res., Vol. II:711-719 (1977).

Alternatively, a sustained or controlled release microsphere preparation is prepared using an in-water drying method, where an organic solvent solution of a biodegradable polymer metal salt is first prepared. Subsequently, a dissolved or dispersed medium of a therapeutic agent is added to the biodegradable polymer metal salt solution. The weight ratio of a therapeutic agent to the biodegradable polymer metal salt may for example be about 1:100000 to about 1:1, preferably about 1:20000 to about 1:500 and more preferably about 1:10000 to about 1:500. Next, the organic solvent solution containing the biodegradable polymer metal salt and therapeutic agent is poured into an aqueous phase to prepare an oil/water emulsion. The solvent in the oil phase is then evaporated off to provide microspheres. Finally, these microspheres are then recovered, washed and lyophilized. Thereafter, the microspheres may be heated under reduced pressure to remove the residual water and organic solvent.

Other methods useful in producing microspheres that are compatible with a biodegradable polymer metal salt and therapeutic agent mixture are: i) phase separation during a gradual addition of a coacervating agent; ii) an in-water drying method or phase separation method, where an antiflocculant is added to prevent particle agglomeration and iii) by a spray-drying method.

In one embodiment, the present invention contemplates a medium comprising a microsphere or microcapsule capable of delivering a controlled release of a therapeutic agent for a duration of approximately between 1 day and 6 months. In one embodiment, the microsphere or microparticle may be colored to allow the medical practitioner the ability to see the medium clearly as it is dispensed. In another embodiment, the microsphere or microcapsule may be clear. In another embodiment, the microsphere or microparticle is impregnated with a radio-opaque fluoroscopic dye.

Controlled release microcapsules may be produced by using known encapsulation techniques such as centrifugal extrusion, pan coating and air suspension. Such microspheres and/or microcapsules can be engineered to achieve desired release rates. For example, Oliosphere® (Macromed) is a controlled release microsphere system. These particular microsphere's are available in uniform sizes ranging between 5-500 μm and composed of biocompatible and biodegradable polymers. Specific polymer compositions of a microsphere can control the therapeutic agent release rate such that custom-designed microspheres are possible, including effective management of the burst effect. ProMaxx® (Epic Therapeutics, Inc.) is a protein-matrix delivery system. The system is aqueous in nature and is adaptable to standard pharmaceutical delivery models. In particular, ProMaxx® are bioerodible protein microspheres that deliver both small and macromolecular drugs, and may be customized regarding both microsphere size and desired release characteristics.

In one embodiment, a microsphere or microparticle comprises a pH sensitive encapsulation material that is stable at a pH less than the pH of the internal mesentery. The typical range in the internal mesentery is pH 7.6 to pH 7.2. Consequently, the microcapsules should be maintained at a pH of less than 7. However, if pH variability is expected, the pH sensitive material can be selected based on the different pH criteria needed for the dissolution of the microcapsules. The encapsulated compound, therefore, will be selected for the pH environment in which dissolution is desired and stored in a pH preselected to maintain stability. Examples of pH sensitive material useful as encapsulants are Eudragit® L-100 or S-100 (Rohm GMBH), hydroxypropyl methylcellulose phthalate, hydroxypropyl methylcellulose acetate succinate, polyvinyl acetate phthalate, cellulose acetate phthalate, and cellulose acetate trimellitate. In one embodiment, lipids comprise the inner coating of the microcapsules. In these compositions, these lipids may be, but are not limited to, partial esters of fatty acids and hexitiol anhydrides, and edible fats such as triglycerides. Lew C. W., *Controlled-Release pH Sensitive Capsule And Adhesive System And Method*. U.S. Pat. No. 5,364,634 (herein incorporated by reference).

In one embodiment, the present invention contemplates a microparticle comprising a gelatin, or other polymeric cation having a similar charge density to gelatin (i.e., poly-L-lysine) and is used as a complex to form a primary microparticle. A primary microparticle is produced as a mixture of the following composition: i) Gelatin (60 bloom, type A from porcine skin), ii) chondroitin 4-sulfate (0.005%-0.1%), iii) glutaraldehyde (25%, grade 1), and iv) 1-ethyl-3-(3-dimethylaminopropyl)-carbodiimide hydrochloride (EDC hydrochloride), and ultra-pure sucrose (Sigma Chemical Co., St. Louis, Mo.). The source of gelatin is not thought to be critical; it can be from bovine, porcine, human, or other animal source. Typically, the polymeric cation is between 19,000-30,000 daltons. Chondroitin sulfate is then added to the complex with sodium sulfate, or ethanol as a coacervation agent.

Following the formation of a microparticle, a therapeutic agent is directly bound to the surface of the microparticle or is indirectly attached using a "bridge" or "spacer". The amino groups of the gelatin lysine groups are easily derivatized to provide sites for direct coupling of a compound. Alternatively, spacers (i.e., linking molecules and derivatizing moieties on targeting ligands) such as avidin-biotin are also useful to indirectly couple targeting ligands to the microparticles. Stability of the microparticle is controlled by the amount of glutaraldehyde-spacer crosslinking induced by the EDC hydrochloride. A controlled release medium is also empirically determined by the final density of glutaraldehyde-spacer crosslinks.

In one embodiment, the present invention contemplates microparticles formed by spray-drying a composition comprising fibrinogen or thrombin with a therapeutic agent. Preferably, these microparticles are soluble and the selected protein (i.e., fibrinogen or thrombin) creates the walls of the microparticles. Consequently, the therapeutic agents are incorporated within, and between, the protein walls of the microparticle. Heath et al., *Microparticles And Their Use In Wound Therapy*. U.S. Pat. No. 6,113,948 (herein incorporated by reference). Following the application of the microparticles to living tissue, the subsequent reaction between the fibrinogen and thrombin creates a tissue sealant thereby releasing the incorporated compound into the immediate surrounding area.

One having skill in the art will understand that the shape of the microspheres need not be exactly spherical; only as very small particles capable of being sprayed or spread into or onto a surgical site (i.e., either open or closed). In one embodiment, microparticles are comprised of a biocompatible and/or biodegradable material selected from the group consisting of polylactide, polyglycolide and copolymers of lactide/glycolide (PLGA), hyaluronic acid, modified polysaccharides and any other well known material.

VII. Phage Therapy

In one embodiment, the present invention contemplates a composition comprising bacteriophage genes, a Type II Cas9/sgRNA gene complex, and a gene encoding an Acr protein. In one embodiment, the present invention contemplates a method, comprising; a) providing; i) a patient comprising an infection by a bacteria, wherein said bacteria comprises a CRISPR-Cas9 system; and ii) a bacteriophage comprising a gene encoding an Acr protein; b) administering said bacteriophage to said patient such that said bacteriophage contacts said bacteria; c) injecting said bacteria with said Acr gene under conditions that said Acr gene is expressed; and d) inhibiting said bacterial CRISPR-Cas9 system with said expressed Acr gene. In one embodiment, the bacteriophage further comprises a CRISPR-Cas9 gene complex comprising a sgRNA sequence that is capable of binding to a bacterial gene target site. In one embodiment, the bacteriophage CRISPR-Cas9 gene complex is expressed in said bacteria and edits said bacterial gene.

Although it is not necessary to understand the mechanism of an invention, it is believed that some bacteria have CRISPR-Cas systems that would inactivate the phage, therefore making conventional phage therapy extremely ineffective. In one embodiment, the method further comprises administering an Acr protein to inhibit a bacterial CRISPR-Cas system thereby permitting a productive phage infection, and subsequent reduction of bacterial infection symptoms. Notably, *Neisseria meningitidis* and the closely related *Neisseria gonorrhoeae* are human pathogens for which phage therapy may be extremely useful as they are rapidly acquiring antibiotic resistance.

In one embodiment, the present invention contemplates a method of phage therapy on mammalian cells. Phage therapy or viral phage therapy is the therapeutic use of bacteriophages to treat pathogenic infections. Phage therapy has many potential applications in human medicine as well as dentistry, veterinary science, and agriculture. If the target host of a phage therapy treatment is not an animal the term "biocontrol" (as in phage-mediated biocontrol of bacteria) is usually employed, rather than "phage therapy".

Although the natural hosts for bacteriophages are bacteria, a growing body of data shows that phages can also interact with some populations of mammalian cells, especially with cells of the immune system. In general, these interactions include two main aspects. The first is the phage immunogenicity, that is, the capacity of phages to induce specific immune responses, in particular the generation of specific antibodies against phage antigens. The other aspect includes the immunomodulatory activity of phages, that is, the nonspecific effects of phages on different functions of major populations of immune cells involved in both innate and adaptive immune responses. These functions include, among others, phagocytosis and the respiratory burst of phagocytic cells, the production of cytokines, and the generation of antibodies against nonphage antigens. The aim of this chapter is to discuss the interactions between phages and cells of the immune system, along with their implications for phage therapy. These topics are presented based on the results of experimental studies and unique data on immunomodulatory effects found in patients with bacterial infections treated with phage preparations. Górski et al., "Phage as a modulator of immune responses: practical implications for phage therapy" Adv Virus Res. 2012; 83:41-71.

Bacteriophage T4 is a virus with well-known genetics, structure, and biology. Such techniques as X-ray crystallography, cryo-EM, and three-dimensional (3D) image reconstruction allowed describing its structure very precisely. The genome of this bacteriophage was completely sequenced, which opens the way for the use of many molecular techniques, such as site-specific mutagenesis, which was widely applied, e.g., in investigating the functions of some essential T4 proteins. The phage-display method, which is commonly applied in bacteriophage modifications, was successfully used to display antigens (PorA protein, VP2 protein of vvIBDV, and antigens of anthrax and HIV) on T4's capsid platform. As first studies showed, the phage-display system as well as site-specific mutagenesis may also be used to modify interactions between phage particles and mammalian cells or to obtain phages infecting species other than the host bacteria. These may be used, among others, in the constantly developing bacteriophage therapy. All manipulations of this popular bacteriophage may enable the development of vaccine technology, phage therapy, and other branches of biological and medical science. Kurzepa et al., "Molecular modification of T4 bacteriophage proteins and its potential application-review" Folia Microbiol (Praha). 2009; 54(1):5-15. Epub 2009 Mar. 29.

Bacteriophages are viruses infecting bacteria and lack ability to infect mammalian cells but promises to be a novel divergent therapeutic approach. The great versatility of the phage system has led to the development of improved phage delivery vectors. Combination therapy based on multiple phage and other pharmaceutical treatments holds great promise. The potential therapeutic phage therapy arises from its lack of natural tropism for mammalian cells, resulting in no adverse effects. Sohrab et al., "Bacteriophage—a common divergent therapeutic approach for Alzheimer's disease and type II diabetes mellitus" CNS Neurol Disord Drug Targets. 2014 13(3):491-500.

Advances in phage therapy encourage scientific interest in interactions of phages with human and animal organisms. This has created a need for developing tools that facilitate studies of phage circulation and deposition in tissues and cells. A new green fluorescent protein (GFP)-based method has been disclosed to administer T4 phage molecular imaging in living systems. The method employs decoration of a phage capsid with GFP fused to the N-terminus of Hoc protein by in vivo phage display. Fluorescent phages were positively assessed as regards their applicability for detection inside living mammalian cells (by phagocytosis) and tissues (filtering and retention by lymph nodes and spleen). Kaźmierczak et al., "Molecular imaging of T4 phage in mammalian tissues and cells" Bacteriophage. 2014 4(1): e28364. Epub 2014 Feb. 27.

Developing nanomaterials that are effective, safe, and selective for gene transfer applications is challenging. Bacteriophages (phage), viruses that are generally known to infect bacteria only, have shown promise for targeted gene transfer applications. Unfortunately, limited progress has been achieved in improving their potential to overcome mammalian cellular barriers. Chemical modifications of the bacteriophage capsid have been proposed to improve targeted gene delivery by phage vectors into mammalian cells. For example, a hybrid system including two classes of nanomaterial systems, cationic polymers and M13 bacteriophage virus particles were genetically engineered to display a tumor-targeting ligand and carry a transgene cassette. A phage complex with cationic polymers generates positively charged phage and large aggregates show enhanced cell surface attachment, buffering capacity, and improved transgene expression while retaining cell type specificity. Moreover, phage/polymer complexes carrying a therapeutic gene achieve greater cancer cell killing than phage alone. This new class of hybrid nanomaterial platform can advance targeted gene delivery applications by bacteriophage. Yata et al., "Hybrid Nanomaterial Complexes for Advanced Phage-guided Gene Delivery" Mol Ther Nucleic Acids. 2014 Aug. 12; 3:e185.

EXPERIMENTAL

Example I

Construction of Acr Vectors

Sequences that are found to encode Acr proteins can be ordered from companies that market custom DNA sequence samples, or they can be PCR-amplified from suitable biological DNA samples. They can then be introduced into a vector (including, but not limited to, plasmids and viral vectors) by standard recombinant DNA cloning protocols (e.g. restriction endonuclease digestion and religation, or Gibson assembly). The vector commonly includes promoter sequences suitable for expression within the cells of interest. They also contain other sequences that facilitate gene expression and control [e.g., 5' and 3' untranslated regions, poly(A) signals, and transcription terminators]. These vectors can then be introduced into target cells using standard delivery approaches that are well known in the field.

Example II

Screening for Acr Protein Candidates

Many other acr gene candidates can be identified by their genetic association with aca genes or putative aca genes. Acr open reading frames can be cloned directly from the species of origin, or, alternatively, the gene sequence can be synthesized by a company. There are several ways to screen for Acr activity against the Type II system. 1) test for inhibition of NmeCas9 activity in its native context, i.e. in *Neisseria meningitidis* by using a previously described assay measuring the transformation efficiency of CRISPR-Cas9 targeted DNA; 2) test for inhibition of NmeCas9 activity in a heterologous *E. coli* system whereby NmeCas9 is programmed to target *E. coli* bacteriophage (e.g. lambda phage); 3) test for inhibition of NmeCas9 activity in human cell culture using the T7E1 assays described herein.

Example III

Acr Administration to Control the Spread of Gene Drives

Cas9 is currently being contemplated for use in gene drives, which are engineered genetic elements that can spread rapidly through a natural population. If that natural population is an undesirable one, e.g. an insect that transmits a pathogen such as the malaria parasite or dengue virus, then the gene drive could include elements that induce death or sterility to any insect that acquires the gene drive. Although the potential of this approach to control insect-borne diseases is widely recognized, there are many concerns about their safety and the potential for unintended adverse consequences (predictable or not) upon release into the natural environment. Part of this concern arises from the possibility that spread of the gene drive could be difficult or impossible to stop once it is released. A gene drive could be envisioned that uses a Type II-C Cas9 enzyme, e.g. NmeCas9, to support its propagation. Prior to release of the gene drive, a separate insect population could be generated that is engineered to express the Acr protein, rendering them resistant to the gene drive. If adverse consequences of gene drive propagation become apparent, the Acr-expressing insect population could be released to slow the propagation of the gene drive through the population.

Example IV

Acr Administration for Biological Therapeutics

NmeCas9 and its sgRNA could be encoded in a vector and then introduced into the cells of a patient for purposes of therapeutic genome editing. Once the intended editing has occurred, further NmeCas9 activity is undesirable: because the intended editing site has been altered, the only potential editing sites left are unintended ones. DNA cleavage at unintended sites could be harmful to the patient (for example, they could induce oncogenic chromosome translocations). After the intended editing event has occurred, a vector encoding the Acr protein could be introduced into the patient's cells to inhibit NmeCas9 from that point forward, preventing these unintended DNA cleavage events from occurring.

Example V

Creation of Acr Fusion Proteins

Two Acrs that are found to bind different areas on the surface of the Cas9 protein may be fused together to provide potentially synergistic effects on Cas9 inhibition. Non-competitive, simultaneous binding can be detected using in vitro experiments where the Cas9 protein is saturated with one Acr, and then a second Acr is added and its binding is assessed. If the second Acr can bind to Cas9 without displacing the first Acr, then their binding must be non-competitive and they bind to non-overlapping areas on the Cas9 protein. This is conceivable because the Cas9 protein is much larger (>10× larger) than any of the Acrs. A fusion of such non-competitive Acrs can be achieved by creating a synthetic construct that will express both Acr open reading frames in frame with one another, separated by a flexible peptide linker. Several lengths and compositions of this linker can be tested to achieve maximal activity.

Example VI

Bioinformatics Analysis

BLASTp searches for Aca2 were conducted with WP_019933869.1 from *Oceanimonas smirnovii* as the query (Pawluk et al., 2016). BLASTp searches for Aca3 were conducted with WP_049360086.1 from *Neisseria meningitidis* as the query. Information from Makarova et al. (2015), encompassing a representative list of CRISPR-Cas interference proteins, was used to create a sequence similarity dendogram of CRISPR-Cas interference modules for all known CRISPR-Cas types (Makarova et al., 2015). For the phylogenetic analysis of Cas9 protein sequences, a list of 257 representative Cas9 protein sequences was extracted from a previous analysis (Fonfara et al., 2014) and updated with newly deposited sequences in the NCBI Protein database. The list was manually trimmed so that only one representative from each species remained. After alignment of the sequences with MUSCLE (Edgar, 2004), FastTree was used to create an unrooted maximum likelihood tree (Price et al., 2009, 2010). Bootstrap values are shown at each node. Based on the data from Fonfara et al. (2014), each clade was classified into subtype II-A (blue), II-B (yellow), or II-C (purple). Clades on the tree are coloured in red if they belong to any genus where a validated type II-C anti-CRISPR gene or its ortholog was found. Some noteworthy Cas9 proteins are highlighted on the tree by asterisks.

Example VII

Plasmid Construction

Acr expression vectors for protein purification DNA sequences encoding candidate anti-CRISPR proteins were synthesized by GenScript (Piscataway, NJ, USA) and subcloned into pHAT4 (Peranen et al., 1996) using NcoI-HindIII restriction sites. The gene encoding AcrE2 was amplified by PCR from *Pseudomonas* phage JBD88a and ligated into pHAT4 using NcoI-HindIII restriction sites. Table 1 contains the DNA and protein sequences of the anti-CRISPR proteins tested in this study. AcrIIC3Nme was found to be significantly more soluble upon addition of an N-terminal FLAG tag, so that construct was used for in vitro analyses.

Example VIII

Cas9:sgRNA Vector for Protein Purification

A DNA encoding a minimal T7 promoter upstream of a random sequence sgRNA (i.e. no genomic target in *E. coli*) having the following sequence (SEQ ID NO: 97):

```
5'-TGAGACCAGTCTCGGAAGCTCAAAGGTCTCGTTGTAGCTCCCTTTCT

CATTTCGGAA ACGAAATGAGAACCGTTGCTACAATAAGGCCGTCTGAAA
```

-continued

```
AGATGTGCCGCAACGCT CTGCCCCTTAAAGCTTCTGCTTTAAGGGGCAT

CGTTTATTTCGGTTAAAAAATGCCGT -3'
```

was synthesized by GenScript (Piscataway, NJ, USA). This insert was cloned into the previously described pMCSG7-NmeCas9 expression vector (Zhang et al., 2015), downstream of the NmeCas9 protein-coding region, into the SalI-XhoI restriction sites.

Example IX

Cas9/sgRNA Mammalian Expression Vectors

For editing of DTS3 and DTS7 by both SpyCas9 and NmeCas9 we used Cas9 expression vectors that were identical in all respects [plasmid backbone, CMV IE94 promoter (Villefranc et al., 2007), UTRs, terminal fusions of NLSs and epitope tags, etc.] except for the respective Cas9 ORFs.

The SpyCas9 expression plasmid (pEJS24) has been described previously (Bolukbasi et al., 2015) and the NmeCas9 expression plasmid (pEJS424) was generated from (pEJS24) by Cas9 ORF replacement via Gibson assembly (New England Biolabs). Similarly, plasmids for the expression of sgRNAs for each Cas9 ortholog were also identical in all respects except for the sgRNA sequences themselves. The SpyCas9 sgRNA plasmid pLKO.1-puro has been described previously (Kearns et al., 2014), and the NmeCas9 sgRNA expression plasmid (pEJS333) was generated from it by Gibson assembly. The plasmids expressing NmeCas9 and its sgRNA are described in detail elsewhere (Amrani et al., manuscript in preparation). For editing of the N-TSIC, N-TS4B, N-TS4C, N-TS7, N-TS8, N-TS11 and N-TS25 sites, an all-in-one vector (pEJS15) was used expressing both NmeCas9 (under the control of the EF-1a promoter) and its sgRNA (under the control of the U6 promoter). This plasmid, which was derived from pSimpleII (Hou et al., 2013), is also described elsewhere (Amrani et al., manuscript in preparation). The 24-nt guide sequences for each distinct target site were inserted into the sgRNA cassette of pEJS15 by the ligation of synthetic oligonucleotide duplexes into its BsmBI sites.

Example X

Acr Vectors for Mammalian Expression

To generate the Acr expression plasmids p427-AcrE2, p430-AcrIIC1Boe, p433-AcrIIC1Nme, p436-AcrIIC2Nme, and p443-AcrIIC3Nme, each ORF was synthesized as a gene block (Integrated DNA Technologies) flanked by XhoI and BstBI sites, with a Kozak consensus sequence upstream of the initiation codon. The synthetic Acr sequences were then inserted into the XhoI and BstBI sites of the pCS2-Dest vector (Addgene). The resulting plasmids placed the Acr-encoding genes under the control of the CMV IE94 promoter.

Example XI

*Neisseria meningitidis* Transformation

Candidate anti-CRISPR genes with the native NmeCas9 promoter and Shine-Dalgarno sequence were cloned into pGCC2, a *N. meningitidis* vector containing homology arms for integration of the insert into the *N. meningitidis* chromosome at the nics locus, as described previously (Zhang et al., 2013). The pGCC2 constructs were transformed into *N.*

*meningitidis strain* 8013, and erythromycin-resistant transformants were selected. Two or three representative transformants per reaction were verified by re-streaking on selective plates twice and then confirmed by PCR on purified genomic DNA. This procedure resulted in *N. meningitidis* strain derivatives with chromosomally integrated anti-CRISPR genes under the control of the native promoter of *N. meningitidis* Cas9. In all cases, the CRISPR locus was sequence-confirmed in the derived strains to ensure that the spacers to be tested for interference activity were intact.

Transformation assays to assess CRISPR-Cas activity of these strains were completed as described previously (Duffin and Seifert, 2012; Zhang et al., 2013), with protospacer 25 (i.e., complementary to the crRNA derived from endogenous CRISPR spacer #25) as the target. Briefly, 150 ng of plasmids were used per transformation reaction and 10 μL of serial 10-fold dilutions were spotted on GCB plates in triplicate in the presence and absence of appropriate antibiotics. 200 μL from the undiluted final transformation mixture were also plated on GCB plates with appropriate antibiotics to enhance detection.

Eight representative transformants per reaction were verified by re-streaking on selective plates twice and then verified by PCRs on cell extracts. Transformation frequencies were reported as antibiotic-resistant cfu/mL divided by total cfu/mL from at least three independent experiments (mean±s.e.m.). Cloning and purification of anti-CRISPR proteins anti-CRISPR proteins were purified from pHAT4 constructs expressed in *E. coli* BL21 as described previously (Bondy-Denomy et al., 2015). After elution from Ni-NTA resin, anti-CRISPR proteins were dialyzed in 10 mM Tris pH 7.5, 250 mM NaCl, and 5 mM β-mercaptoethanol and incubated with His-tagged Tobacco Etch Virus (TEV) protease overnight at 4° C. A second round of Ni-NTA purification was used to isolate successfully cleaved, untagged anti-CRISPR proteins by collecting the unbound fraction.

Example XII

Purification of Cas9

6×His-NmeCas9:sgRNA was expressed in *E. coli* Rosetta (DE3). Cells were grown in Terrific Broth (TB) medium at 37° C. to an optical density (OD600 nm) of 0.8 in the Lex Bubbling System (Structural Genomics Consortium, Toronto, Canada). Protein expression was induced by the addition of 1 mM IPTG for 16 h at 16° C. Cells were lysed by sonication in 50 mM Tris pH 7.5, 500 mM NaCl, 20 mM imidazole, 0.5 mM DTT and 5% glycerol supplemented with 0.5 mM PMSF, lysozyme and protease inhibitor cocktail (Sigma). Clarified lysates were bound in batch to Ni-NTA agarose (Qiagen), and bound protein was eluted with 300 mM imidazole. Purified Cas9:sgRNA was dialysed into 20 mM HEPES pH 7.5, 250 mM NaCl, 5% glycerol, 1 mM DTT and 1 mM PMSF) for protein interaction experiments. 6×His-MBP-tagged AnaCas9 was purified from *E. coli* BL21 Rosetta cells as described previously (Ma et al., 2015a).

Example XIII

Cas9-Anti-CRISPR Protein Pulldown Assays

Untagged anti-CRISPR proteins (after TEV cleavage) were incubated with and without NmeCas9 for 1 hour at 4° C. in binding buffer (20 mM HEPES pH 7.5, 250 mM NaCl, 5% glycerol, 5 mM imidazole), and input fractions were set aside for SDS-PAGE analysis. 50 μL 50% slurry Ni-NTA beads were added to each tube. After 30 minutes incubation at 4° C. with rotation, the beads were collected by centrifugation at 3000 rpm for 2 minutes. Beads were washed four times with 1 mL binding buffer supplemented with 20 mM imidazole and collected by centrifugation. Bound proteins were eluted with elution buffer (binding buffer containing 300 mM imidazole). The input and elution fractions were analyzed by SDS-PAGE followed by Coomassie staining.

Example XIV

In Vitro DNA Cleavage

NmeCas9 sgRNA derived from spacer (Zhang et al., 2015) was generated by in vitro T7 transcription (Ampliscribe). NmeCas9 (500 nM) was incubated with purified, recombinant anti-CRISPR protein in cleavage buffer [20 mM HEPES-KOH (pH 7.5), 150 mM KCl, 10% glycerol, 1 mM DTT, and 10 mM $MgCl_2$] for 10 minutes. Next, sgRNA (1:1, 500 nM) was added and the mixture was incubated for another 15 minutes. Linear plasmid containing the target protospacer was added to the Cas9/sgRNA complex at ~5 nM final concentration. The reactions were incubated at 37° C. for 30 minutes and visualized after electrophoresis in a 1% agarose/1×TAE gel.

Example XV

Mammalian Genome Editing Plasmids

Plasmids for mammalian expression of NmeCas9, SpyCas9, their respective sgRNAs, and the anti-CRISPR proteins are disclosed herein. Table 4.

TABLE 4

Plasmids Useful For Mammalian Expression of Cas9 System

| PLASMID | PLASMID DESCRIPTION | SOURCE |
|---|---|---|
| | *N. meningitidis* interference assays | |
| pGCC2/$P_{cas9}$ + AcrIIC1$_{Boe}$ | For strain nics::$P_{cas9}$-AcrIIC1$_{Boe}$ | This study |
| pGCC2/$P_{cas9}$ + AcrIIC1$_{Nme}$ | For strain nics::$P_{cas9}$-AcrIIC1$_{Nme}$ | This study |
| pGCC2/$P_{cas9}$ + AcrIIC2$_{Nme}$ | For strain nics::$P_{cas9}$-AcrIIC2$_{Nme}$ | This study |
| pGCC2/$P_{cas9}$ + AcrIIC3$_{Nme}$ | For strain nics::$P_{cas9}$-AcrIIC3$_{Nme}$ | This study |
| | In vitro protein-protein interactions | |
| pHAT4-AcrE2 | 6xHis-TEV-AcrE2 | This study |
| pHAT4-AcrIIC1$_{Boe}$ | 6xHis-TEV-AcrIIC1$_{Boe}$ | This study |
| pHAT4-AcrIIC1$_{Nme}$ | 6xHis-TEV-AcrIIC1$_{Nme}$ | This study |

TABLE 4-continued

| PLASMID | PLASMID DESCRIPTION | SOURCE |
|---|---|---|
| Plasmids Useful For Mammalian Expression of Cas9 System | | |
| pHAT4-AcrIIC2$_{Nme}$ | 6xHis-TEV-AcrIIC2$_{Nme}$ | This study |
| pHAT4-AcrIIC3$_{Nme}$ | 6xHis-TEV-FLAG-AcrIIC3$_{Nme}$ | This study |
| pMCSG7-NmeCas9:sgRNA | 6xHis-TEV-NmeCas9 + sgRNA$_{nontarget}$ | This study; derived from Zhang et al 2015 |
| In vitro DNA cleavage assays | | |
| pEJS560 | Protospacer 25 - pUC19 | E. Sontheimer Lab |
| pEJS561 | 6xHis-TEV-WtNmeCas9 - pMCSG7 | E. Sontheimer Lab |
| Genome Editing | | |
| pEJS24 | pCSDest2-SpyCas9-NLS-3XHA-NLS | S. Wolfe Lab |
| pEJS424 | pCSDest2-NmeCas9-NLS-3XHA-NLS | E. Sontheimer Lab |
| pEJS427 | pCSDest2-AcrE2 | This study |
| pEJS430 | pCSDest2-AcrIIC1$_{Boe}$ | This study |
| pEJS433 | pCSDest2-AcrIIC1$_{Nme}$ | This study |
| pEJS436 | pCSDest2-AcrIIC2$_{Nme}$ | This study |
| pEJS443 | pCSDest2-AcrIIC3$_{Nme}$ | This study |
| pEJS333 | pLKO.1-puro U6 Nme-sgRNA BfuAI stuffer | S. Wolfe Lab |
| pEJS334 | pLKO.1-puro U6 Spy-sgRNA BfuAI Stuffer | S. Wolfe Lab |
| pEJS15 | pSimpleII-NmeCas9-sgRNA/Empty | E. Sontheimer Lab |
| Fluorescence Imaging | | |
| pEJS333 | pLKO.1-puro U6 Nme-sgRNA BfuAI stuffer | S. Wolfe Lab |
| pEJS334 | pLKO.1-puro U6 Spy-sgRNA BfuAI stuffer | S. Wolfe Lab |
| pEJS466 | pHAGE-TO-Nme dCas9-3xGFP | Addgene #64109 |
| pEJS467 | pHAGE-TO-Spy dCas9-3xmCherry | Addgene #64108 |
| pEJS468 | pLK.O1-NmeSgRNA/DTS13-Telomere | This study |
| pEJS469 | pLK.O1-SpySgRNA/DTS13-Telomere | This study |
| pEJS476 | pHAGE-TO-Nme dCas9 3XGFP-SgRNA/ Telomere-All-in-one | This study |
| pEJS477 | pHAGE-TO-Spy dCas9 3XmCherry-SgRNA/ Telomere-All-in-one | This study |
| pEJS478 | pIRES-mTagBFP2 | D. Grünwald Lab |
| pEJS507 | pCDest2-noAcr-mTagBFP2-IRES | This study |
| pEJS481 | pCDest2-AcrE2-mTagBFP2-IRES | This study |
| pEJS480 | pCDest2-AcrIIC1$_{Boe}$-mTagBFP2-IRES | This study |
| pEJS501 | pCDest2-AcrIIC1$_{Nme}$-mTagBFP2-IRES | This study |
| pEJS502 | pCDest2-AcrIIC2$_{Nme}$-mTagBFP2-IRES | This study |
| pEJS482 | pCDest2-AcrIIC3$_{Nme}$-mTagBFP2-IRES | This study |

Approximately $1.5\times10^5$ mid-passage HEK293T cells cultured at 37° C., 5% CO2 in DMEM+10% FBS+1% Penicillin/Streptomycin (Gibco) were transiently transfected with 150 ng Cas9-expressing plasmid and 150 ng sgRNA expressing plasmid, using Polyfect transfection reagent (Qiagen) in 24-well plates according to the manufacturer's instructions. Alternatively, 200 ng of an all-in-one plasmid expressing both NmeCas9 and the appropriate sgRNA was used for transfection.

For experiments that included Acr protein expression, 100 ng of the Acr plasmid was included in the co-transfection mix. 72 hours after transfection, cells were harvested and genomic DNA was extracted with the DNeasy Blood and Tissue kit (Qiagen) according to the manufacturer's instructions. 50 ng genomic DNA was used for PCR amplification (High Fidelity 2×PCR Master Mix (New England Biolabs) with primers flanking the targeted site. 10 µl of each PCR product was heat denatured, re-annealed, and digested with T7 Endonuclease I (New England Biolabs). The samples were fractionated in a 2.5% agarose/1×TAE gel and quantified with the ImageMaster-TotalLab program. Indel percentages ("% lesion" in the figures) were calculated as previously described (Guschin et al., 2010).

Example VI

Fluorescence Microscopy of dNmeCas9 dNmeCas9-(sfGFP)$_3$, dSpyCas9-(mCherry)$_3$, and anti-CRISPR/mTagBFP2 plasmids were used in U2OS cells cultured at 37° C. (5% CO2) in DMEM (Life Technologies) supplemented with 10% FBS and 1% Pen/Strep. For imaging, cells were grown on 170 µm, 35×10 mm glass-bottom dishes (Eppendorf). Cells were cotransfected with 300 ng of all-in-one plasmids (150 ng of each dNmeCas9 and dSpyCas9 plasmid), an additional 600 ng of sgRNA-expressing plasmids, and 100 ng of anti-CRISPR/mTagBFP2 plasmid using PolyFect (Qiagen) according to the manufacturer's instructions. After 24 hours of incubation, live cells were imaged with a Leica DMi8 microscope equipped with Hamamatsu camera (C11440-22CU), 65× oil objective lens, and Microsystems software (LASX). Further imaging processing was done with ImageJ.

REFERENCE LIST 1

1. Doudna, J. A. & Charpentier, E. Genome editing. The new frontier of genome engineering with CRISPR-Cas9. Science 346, 1258096-1258096 (2014).
2. Sander, J. D. & Joung, J. K. CRISPR-Cas systems for editing, regulating and targeting genomes. Nature biotechnology 32, 347-355 (2014).

3. Hsu, P. D., Lander, E. S. & Zhang, F. Development and Applications of CRISPRCas9 for Genome Engineering. Cell 157, 1262-1278 (2014).
4. Jinek, M. et al. A programmable dual-RNA-guided DNA endonuclease in adaptive bacterial immunity. Science 337, 816-821 (2012).
5. Sternberg, S. H., Redding, S., Jinek, M., Greene, E. C. & Doudna, J. A. DNA interrogation by the CRISPR RNA-guided endonuclease Cas9. Nature 507, 62-67 (2014).
6. Szczelkun, M. D. et al. Direct observation of R-loop formation by single RNA guided Cas9 and Cascade effector complexes. Proceedings of the National Academy of Sciences 111, 9798-(2014).
7. Anders, C., Niewoehner, O., Duerst, A. & Jinek, M. Structural basis of PAM dependent target DNA recognition by the Cas9 endonuclease. Nature 513, 569-573 (2014).
8. Jiang, F., Zhou, K., Ma, L., Gressel, S. & Doudna, J. A. STRUCTURAL BIOLOGY. A Cas9-guide RNA complex preorganized for target DNA recognition. Science 348, 1477-1481 (2015).
9. Hsu, P. D. et al. DNA targeting specificity of RNA-guided Cas9 nucleases. Nature biotechnology 31, 827-832 (2013).
10. Tsai, S. Q. et al. Dimeric CRISPR RNA-guided FokI nucleases for highly specific genome editing. Nature biotechnology 32, 569-576 (2014).
11. Zhang, Y. et al. Comparison of non-canonical PAMs for CRISPR/Cas9-mediated DNA cleavage in human cells. Sci Rep 4, 5405 (2014).

REFERENCE LIST 2

Barrangou, R., Fremaux, C., Deveau, H., Richards, M., Boyaval, P., Moineau, S., Romero, D. A., and Horvath, P. (2007). CRISPR provides acquired resistance against viruses in prokaryotes. Science 315, 1709-1712.

Bikard, D., Euler, C. W., Jiang, W., Nussenzweig, P. M., Goldberg, G. W., Duportet, X., Fischetti, V. A., and Marraffini, L. A. (2014). Exploiting CRISPR-Cas nucleases to produce specific antimicrobials. Nat Biotechnol 32, 1146-1150.

Bolukbasi, M. F., Gupta, A., and Wolfe, S. A. (2015). Creating and evaluating accurate CRISPR Cas9 scalpels for genomic surgery. Nat Methods 13, 41-50.

Bondy-Denomy, J., Garcia, B., Strum, S., Du, M., Rollins, M. F., Hidalgo-Reyes, Y., Wiedenheft, B., Maxwell, K. L., and Davidson, A. R. (2015). Multiple mechanisms for CRISPR-Cas inhibition by anti-CRISPR proteins. Nature.

Bondy-Denomy, J., Pawluk, A., Maxwell, K. L., and Davidson, A. R. (2013). Bacteriophage genes that inactivate the CRISPR/Cas bacterial immune system. Nature 493, 429-432.

Cho, S. W., Kim, S., Kim, J. M., and Kim, J. S. (2013). Targeted genome engineering in human cells with the Cas9 RNA-guided endonuclease. Nat Biotechnol 31, 230-232.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Deltcheva, E., Chylinski, K., Sharma, C. M., Gonzales, K., Chao, Y., Pirzada, Z. A., Eckert, M. R., Vogel, J., and Charpentier, E. (2011). CRISPR RNA maturation by trans-encoded small RNA and host factor RNase III. Nature 471, 602-607.

Dominguez, A. A., Lim, W. A., and Qi, L. S. (2016). Beyond editing: repurposing CRISPR-Cas9 for precision genome regulation and interrogation. Nat Rev Mol Cell Biol 17, 5-15.

Duffin, P. M., and Seifert, H. S. (2012). Genetic transformation of *Neisseria gonorrhoeae* shows a strand preference. FEMS Microbiol Lett 334, 44-48.

Ebina, H., Misawa, N., Kanemura, Y., and Koyanagi, Y. (2013). Harnessing the CRISPR/Cas9 system to disrupt latent HIV-1 provirus. Sci Rep 3, 2510.

Edgar, R. C. (2004). MUSCLE: multiple sequence alignment with high accuracy and high throughput. Nucleic Acids Res 32, 1792-1797.

Esvelt, K. M., Mali, P., Braff, J. L., Moosburner, M., Yaung, S. J., and Church, G. M. (2013). Orthogonal Cas9 proteins for RNA-guided gene regulation and editing. Nat Methods 10, 1116-568 1121.

Fineran, P. C., Gerritzen, M. J., Suarez-569 Diez, M., Kunne, T., Boekhorst, J., van Hijum, S. A., Staals, R. H., and Brouns, S. J. (2014). Degenerate target sites mediate rapid primed CRISPR adaptation. Proc Natl Acad Sci USA 111, E1629-1638.

Fonfara, I., Le Rhun, A., Chylinski, K., Makarova, K. S., Lecrivain, A. L., Bzdrenga, J., Koonin, E. V., and Charpentier, E. (2014). Phylogeny of Cas9 determines functional exchangeability of dual-RNA and Cas9 among orthologous type II CRISPR-Cas systems. Nucleic Acids Res 42, 2577-2590.

Fu, Y., Sander, J. D., Reyon, D., Cascio, V. M., and Joung, J. K. (2014). Improving CRISPR-Cas nuclease specificity using truncated guide RNAs. Nat Biotechnol 32, 279-284.

Gantz, V. M., Jasinskiene, N., Tatarenkova, O., Fazekas, A., Macias, V. M., Bier, E., and James, A. A. (2015). Highly efficient Cas9-mediated gene drive for population modification of the malaria vector mosquito *Anopheles stephensi*. Proc Natl Acad Sci USA 112, E6736-6743.

Gasiunas, G., Barrangou, R., Horvath, P., and Siksnys, V. (2012). Cas9-crRNA ribonucleoprotein complex mediates specific DNA cleavage for adaptive immunity in bacteria. Proc Natl Acad Sci USA 109, E2579-2586.

Gomaa, A. A., Klumpe, H. E., Luo, M. L., Selle, K., Barrangou, R., and Beisel, C. L. (2014). Programmable removal of bacterial strains by use of genome-targeting CRISPR-Cas systems. MBio 5, e00928-00913.

Gophna, U., Kristensen, D. M., Wolf, Y. I., Popa, O., Drevet, C., and Koonin, E. V. (2015). No evidence of inhibition of horizontal gene transfer by CRISPR-Cas on evolutionary timescales. ISME J 9, 2021-2027.

Guschin, D. Y., Waite, A. J., Katibah, G. E., Miller, J. C., Holmes, M. C., and Rebar, E. J. (2010). A rapid and general assay for monitoring endogenous gene modification. Methods Mol Biol 649, 247-256.

Hammond, A., Galizi, R., Kyrou, K., Simoni, A., Siniscalchi, C., Katsanos, D., Gribble, M., Baker, D., Marois, E., Russell, S., et al. (2016). A CRISPR-Cas9 gene drive system targeting female reproduction in the malaria mosquito vector Anopheles gambiae. Nat Biotechnol 34, 78-596 83.

Heler, R., Samai, P., Modell, J. W., Weiner, C., Goldberg, G. W., Bikard, D., and Marraffini, L. A. (2015). Cas9 specifies functional viral targets during CRISPR-Cas adaptation. Nature 519, 199-202.

Hilton, I. B., D'Ippolito, A. M., Vockley, C. M., Thakore, P. I., Crawford, G. E., Reddy, T. E., and Gersbach, C. A. (2015). Epigenome editing by a CRISPR-Cas9-based acetyltransferase activates genes from promoters and enhancers. Nat Biotechnol 33, 510-517.

Hirano, H., Gootenberg, J. S., Horii, T., Abudayyeh, O. O., Kimura, M., Hsu, P. D., Nakane, T., Ishitani, R., Hatada, I., Zhang, F., et al. (2016). Structure and Engineering of Francisella novicida Cas9. Cell 164, 950-961.

Hou, Z., Zhang, Y., Propson, N. E., H 606 owden, S. E., Chu, L. F., Sontheimer, E. J., and Thomson, J. A. (2013). Efficient genome engineering in human pluripotent stem cells using Cas9 from *Neisseria meningitidis*. Proc Natl Acad Sci USA 110, 15644-15649.

Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nat Biotechnol 31, 827-832.

Hwang, W. Y., Fu, Y., Reyon, D., Maeder, M. L., Kaini, P., Sander, J. D., Joung, J. K., Peterson, R. T., and Yeh, J. R. (2013). Heritable and precise zebrafish genome editing using a CRISPR-Cas system. PLoS One 8, e68708.

Jiang, W., Bikard, D., Cox, D., Zhang, F., and Marraffini, L. A. (2013). RNA-guided editing of bacterial genomes using CRISPR-Cas systems. Nat Biotechnol 31, 233-239.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Jinek, M., East, A., Cheng, A., Lin, S., Ma, E., and Doudna, J. (2013). RNA-programmed genome editing in human cells. Elife 2, e00471.

Jinek, M., Jiang, F., Taylor, D. W., Stemnberg, S. H., Kaya, E., Ma, E., Anders, C., Hauer, M., Zhou, K., Lin, S., et al. (2014). Structures of Cas9 endonucleases reveal RNA-mediated conformational activation. Science 343, 1247997.

Kaminski, R., Chen, Y., Fischer, T., Tedaldi, E., Napoli, A., Zhang, Y., Kam, J., Hu, W., and Khalili, K. (2016). Elimination of HIV-1 Genomes from Human T-lymphoid Cells by CRISPR/Cas9 Gene Editing. Sci Rep 6, 22555.

Kearns, N. A., Genga, R. M., Enuameh, M. S., Garber, M., Wolfe, S. A., and Maehr, R. (2014). Cas9 effector-mediated regulation of transcription and differentiation in human pluripotent stem cells. Development 141, 219-223.

Kearns, N. A., Pham, H., Tabak, B., Genga, R. M., Silverstein, N. J., Garber, M., and Maehr, R. (2015). Functional annotation of native enhancers with a Cas9-histone demethylase fusion. Nat Methods 12, 401-403.

Lee, C. M., Cradick, T. J., and Bao, G. (2016). The *Neisseria meningitidis* CRISPR-Cas9 System Enables Specific Genome Editing in Mammalian Cells. Mol Ther 24, 645-654.

Ma, E., Harrington, L. B., O'Connell, M. R., Zhou, K., and Doudna, J. A. (2015a). Single-Stranded DNA Cleavage by Divergent CRISPR-Cas9 Enzymes. Mol Cell 60, 398-407.

Ma, H., Naseri, A., Reyes-Gutierrez, P., Wolfe, S. A., Zhang, S., and Pederson, T. (2015b). Multicolor CRISPR labeling of chromosomal loci in human cells. Proc Natl Acad Sci USA 112, 3002-3007.

Makarova, K. S., Wolf, Y. I., Alkhnbashi, O 641. S., Costa, F., Shah, S. A., Saunders, S. J., Barrangou, R., Brouns, S. J., Charpentier, E., Haft, D. H., et al. (2015). An updated evolutionary classification of CRISPR-Cas systems. Nat Rev Microbiol 13, 722-736.

Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826.

Muller, M., Lee, C. M., Gasiunas, G., Davis, T. H., Cradick, T. J., Siksnys, V., Bao, G., Cathomen, T., and Mussolino, C. (2016). *Streptococcus thermophilus* CRISPR-Cas9 Systems Enable Specific Editing of the Human Genome. Mol Ther 24, 636-644.

Nihongaki, Y., Kawano, F., Nakajima, T., and Sato, M. (2015). Photoactivatable CRISPR-Cas9 for optogenetic genome editing. Nat Biotechnol 33, 755-760.

Nunez, J. K., Harrington, L. B., and Doudna, J. A. (2016). Chemical and Biophysical Modulation of Cas9 for Tunable Genome Engineering. ACS Chem Biol 11, 681-688.

Orthwein, A., Noordermeer, S. M., Wilson, M. D., Landry, S., Enchev, R. I., Sherker, A., Munro, M., Pinder, J., Salsman, J., Dellaire, G., et al. (2015). A mechanism for the suppression of homologous recombination in G1 cells. Nature 528, 422-426.

Ousterout, D. G., Kabadi, A. M., Thakore, P. I., Majoros, W. H., Reddy, T. E., and Gersbach, C. A. (2015). Multiplex CRISPR/Cas9-based genome editing for correction of dystrophin mutations that cause Duchenne muscular dystrophy. Nat Commun 6, 6244.

Pattanayak, V., Lin, S., Guilinger, J. P., Ma, E., Doudna, J. A., and Liu, D. R. (2013). High throughput profiling of off-target DNA cleavage reveals RNA-programmed Cas9 nuclease specificity. Nat Biotechnol 31, 839-843.

Pawluk, A., Bondy-Denomy, J., Cheung, V. H., Maxwell, K. L., and Davidson, A. R. (2014). A new group of phage anti-CRISPR genes inhibits the type I-E CRISPR-Cas system of *Pseudomonas aeruginosa*. MBio 5, e00896.

Pawluk, A., Staals, R. H. J., Taylor, C., Watson, B. N. J., Saha, S., Fineran, P. C., Maxwell, K. L., and Davidson, A. R. (2016). Inactivation of CRISPR-Cas systems by anti-CRISPR proteins in diverse bacterial species. Nature Microbiology.

Peranen, J., Rikkonen, M., Hyvonen, M., and Kaariainen, L. (1996). T7 vectors with modified T7lac promoter for expression of proteins in Escherichia coli. Anal Biochem 236, 371-373.

Price, M. N., Dehal, P. S., and Arkin, A. P. (2009). FastTree: computing large minimum evolution trees with profiles instead of a distance matrix. Mol Biol Evol 26, 1641-1650.

Price, M. N., Dehal, P. S., and Arkin, A. P. (2010). FastTree 2-approximately maximum likelihood trees for large alignments. PLoS One 5, e9490.

Ran, F. A., Cong, L., Yan, W. X., Scott, D. A., Gootenberg, J 674. S., Kriz, A. J., Zetsche, B., Shalem, O., Wu, X., Makarova, K. S., et al. (2015). In vivo genome editing using *Staphylococcus aureus* Cas9. Nature 520, 186-191.

Richter, C., Dy, R. L., McKenzie, R. E., Watson, B. N., Taylor, C., Chang, J. T., McNeil, M. B., Staals, R. H., and Fineran, P. C. (2014). Priming in the Type I-F CRISPR-Cas system triggers strand-independent spacer acquisition, bi-directionally from the primed protospacer. Nucleic Acids Res 42, 8516-8526.

Takeuchi, N., Wolf, Y. I., Makarova, K. S., and Koonin, E. V. (2012). Nature and intensity of selection pressure on CRISPR-associated genes. J Bacteriol 194, 1216-1225.

Touchon, M., Bernheim, A., and Rocha, E. P. (2016). Genetic and life-history traits associated with the distribution of prophages in bacteria. ISME J.

van Houte, S., Ekroth, A. K., Broniewski, J. M., Chabas, H., Ben, A., Bondy-Denomy, J., Gandon, S., Boots, M., Paterson, S., Buckling, A., et al. (2016). The diversity-generating benefits of a prokaryotic adaptive immune system. Nature.

Villefranc, J. A., Amigo, J., and Lawson, N. D. (2007). Gateway compatible vectors for analysis of gene function in the zebrafish. Dev Dyn 236, 3077-3087.

Wang, H., La Russa, M., and Qi, L. S. (2016). CRISPR/Cas9 in Genome Editing and Beyond. Annu Rev Biochem 85, 227-264.

Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas mediated genome engineering. Cell 153, 910-918.

Wei, Y., Terns, R. M., and Terns, M. P. (2015). Cas9 function and host genome sampling in Type II-A CRISPR-Cas adaptation. Genes Dev 29, 356-361.

Wright, A. V., Sternberg, S. H., Taylor, D. W., Staahl, B. T., Bardales, J. A., Kornfeld, J. E., and Doudna, J. A. (2015). Rational design of a split-Cas9 enzyme complex. Proc Natl Acad Sci USA 112, 2984-2989.

Wu, Y., Liang, D., Wang, Y., Bai, M., Tang, W., Bao, S., Yan, Z., Li, D., and Li, J. (2013). Correction of a genetic disease in mouse via use of CRISPR-Cas9. Cell Stem Cell 13, 659-662.

Yen, S. T., Zhang, M., Deng, J. M., Usman, S. J., Smith, C. N., Parker-Thornburg, J., Swinton, P. G., Martin, J. F., and Behringer, R. R. (2014). Somatic mosaicism and allele complexity induced by CRISPR/Cas9 RNA injections in mouse zygotes. Dev Biol 393, 3-9.

Yin, H., Xue, W., Chen, S., Bogorad, R. L., Benedetti, E., Grompe, M., Koteliansky, V., Sharp, P. A., Jacks, T., and Anderson, D. G. (2014). Genome editing with Cas9 in adult mice corrects a disease mutation and phenotype. Nat Biotechnol 32, 551-553.

Zhang, Y., Heidrich, N., Ampattu, B. J 708., Gunderson, C. W., Seifert, H. S., Schoen, C., Vogel, J., and Sontheimer, E. J. (2013). Processing-independent CRISPR RNAs limit natural transformation in *Neisseria meningitidis*. Mol Cell 50, 488-503.

Zhang, Y., Rajan, R., Seifert, H. S., Mondragon, A., and Sontheimer, E. J. (2015). DNase H Activity of *Neisseria meningitidis* Cas9. Mol Cell 60, 242-255.

We claim:

1. A method, comprising:

a) providing:

i) a biological cell comprising at least one suspect gene;

ii) a Type II-C Cas9/sgRNA complex wherein said Type II-C Cas9 comprises a binding site; and iii) an anti-CRISPR (Acr) protein expressed from a plasmid, said plasmid comprising a native phage-encoded Acr open reading frame gene sequence, wherein said Acr protein is capable of binding with specific affinity to said binding site;

b) contacting said Type II-C Cas9/sgRNA complex with said biological cell such that said Type II-C Cas9/sgRNA complex hybridizes to a target site;

c) editing said suspect gene with said Type II-C Cas9/sgRNA complex; and d) contacting said binding site with said Acr protein such that said editing is reduced, wherein said Acr protein is selected from the group consisting of AcrIIC1Bo having the sequence of SEQ ID NO: 2), AcrIICIBoe having the sequence of SEQ ID NO: 27, AcrIIC1Nme having the sequence of SEQ ID NO: 4, AcrIIC2Nme having the sequence of SEQ ID NO: 6, AcrIIC3Nme having the sequence of SEQ ID NO: 8, AcrIIC4Nme having the sequence of SEQ ID NO: 10; AcrIIC5Nme having the sequence of SEQ ID NO: 12, Acr6Rs having the sequence of SEQ ID NO: 14, and Acr7 Pa having the sequence of SEQ ID NO: 16.

2. The method of claim 1, wherein said Type II-C Cas9 is selected from the group consisting of a *Brackiella oedipodis* Cas9 protein, a *Neisseria meningitidis* Cas9 protein, a *Simonsiella muelleri* Cas9 protein, and a *Ralstonia solanacearum* Cas9 protein.

3. The method of claim 1, wherein said reduced editing prevents at least one off-target event of said Type II-C Cas9 editing.

4. The method of claim 3, wherein said at least one off-target event is selected from the group consisting of DNA cleavage and DNA mutation.

5. The method of claim 3, wherein said reduced editing occurs during the G1 phase of the cell cycle.

6. The method of claim 1, wherein said reduced editing prevents mosaic genotypes.

7. The method of claim 1, wherein said reduced editing inhibits a gene drive.

8. The method of claim 1, wherein said reduced editing is selected from the group consisting of at least 70%, 75%, 90% or greater and 100%.

9. The method of claim 1, wherein said reduced editing is precisely controlled.

10. The method of claim 1, wherein said suspect gene is a dysfunctional gene.

* * * * *